(12) United States Patent
Kloosterman et al.

(10) Patent No.: US 11,781,170 B2
(45) Date of Patent: Oct. 10, 2023

(54) METHODS FOR PREPARING NUCLEIC ACID MOLECULES FOR SEQUENCING

(71) Applicant: UMC Utrecht Holding B.V., Utrecht (NL)

(72) Inventors: Wigard Pieter Kloosterman, Bunnik (NL); Jeroen de Ridder, Utrecht (NL); Alessio Marcozzi, Utrecht (NL)

(73) Assignee: UMC Utrecht Holding B.V., Utrecht (NL)

( * ) Notice: Subject to any disclaimer, the term of this patent is extended or adjusted under 35 U.S.C. 154(b) by 397 days.

(21) Appl. No.: 16/771,653

(22) PCT Filed: Dec. 11, 2018

(86) PCT No.: PCT/NL2018/050831
§ 371 (c)(1),
(2) Date: Jun. 10, 2020

(87) PCT Pub. No.: WO2019/117714
PCT Pub. Date: Jun. 20, 2019

(65) Prior Publication Data
US 2021/0180109 A1     Jun. 17, 2021

(30) Foreign Application Priority Data
Dec. 11, 2017    (EP) .................................... 17206503

(51) Int. Cl.
*C12Q 1/6806* (2018.01)
*C12Q 1/6869* (2018.01)

(52) U.S. Cl.
CPC ......... *C12Q 1/6806* (2013.01); *C12Q 1/6869* (2013.01)

(58) Field of Classification Search
None
See application file for complete search history.

(56) References Cited

U.S. PATENT DOCUMENTS

| 2010/0069263 A1 | 3/2010 | Shendure et al. |
| 2015/0159196 A1* | 6/2015 | Travers ................ C12Q 1/6869 506/3 |
| 2016/0376647 A1 | 12/2016 | Travers et al. |

FOREIGN PATENT DOCUMENTS

| WO | 00/15779 A2 | 3/2000 |
| WO | 20015/188192 A2 | 12/2015 |

OTHER PUBLICATIONS

Thibault, Production of DNA minicircles less than 250 base pairs through a novel concentrated DNA circularization assay enabling minicircle design with NF-kB inhibition activity, Nucleic Acids Research, 45(5): 1-11, 2016. (Year: 2016).*
Ramos, pELMO, an optimized in-house cloning vector, AMB Expr, 7(26): 1-8, 2017. (Year: 2017).*
Palatinszky, Preferential ligation during TA-cloning of multitemplate PCR products—a factor causing bias in microbial community structure analysis, J Microbiol Methods, 85(2): 131-136, 2011. (Year: 2011).*
International Search Report for International Application No. PCT/NL2018/050831, dated Apr. 12, 2019, 4 pages.
International Written Opinion for International Application No. PCT/NL2018/050831, dated Apr. 12, 2019, 8 pages.
International Preliminary Report on Patentability for International Application No. PCT/NL2018/050831, dated Mar. 13, 2020, 19 pages.

* cited by examiner

*Primary Examiner* — Angela M. Bertagna
*Assistant Examiner* — Carolyn L Greene
(74) *Attorney, Agent, or Firm* — TraskBritt

(57) ABSTRACT

Means and methods for preparing double stranded target DNA molecules for sequencing. In embodiments double stranded backbone DNA molecules comprising 5' and 3' ends are provided that are: ligation compatible with 5' and 3' ends of the target DNA; form a first restriction enzyme recognition site when self-ligated; in a form that enables self-ligation. Methods may comprise providing, if not already present, the target DNA with 5' and 3' ends that are in a form that prevents self-ligation and that are ligation compatible with the backbone DNA 5' and 3' ends. Methods may further comprise ligating the target DNA to the backbone DNA in the presence of a ligase and a first restriction enzyme that cuts the first restriction enzyme recognition site, thereby producing at least one DNA circle comprising a backbone DNA molecule and a target DNA molecule. Linear DNA may be removed at this time and subsequently a concatemer DNA molecule comprising an ordered array of copies of the at least one DNA circle through rolling circle amplification is produced that can be sequenced.

10 Claims, 17 Drawing Sheets
Specification includes a Sequence Listing.

A

B

Figure 2
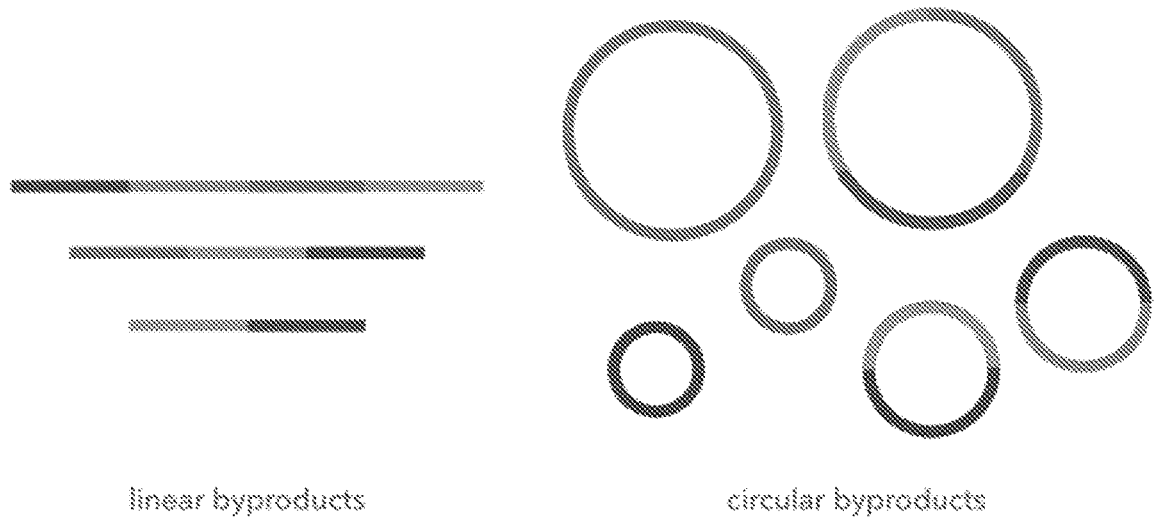
linear byproducts    circular byproducts
Figure 3
```
      (1)       (2)       (3)         (4)           (5)       (6)     (1)
5'-GGGC..CCTCAGC..ATTTAAAT..GTCTTCgaGAAGAC..catactatcatg..(N)..GCCC-3'
3'-CCCG..GGAGTCG..TAAATTTA..CAGAAGctCTTCTG..gtatgatagtac..(N)..CGGG-5'
```
Figure 4
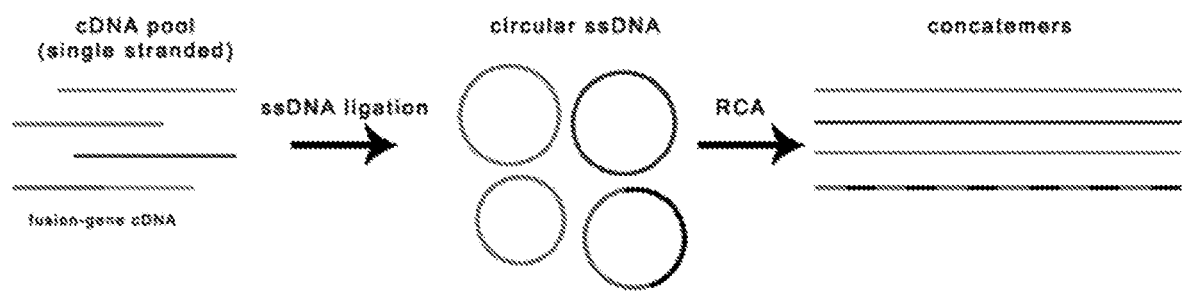

A

B

A

B

METHODS FOR PREPARING NUCLEIC ACID MOLECULES FOR SEQUENCING

CROSS-REFERENCE TO RELATED APPLICATIONS

This application is a national phase entry under 35 U.S.C. § 371 of International Patent Application PCT/NL2018/050831, filed Dec. 11, 2018, designating the United States of America and published in English as International Patent Publication WO 2019/117714 A1 on Jun. 20, 2019, which claims the benefit under Article 8 of the Patent Cooperation Treaty to European Patent Application Serial No. 17206503.9, filed Dec. 11, 2017.

STATEMENT REGARDING ELECTRONIC FILING OF A SEQUENCE LISTING

Pursuant to 37 C.F.R. § 1.821, a Sequence Listing ASCII text file entitled "P115546US00 seqlist_ST25.txt," 19,292 bytes in size, generated Feb. 2, 2023, has been submitted via EFS-Web. This Sequence Listing is hereby incorporated by reference into the specification for its disclosures.

TECHNICAL FIELD

The application relates to means and methods for determining the sequence of nucleic acid molecules. In particular, the disclosure relates to methods that leverage rolling circle amplification of the nucleic acid molecules of which the sequence is to be determined.

BACKGROUND

Sequencing methods have evolved over time. The old Sanger sequencing method has been replaced by the now common next generation sequencing (NGS) methods. These methods have recently been review in Goodwin et al (2016; Nature Reviews|Genetics Volume 17:pp 333-351: doi: 10.1038/nrg.2016.49). The most common NGS methods rely on the sequencing of short stretches of DNA. Sequencing techniques for short stretches of DNA suffer from inherent error profiles. Errors are reduced by independently sequencing multiple copies of the same target sequence. However, for each individual sequence read it is impossible to determine whether a change represents an error or a true mutation. The cumulative evidence across several independent sequence reads allows for the filtering of mutations introduced during amplification and errors in sequencing. Longer target DNAs can also be sequenced with short read methods. This is typically done by sequencing overlapping fragments that can be aligned to create an assembled longer sequence. This so-called short read paired end technique has been very successful in the sequencing of large target nucleic acid and has been instrumental in the various genome projects. The genome projects have revealed that genomes are highly complex with many long repetitive elements, copy number alterations and structural variations. Many of these elements are so long that short-read paired-end technologies are insufficient to resolve them. Long-read sequencing delivers reads in excess of several kilobases and allows for the resolution of these large structural features in whole genomes. Two popular platforms for long read sequencing are the Pacific Biosciences systems (the RSII and the Sequel) and the Oxford Nanopore systems (MK1 MinION and PromethION). Both are single-molecule sequencers. Both platforms allow reads in excess of 55 kb and longer. However, these systems have even higher error rates than next (second) generation sequencers. These errors can be reduced by increasing the number of times the same target nucleic acid is sequenced (Goodwin et al 2016; doi: 10.1038/nrg.2016.49).

This disclosure provides novel solutions for the preparation of nucleic acid molecules for sequencing.

BRIEF SUMMARY

An embodiment of the disclosure provides a method for preparing double stranded target DNA molecules for sequencing, comprising
  providing double stranded backbone DNA molecules comprising 5' and 3' ends that are:
    ligation compatible with 5' and 3' ends of the target DNA;
    form a first restriction enzyme recognition site when self-ligated;
    in a form that enables self-ligation; and
    providing, if not already present, the target DNA with 5' and 3' ends that are in a form that prevents self-ligation and that are ligation compatible with the backbone DNA 5' and 3' ends;
  the method further comprising
  ligating the target DNA to the backbone DNA in the presence of a ligase and a first restriction enzyme that cuts the first restriction enzyme recognition site, thereby producing at least one DNA circle comprising a backbone DNA molecule and a target DNA molecule;
  optionally removing linear DNA;
  producing a concatemer DNA molecule comprising an ordered array of copies of the at least one DNA circle through rolling circle amplification; and
  sequencing the at least one concatemer.

Also provided is a collection of DNA molecules (backbones) of a length of 50-1000 nucleotides that comprise 5' ends that comprise a part of a first restriction enzyme recognition site at the extreme end and 3' ends that comprise the other part of a first restriction enzyme recognition site at the extreme end, and which 5' and 3' ends are ligation compatible with each other and may form a restriction enzyme recognition (first restriction enzyme) site when self-ligated and wherein each of the backbones comprises:
  a linker;
  optionally an identifier sequence that differs from the sequence of identifiers of other backbones in the collection (barcode);
  optionally a second identifier that is unique for a collection of backbone molecules;
  and optionally a restriction site for a nicking enzyme.

Further provided is a method for determining the sequence of a collection of nucleic acid molecules comprising
  providing double stranded target DNA molecules that have 5' and 3' ends with a protruding adenine residue at the 3"-end of both strands of the DNA molecules;
  providing a collection of double stranded backbone DNA molecules that
  comprise 5' and 3' ends that are ligation compatible with the 5' and 3' ends of the target DNA;
  the method further comprising
  ligating the target DNA to the backbones in the presence of a ligase, thereby producing DNA circles comprising a backbone and a target DNA molecule;
  optionally removing linear DNA;
  producing concatemers comprising an ordered array of copies of at least two of the DNA circles through rolling circle amplification; and
  sequencing the concatemers.

Further provided is a method for determining the sequence of a collection of nucleic acid molecules comprising providing double stranded target DNA molecules that have a recombinase recognition site specific for a target site specific recombinase at the 5' and the 3' ends;
providing a backbone comprising the recognition sites separated by DNA comprising a linker;
incubating the target DNA molecules with the backbones in the presence of the target site specific recombinase, preferably a Cre recombinase, a FLP recombinase or a bacteriophage lambda integrase, thereby producing DNA circles comprising a backbone and a target DNA molecule;
optionally removing linear DNA; and;
producing concatemers comprising an ordered array of copies of at least two of the DNA circles through rolling circle amplification; and
sequencing the concatemers. In a preferred embodiment, the backbone is a circle comprising two recombinase recognition sites separated on one side by DNA comprising a linker and separated on the other side by DNA coding for a restriction enzyme recognition site, and wherein the restriction site is the only recognition site for the restriction enzyme in the backbone. In this embodiment, the method preferably further comprises digesting the DNA after the recombination with the restriction enzyme and subsequently removing linear DNA, prior to producing the concatemers.

Further provided is a method for determining the sequence of a collection of nucleic acid molecules comprising providing double stranded target DNA molecules that have a recombinase recognition site specific for a target site specific recombinase at the 5' and the 3' ends;
providing a collection of double stranded circular backbone DNA molecules that
comprise the recombinase recognition site and a linker;
the method further comprising
incubating the target DNA with the backbones in the presence of a target site specific recombinase for the recognition sites, thereby producing DNA circles comprising a backbone and a target DNA molecule;
optionally removing linear DNA;
producing concatemers comprising an ordered array of copies of at least two of the DNA circles through rolling circle amplification; and
sequencing the concatemers.

Further provided is a kit comprising one or more backbones.

BRIEF DESCRIPTION OF THE DRAWINGS

FIG. 2. Examples of possible linear and circular byproducts of the circularization reaction indicated in FIG. 1. The shading of the big circle in the top left of the circular byproduct figure indicates backbone sequences. The other shadings are all target sequences.

FIG. 3. Schematic example of a double stranded backbone sequence.

1) Indicates a 5' end (SEQ ID NO:1) and 3' end (SEQ ID NO:52) sequence that together code for a first restriction enzyme recognition site.

(2) Is a restriction site for the nicking enzyme BbvCI. Any other nicking site would work as well, an advantage of using BbvCI however is that two forms of that enzyme are commercially available, one nicks the DNA at the plus strand and the other at the minus strand. A nicked DNA is a valid priming site for a Rolling Circle Amplification (RCA) reaction. Depending on the case, nicked DNA may be used instead of DNA-primers to initiate the polymerization.

(3) Is an accessory blunt restriction site, in the example case it is the recognition site of SweI. A second blunt restriction site allows the capture of a second DNA fragment in a further circularization reaction.

(4) Is a cloning site, a double-inverted BbsI site in the example, which can be used for easy extension of the backbone via Golden-Gate or other types of cloning.

(5) Represents a flexible DNA stretch (linker). It can vary in length and aids efficient circularization.

(6) The capital N indicates a stretch of nucleic acids that code for a unique identifier. It is a barcode-like sequence. It can code for one or more (random) barcodes of any suitable size.

The elements (1) are located at the extremities, the elements 2-6 can have any order and can be present or not depending on the case.

FIG. 4. A method has been developed to detect gene fusions based on targeted cDNA synthesis, single-stranded DNA circularization (ssDNA) and targeted rolling circle amplification. The cDNA that is produced by a reverse transcriptase step is grey-shaded in the left hand panel. The bottom cDNA is a fusion gene DNA and has two shades indicating the part from one gene and the part of another gene. It is clear that the RCA assay yields concatemers of the fusions. The method can of course also be used to determine the sequence of one or more cDNA that are not the result of a fusion of genes.

Figure 5:
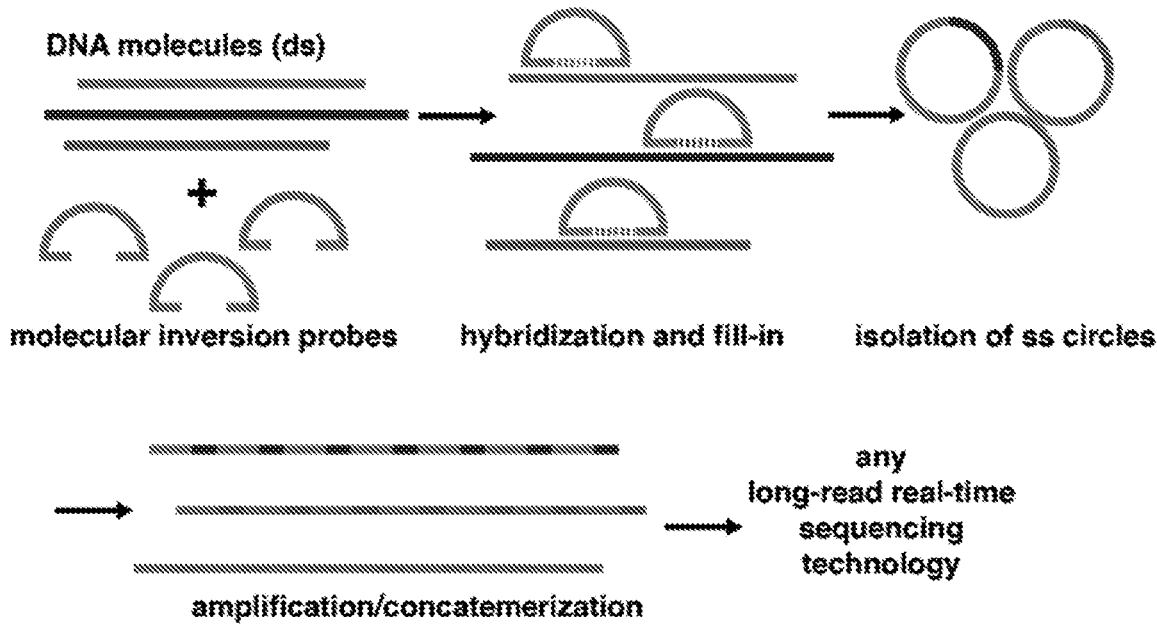

FIG. 5. Schematic representation of the MIP probes and method

Figure 6:
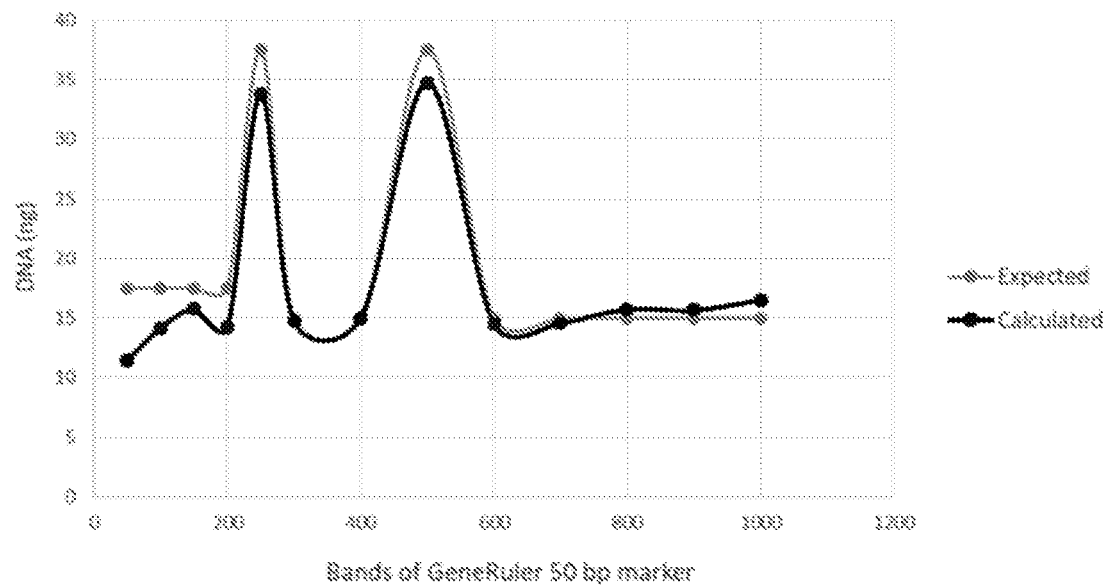

FIG. 6. The DNA content per band was plotted as well as the predicted value.

Figure 7:
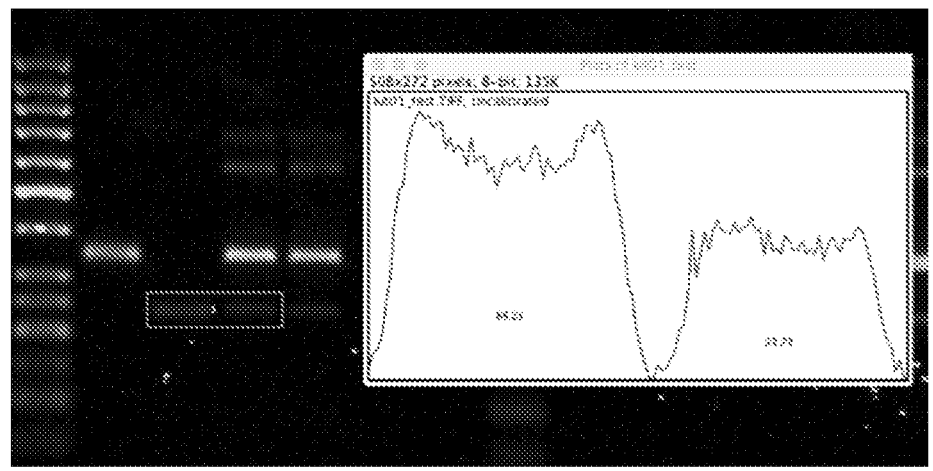
Figure 7:
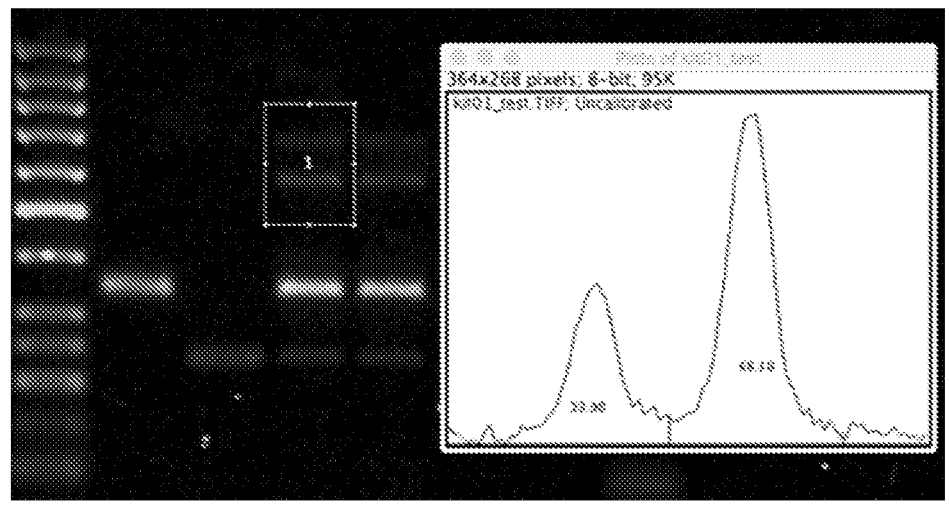

FIG. 7. Determining the efficiency of circularization: A) comparison of insert before and after the reaction. B) comparison of circularized product and unreacted product.

Figure 8:
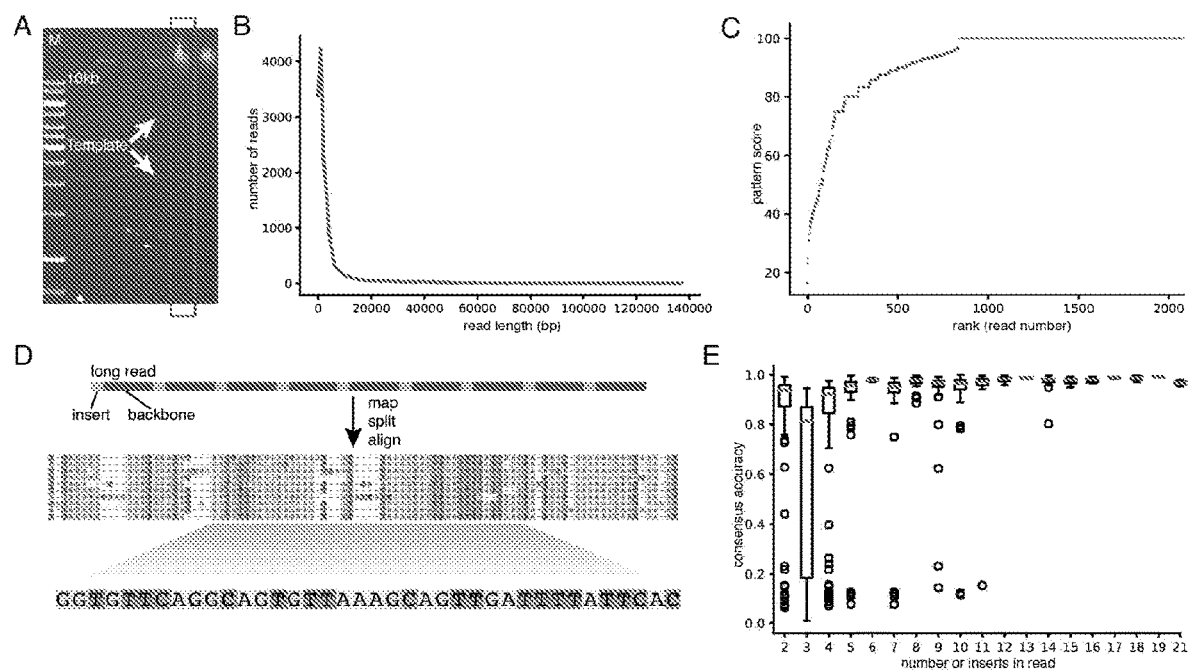

FIG. 8. Results of proof-of-concept experiment. (A) Gel picture indicating the RCA product that was used for subsequent sequencing on nanopore MinION. (B) Nanopore read length distribution of MinION R9.4 run that was performed with the sample indicated in (A) as input. (C) Pattern score distribution for 2,083 reads larger than 10 kb. (D) Schematic outline of a nanopore sequence read with alternating insert (green) and backbone (red), alignment of the insert sequences and generation of a consensus from the aligned inserts (SEQ ID NO:39); and (E) consensus accuracy.

Figure 9:
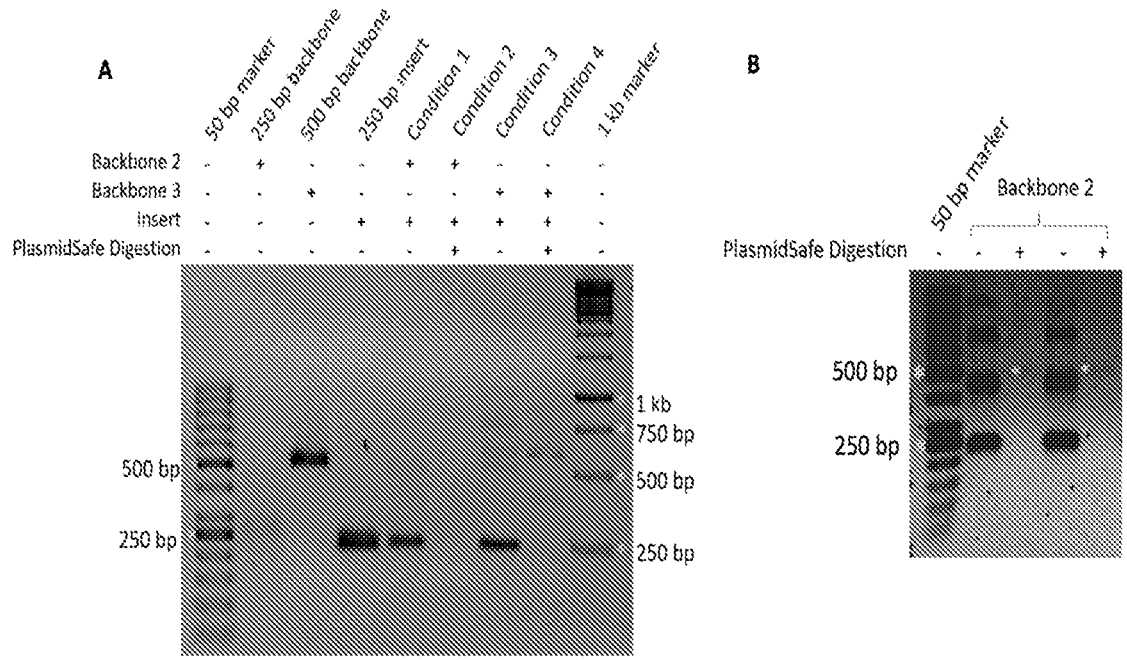

FIG. 9. Circularization of Backbone 2 (BB2) and Backbone 3 (BB3) with insert 17.2 at 3:1 ratio. A) comparison of BB2 and BB3. Red asterisk: correct circularized product. Multiple bands in condition 3: linear versus circular products, ligation of multiple backbones. Additional band in condition 4: circularized backbone. B) Successful circularization using Backbone 2 (BB2). Yellow asterisks: correct circularized product. In this gel the whole reaction was loaded on each lane. Lane 1 and 2 represent the circularization of BB2 and insert 17.2 at 1:1 ratio before and after PlasmidSafe digestion. Lane 3 and 4 represent the same circularization reaction using BB2 and insert 17.2 at 3:1 ratio.

Figure 10:
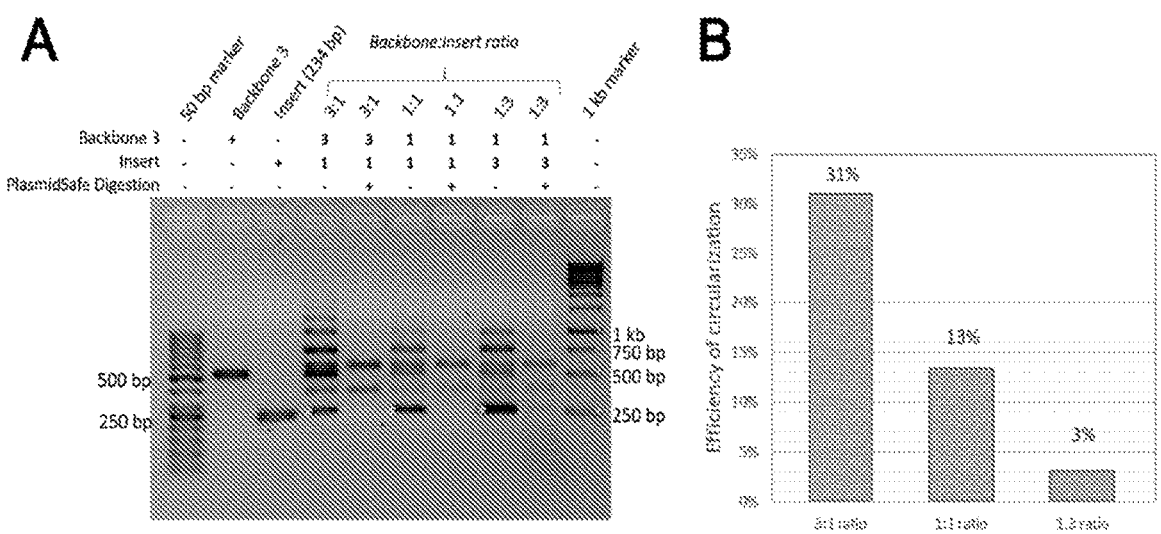

FIG. 10. Efficiency of backbone circularization with varying backbone-insert ratios. Ligation products of varying backbone (BB3) to insert (17.2) ratios were examined qualitatively and quantitatively. (A) Agarose gel displaying circularization input and reaction products. PlasmidSafe digestion was used to remove remaining linear products after the circularization reaction. Asterisks: correct circularized product. Asterisks: remainder of the insert input. (B) Quantification of the circularization efficiency. Quantification of the circularization efficiency was defined as P/I*100, where P is the amount of correct backbone-insert product (in moles, asterisks) and I is the amount of input insert (in moles). The intensity and surface area of the bands were measured using the software ImageJ (en.wikipedia.org/wiki/ImageJ). The data was normalized using the GeneRuler 50base pairs DNA ladder as a reference. See also Materials and Methods, section 10.

Figure 11:
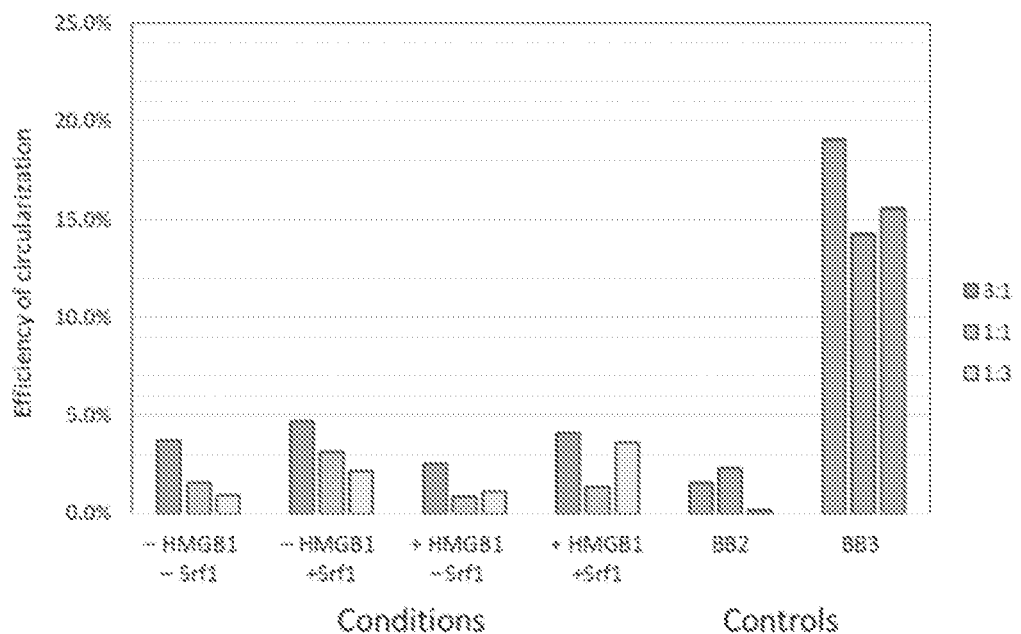

FIG. 11. The efficiency of circularization of BB2_100 (orange bars) with and without addition of SrfI and HMGB1. Ligation was performed using backbone:insert ratios. The blue bars represent the control experiments with BB2 and BB3 ligated with the same insert without addition of SrfI or HMGB1. Circularization efficiency was quantified as described above (FIG. 10 legend).

Figure 12:
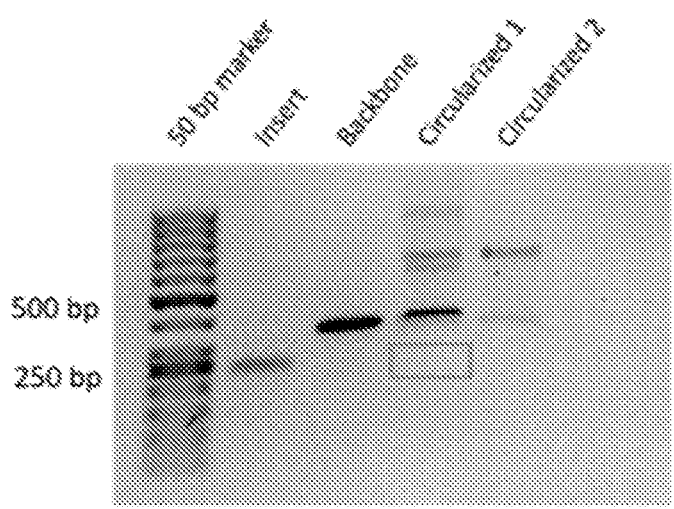

FIG. 12. Visual display of reaction products of the circularization with backbone BB2_100 and insert 17.2. Red asterisk: correct product. Orange box: predicted position of residual insert after circularization. The insert was completely ligated as shown by the full disappearance of the insert band after ligation (Circularized 1). Circularized 1: before Plasmid Safe DNAse treatment. Circularized 2: after Plasmid Safe DNAse treatment.

Figure 13:
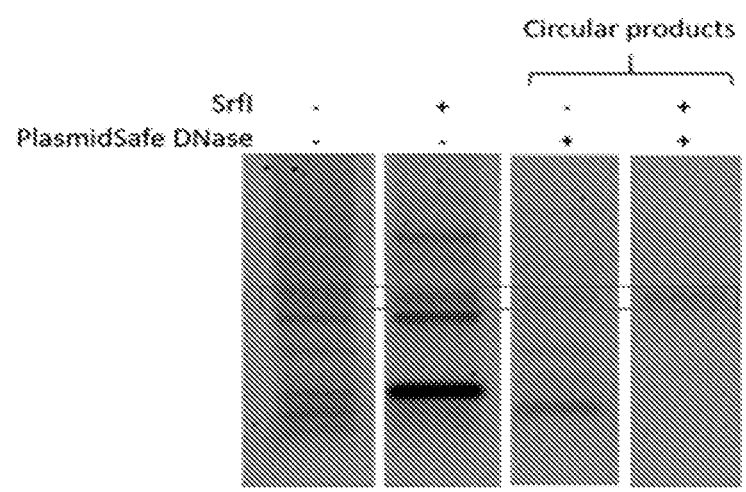

FIG. 13. The effect of the addition of the restriction enzyme SrfI in the circularization reaction. A circularization reaction was performed using BB3 together with insert 17.2. The reaction was performed in presence and absence of SrfI and plasmid safe DNAse.

Figure 14:
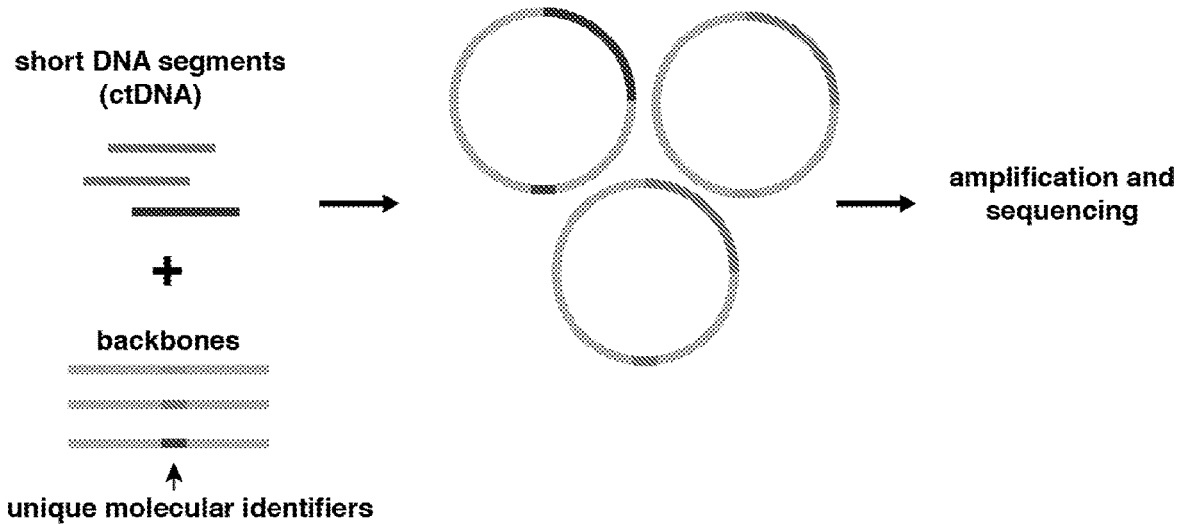
Figure 14:
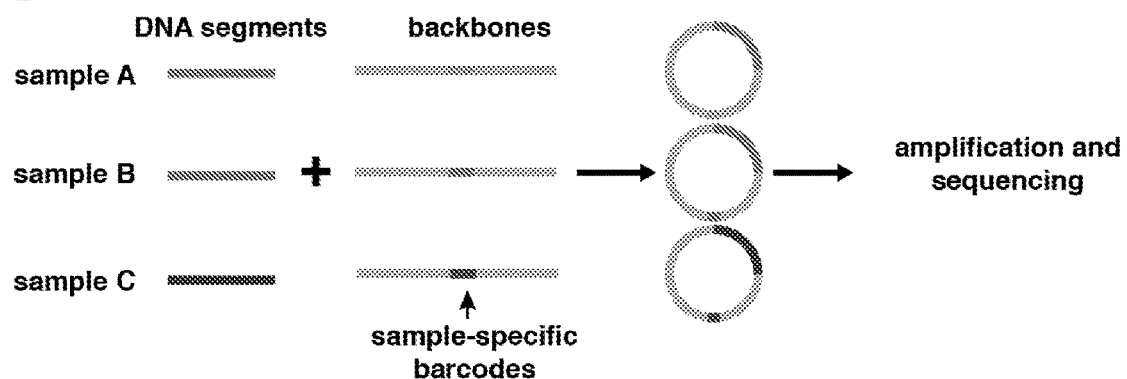

FIG. 14. Barcoding strategies useful with the described technology. (A) Use of unique molecular identifiers to tag individual DNA molecules for improving mutation discovery. (B) Use of sample-specific barcodes to label individual samples for pooling on a sequencing run.

Figure 15:
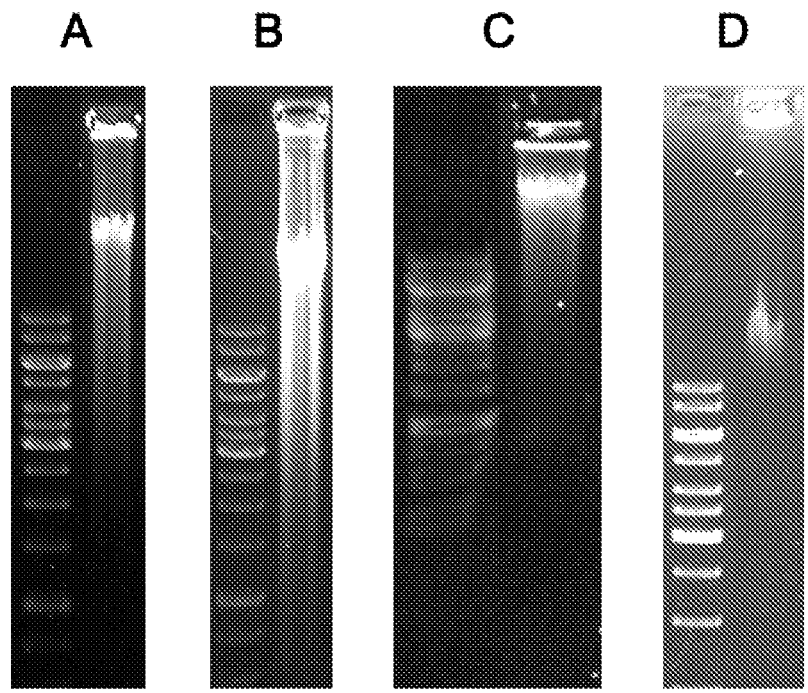

FIG. 15. RCA products using a variety of DNA templates. RCA was performed using circular DNA templates derived from a variety of sources. (A) cell-free DNA circularized with backbone BB2; (B) plasmid pX_Zeo; (C) ss-cDNA self-circularized using CircLigase II (Epicentre #CL9021K); (D) the PCR product 17.2 cloned into the plasmid pJET. As a reference, a long-range 1 Kb ladder was used. The higher band of the ladder is 10 Kb long, the RCA products are estimated to be between 20 and 100 kb long.

Figure 16:
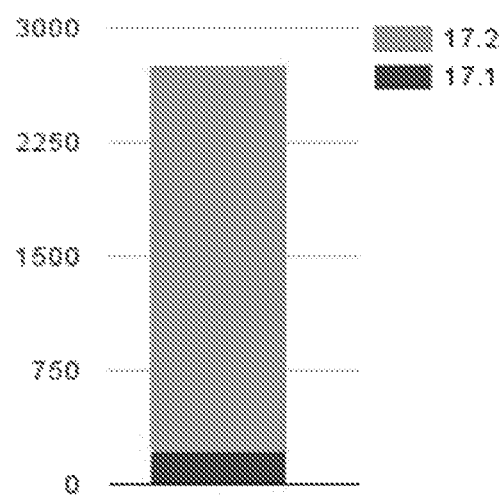

FIG. 16. Number of reads containing 17.1 and 17.2. The ratio between the reads containing 17.1 and the one containing 17.2 is 1:14, indicating a stark enrichment of the target region due to site-directed RCA.

Figure 17:
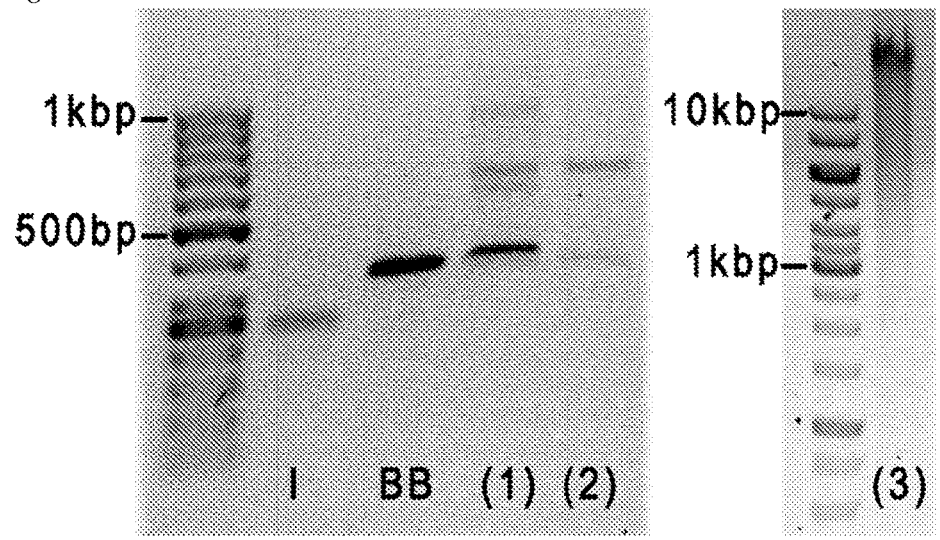

FIG. 17. Overview of reaction products of steps from a one-pot reaction design. An insert (17.2) and backbone (BB2_100) were circularized, yielding the products indicated with (1). Linear DNA products were digested using Plasmid Safe DNAse as indicated by (2). An RCA reaction product is formed based on (2) as input, as indicated by (3).

Figure 18:
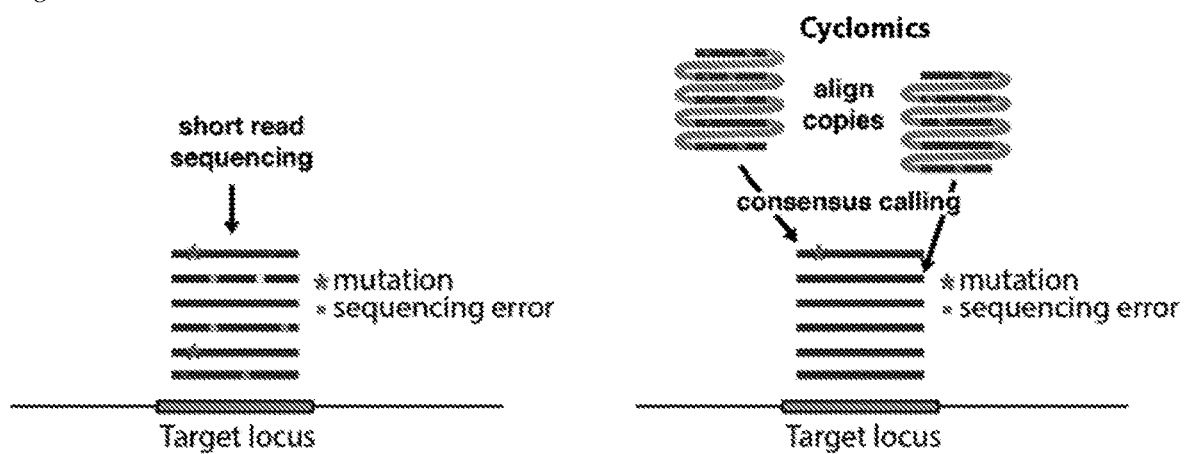

FIG. 18. Overview of consensus calling methods for short read sequencing (left panel) and long read sequencing (right panel).

Figure 19:
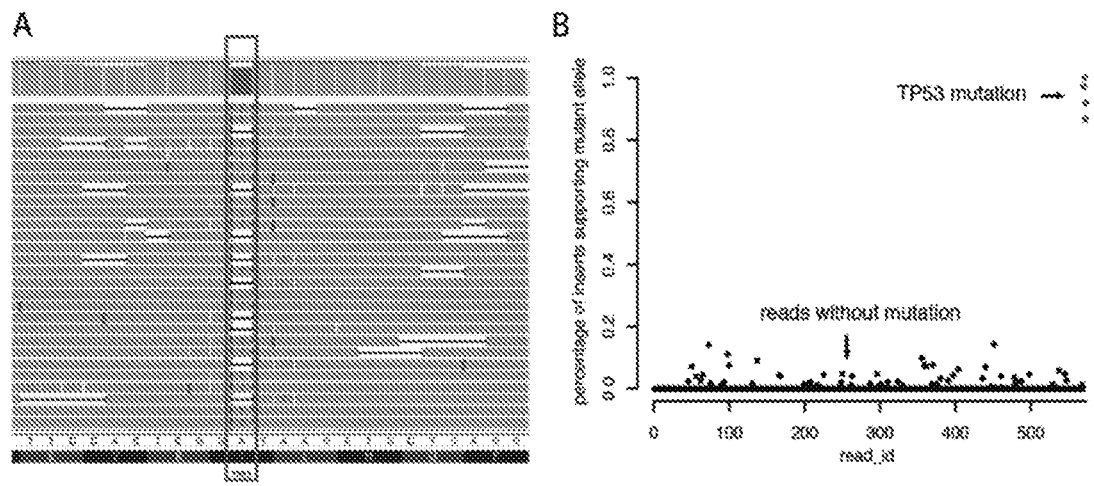

FIG. 19. (A) Example of mapped inserts with TP53 mutation derived one Cyclomics sequencing read. (B) Plot showing fraction of inserts that support a non-reference allele for 588 reads with >4 inserts. Four reads show a high fraction of non-reference allele and these contain inserts with the expected chr17:7578265, A→T mutation.

Figure 20:
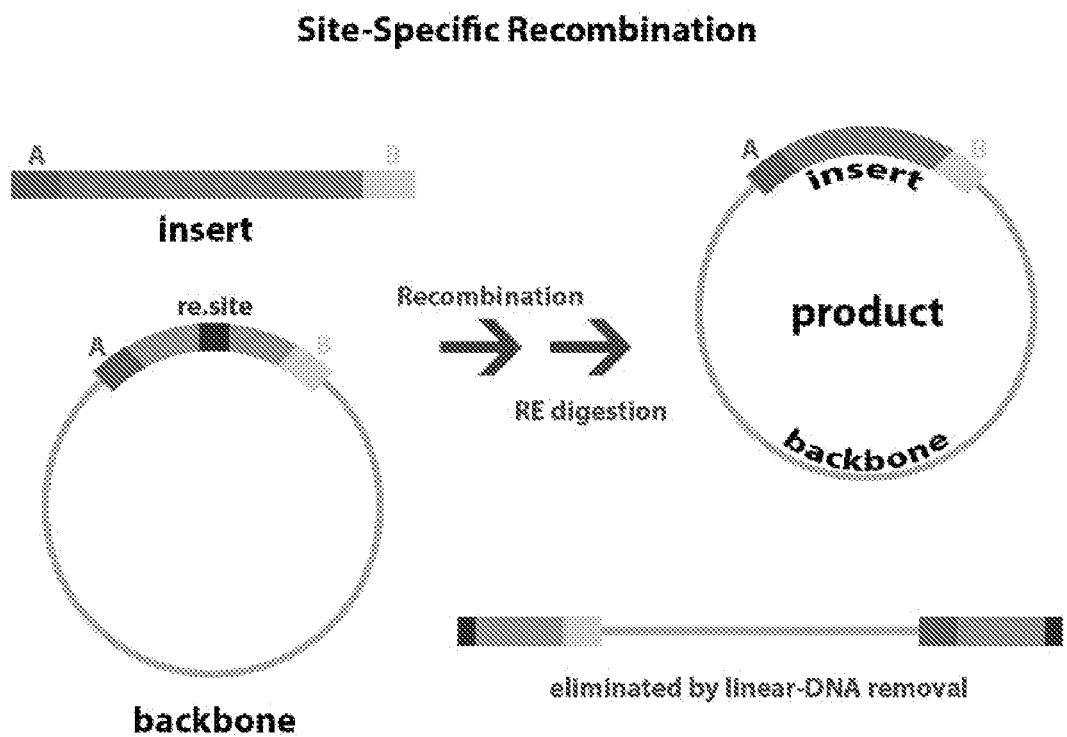

FIG. 20. Capture of DNA with a target site specific recombinase. The recognition sites for the target site specific recombinase are indicated by the letters A and B. The target DNA is indicated by the wording "insert". The sites A and B can be introduced in various ways such by ligating adaptors with the sites to the insert DNA or by amplifying the insert with primers that comprise a sequence coding for the sites A and B. The backbone is indicated by the term "backbone". In the figure, the backbone is a circular molecule comprising DNA between the two sites A and B. This intervening DNA comprises a restriction site that is unique to the entire backbone. The arrows indicate that the insert and the backbone are first recombined by adding the recombinase and that subsequently the restriction enzyme is added. The restriction enzyme will cut only unreacted backbone and backbones in which the linker is replaced by the insert. Linearized DNA can be removed by adding an appropriate exonuclease.

Figure 21:
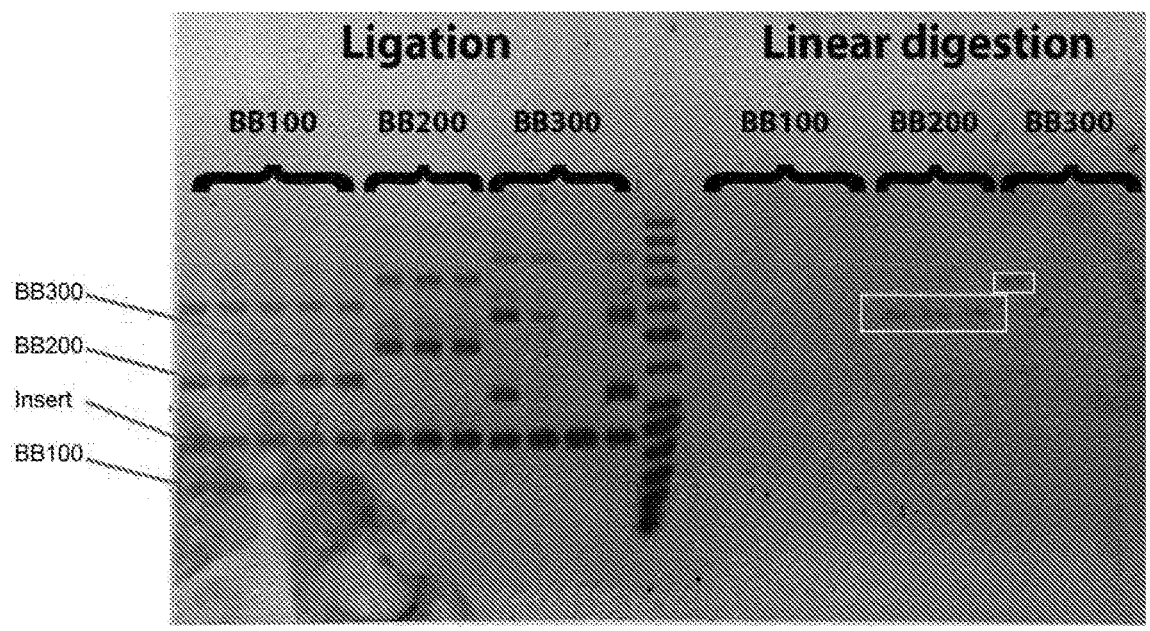

FIG. 21. Comparison between ligation reaction products and efficiency of different backbone designs. Left-side: Ligation of different backbones with a 250 bp PCR amplicon. Right-side remaining circular product after digestion of linear DNA with plasmid-safe DNAse. Ligation to all members of the BB200 series showed a high circularization efficiency, as demonstrated by the formation of circular product consisting of PCR product and backbone.

Figure 22:
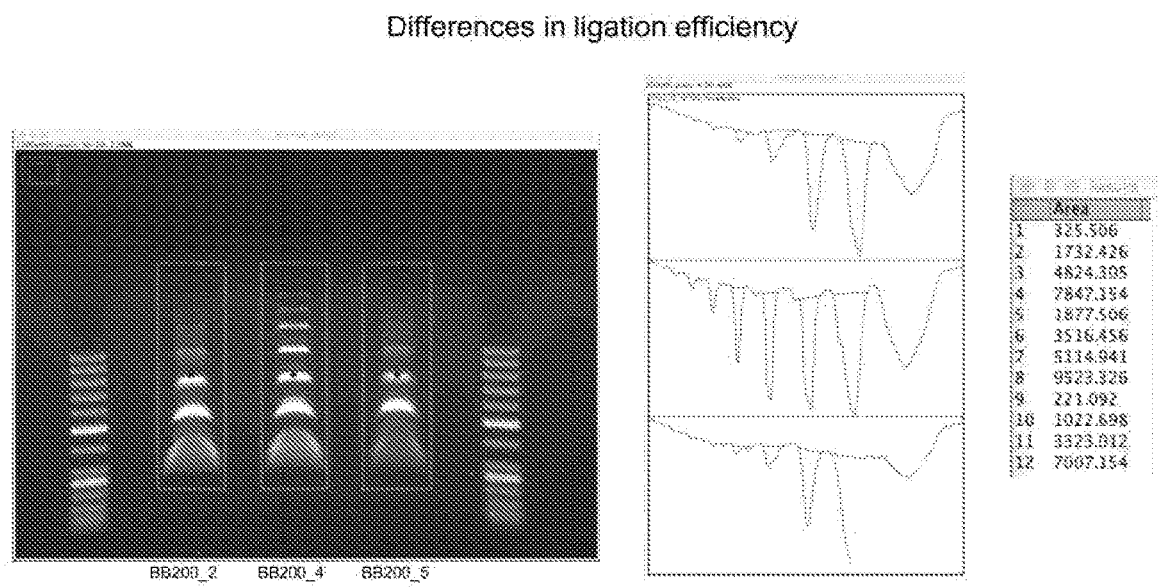

FIG. 22. Comparison of ligation efficiency of backbones from the BB200 series.

Left-side: gel showing the ligation product of the 3 backbones. BB200_4 showed brighter bands indicating more product formed during the reaction.

Right-side: measurements of the brightness of the bands. From top to bottom: BB200_2, BB200_4 and BB200_5.

Figure 23:
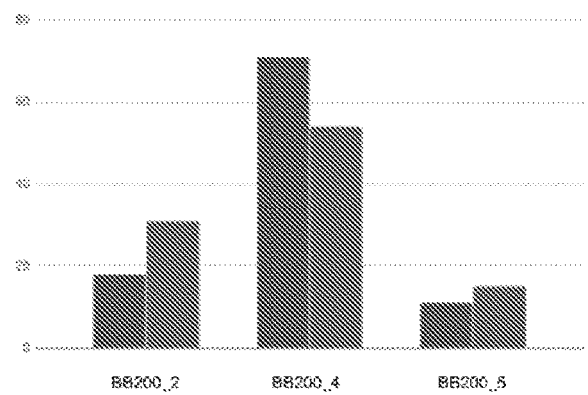

FIG. 23. Differences in number of sequencing reads derived from RCA products formed by ligation with backbones of the BB200 series.

Percent of reads coming from different backbones in two independent experiments (red and blue). The backbones were initially mixed at 1:1:1 ratio. The higher number of reads having BB200_4 is consistent with the higher ligation efficiency shown in FIG. 2.

Figure 24:
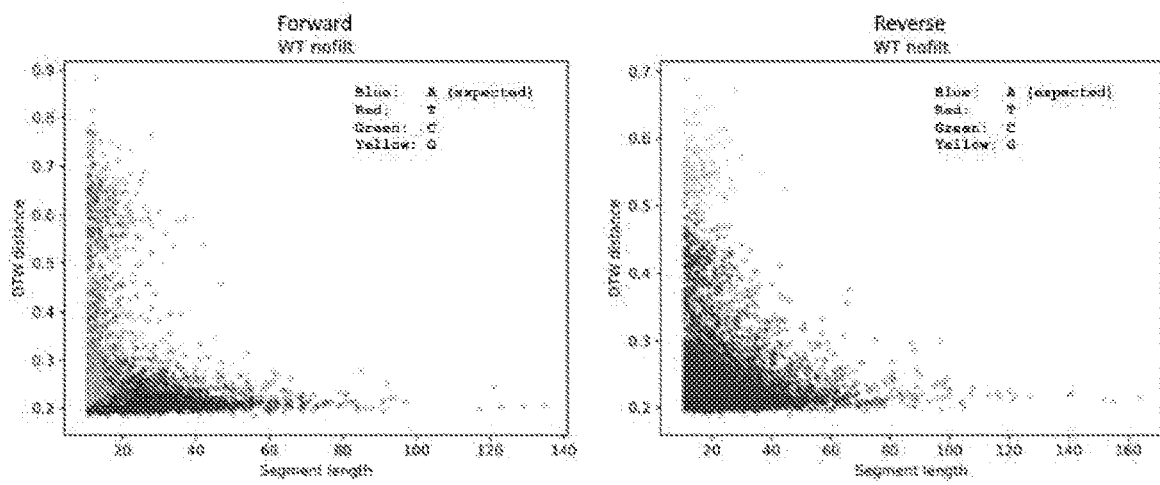

FIG. 24. Base inference of a particular position of the gene TP53 (GRCh37 17:7577518).

The Y-axis represents the distance (median fit score) between a modeled nanopore signal corresponding to a reference sequence and the signal derived from an experimental sequence. The greater the distance the more difficult it is to infer the correct base. On the X-axis are the number of inserts found in a read-segment. The inferred bases are indicated with different colors. The signal coming from the forward strand is less clear than the one measured on the reverse strand. This makes it difficult to distinguish the correct base (A, in blue) versus other possible bases even when the calculated distance is low.

Figure 25:
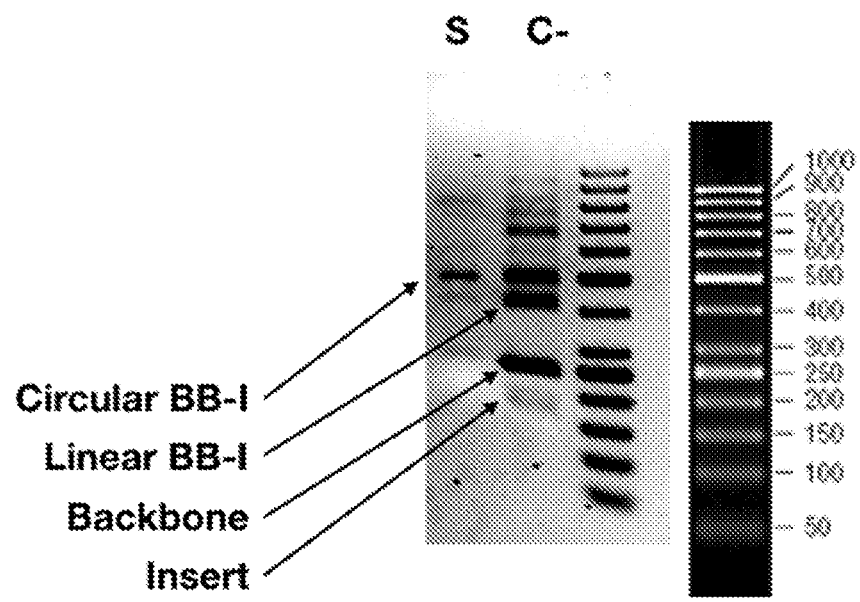

FIG. 25. Agarose gel depicting the product of a circularization reaction (S) between backbone and insert. The negative control is designated as C—. The band corresponding to the Circular BB-I product was isolated from gel.

Figure 26:
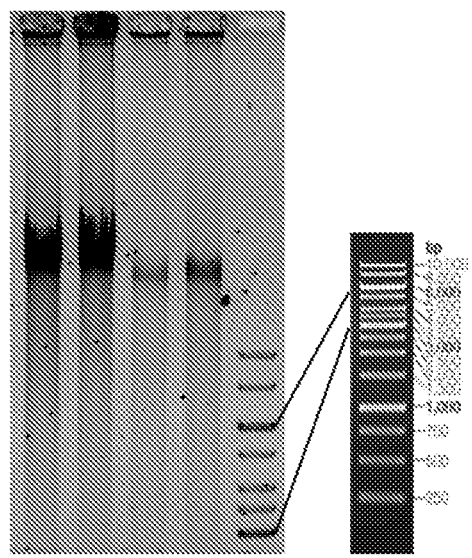

FIG. 26. Agarose gel showing example product after rolling circle amplification.

Figure 27:
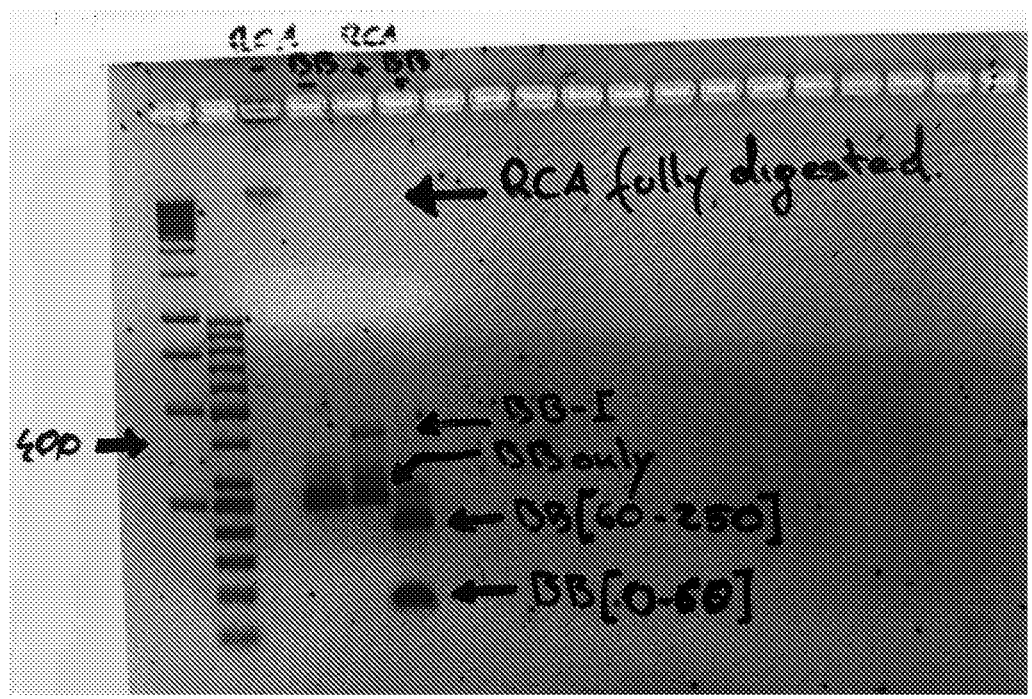

FIG. 27. BB200_4 (243 bp, indicated as BB in the figure) and S1_WT (158 bp, indicated as I in the figure) were circularized and amplified by RCA. When digesting concatemers made by BB-I, a band around 400 bp is expected, while if the concatemer consists of only BB, the resulting band should be around 250 bp. Concatemers formed by only I would not be digested leaving the RCA band visible.

DETAILED DESCRIPTION

Means and methods as described herein can determine the sequence of the same target DNA molecule multiple times. This can be used as a means to correct errors. This is different from classical second generation sequencing methods, which correct errors by sequencing multiple independent molecules covering the same genomic locus. In such cases each read typically represents one sequencing event of one molecule. With a method of the disclosure, a single (target) molecule is copied over and over so one read represents multiple sequencing events of the same molecule.

Target nucleic acid is typically double stranded DNA. Single stranded DNA or RNA of which the sequence needs to be determined can easily be converted into double stranded DNA by methods known in the art. Such methods include but are not limited to cDNA synthesis; reverse-transcriptase (RT) polymerase chain reaction (PCR); PCR; random prime extension and the like. The target DNA is linear or is made linear prior to performing the method.

A backbone is typically double stranded DNA. In methods that utilize a restriction enzyme to ligate target DNA into the backbone the backbones are typically linear or are made linear prior to or during the method. In methods that utilize a target site specific recombinase to insert target DNA into the backbone the backbones can be linear or are made circular prior to or during the method.

Self-ligation is herein defined as ligation of the 5' end to the 3' end of one and the same nucleic acid molecule.

The 5' and 3' ends of target DNAs are chosen such that they are ligation compatible with the 5' and 3' ends of backbones used in the reactions. With ligation compatible is meant that ligation of the ends to each other yields a double stranded DNA with correctly paired nucleotides without nicks in the ligation junction. Nicks can of course be introduced later to allow initiation of the RCA reaction. Blunt ends are ligation compatible with other blunt ends. DNA with sticky (also referred to as 'cohesive') ends are ligation compatible with other sticky ends if the protruding strands of DNA may be annealed together without leaving unpaired bases. Such is typically the case when the ends have a complementary sequence. 'Ligation compatible ends" are in the art also referred to as "compatible ends" or "compatible cohesive ends" or "compatible sticky ends".

Double stranded target DNA molecules comprise the sequence of the nucleic acid molecules of which the sequence is to be determined. The nucleic acid molecules of which the sequence is to be determined can already be double stranded DNA with 5' and 3' ends that are ligation compatible with the 5' and 3' ends of the backbone(s) to be used. Sometimes the nucleic acid needs to be made double stranded DNA, for instance, in the case of cDNA; or mRNA. The target DNA molecules can already have suitable 5' and 3' ends, for instance, a variety of polymerases produce blunt-end fragments. Such blunt end fragments are ligation compatible with backbones that have blunt 5' and 3' ends. The target nucleic acid can also be provided with suitable 5' and 3' ends, for instance, through digestion with an appropriate restriction enzyme or enzymes, or by addition of deoxynucleotides through terminal transferase. Suitable 5' ends and 3' ends can also be introduced through the insertion of a restriction enzyme site, recombinase recognition sites and/or homology regions. For instance, by ligating an adaptor containing the site(s) to the target DNA or by amplifying the target DNA with primers that contain the restriction enzyme site, recombinase recognition site and/or homology region.

Enzymes are available that leave ends that are ligation compatible with the ends of the backbone but that differ in the nucleotide(s) in the region immediately adjacent to the protruding ends. In this embodiment, it is preferred that the recognition site(s) of the enzyme(s) is/are not the same as the restriction enzyme site of the first restriction enzyme. In this way ligation of the compatible ends does not yield a site that can be cut by the first restriction enzyme. If a restriction enzyme is used to provide the target nucleic acid with appropriate ends, it is preferred that the enzyme is a blunt end producing enzyme. In one embodiment, the target DNA molecules are provided with 5' and 3' ends that are ligation compatible with the 5' and 3' ends of the backbones to be used, by digestion with one or more restriction enzymes.

In one embodiment, the ligation of an end of a target DNA to an end of a backbone creates a target-backbone junction with a sequence that cannot be recognized/cut by the restriction enzyme that cuts the (first) restriction enzyme site that is formed by self-ligation of a backbone.

In a preferred embodiment, the form that prevents self-ligation is a 5'-hydroxyl of one DNA terminus and 3'-hydroxyl of another and the form that allows self-ligation is a 5'-phosphate group of one DNA terminus and 3'-hydroxyl of another. Ligation requires the presence of a 5'-phosphate group. Removal by an appropriate phosphatase on both 5' ends of a nucleic acid molecule prevents self-ligation and ligation to other DNA molecules similarly treated. Ligation is prevented even if the ends have ligation compatible ends.

In one embodiment, the backbone comprises a recognition site for a nicking enzyme.

Target DNA molecules have 5' and 3' ends that are in a form that prevents self-ligation. Preferably the target DNA is in a form that prevents ligation to other target DNA molecules. Both requirements can be met by providing the ends in dephosphorylated form or by addition of nucleotides (3' overhang) at the 3' end of the target DNA molecules Self-ligation is inherently prevented when the 5' end 3' ends of the target DNA are ligation incompatible. Also in these cases, however, it is preferred that ligation to other target molecules is prevented. Thus also in these circumstances it is preferred that the ends are provided in dephosphorylated form. Incompatible ends are, for instance, but not limited to blunt ends and overhang ends or overhang ends wherein the protruding nucleotides (overhangs) of the ends are not compatible.

Prevention of self-ligation and/or prevention of ligation to other target DNA molecules does not have to be absolute. The processes can/will occur at some level. This can be tolerated in a method of the disclosure. Good reads can be obtained even with low ligation efficiencies.

The 5' and 3' end of the backbone DNA can be ligation compatible with each other. In such embodiments it is preferred that the 5' and 3' ends of the target DNA are also ligation compatible with each other. It is preferred that self-ligation of the ends of a backbone is not prevented. It is preferred that the 5' ends of the target DNA are dephosphorylated. It is preferred that the ligation is performed in the presence of a restriction enzyme that recognizes and cuts the first restriction enzyme site.

In embodiments where double stranded target DNA is captured the backbone is a double-stranded nucleic acid molecule. Such backbones comprise 5' and 3' ends that are ligation compatible with the 5' and 3' ends of the target DNA. The 5' and 3' ends of the backbone may also be ligation compatible with each other.

In embodiments a backbone includes one or more of the following parts:
- A 5' end coding for a first part of a first restriction site, preferably a first half of a first restriction site (see, for instance, 1 in the schematic example below),
- One or more sites that allow nicking of the double-stranded backbone sequence (see, for instance, 2 below),
- One or more type1 or type2 restriction sites (see, for instance, 3 below),
- A secondary cloning site (see, for instance, 4 below),
- A flexible DNA stretch that enables efficient circularization (bending) of the backbone molecule, 5 below)
- A unique molecular barcode (identifier) sequences to tag each individual backbone molecule (see, for instance, 6 below)
- A 3' end coding for the other part, preferably the other half of the mentioned first restriction site.
- Phosphorylation at the 5' ends of the backbone molecule and a hydroxyl group at the 3' ends of the backbone.
- A secondary barcode sequence that can be used to identify individual samples.

Schematic example of a double-stranded backbone sequence (SEQ ID NO:1 and SEQ ID NO:52, upper and lower respectively):

```
    (1)     (2)       (3)            (4)            (5)        (6)    (1)
5'-GGGC..CCTCAGC..ATTTAAAT..GTCTTCGAGAAGAC..CATACTATCATG..(N)..GCCC-3'

3'-CCCG..GGAGTCG..TAAATTTA..CAGAAGCTCTTCTG..GTATGATAGTAC..(N)..CGGG-5'
```

The dots represent 0 nucleotides; 1 nucleotide; 2 nucleotides or more.

The sequences GGGC and GCCC stand for halves of a restriction enzyme site. The sequence constitutes an SrfI site but another restriction enzyme site will also work. In the case of SrfI (GCCC|GGGC) and advantage is that it is a blunt end site. Another advantage is that it recognizes an 8-bases-long site while most of the commercially available alternatives recognize 6-bases-long sites.

It is preferred that the first restriction enzyme site does not occur in elsewhere in the backbone sequence.

Ligation of ligation compatible ends can create a restriction site. This is the case if the ends and flanking sequences (if any) code for the restriction enzyme site when ligated to each other. As an example; the end of a double stranded DNA molecule that has a single stranded end with the sequence 5'-AATT . . . is ligation compatible with a double stranded DNA molecule that has a single strand end with the sequence . . . TTAA-5', where the dots indicate the double strand part and the indications 5' or 3' the free end of the respective molecules. Ligation of the two ends yields a molecule with the double stranded sequence:

```
...AATT...

...TTAA...
```

The overhang is identical to the overhang that is created by the EcoRI restriction enzyme. Ligation creates the restriction site EcoRI only in some of the cases, i.e., in the case where the nucleotides in bold have the indicated bases:

```
...GAATTC...

...CTTAAG...
```

EcoRI cannot cut when the nucleotides in bold have different bases. The following sequences are, for instance, not cut by EcoRI:

```
...CAATTC...;   or  ...AAATTC...;   or  ...GAATTA...

...GTTAAG...;       ...TTTAAG...;       ...CTTAAT...
```

The sequence of the ends of the target DNA thus determines whether the ligation junction formed by ligation of compatible ends can be digested by the enzyme that cuts the first restriction enzyme site.

In embodiments a backbone can be optimized for insert capture efficiency, wherein greater efficiency is reflected by greater efficiency in circularization and rolling circle amplification (RCA) product formation. Insert capture efficiency of a backbone can be estimated by the amount of multimers that can be formed.

In methods for sequencing target DNA as described herein it is preferred that the ligation of target DNA to backbone DNA does not yield a first restriction enzyme recognition site in the target/backbone DNA junction. In this disclosure, it is preferred that self-ligation of the backbone yields a first restriction enzyme site and ligation of the backbone to target DNA does not yield the site. A preferred first restriction enzyme site is an enzyme that allows for the most sequence variation in the ligation junction. As the sequence of the backbone has one part, and preferably a half, of the recognition sequence of the first restriction enzyme site, the variation comes from the sequence of the target end. In case the first restriction enzyme site is an EcoRI site the backbone sequence that codes for the first restriction enzyme site has a 5' end with the sequence 5'-AATTC. The junction with target DNA can have 1 of four different sequences depending on the base of the nucleotide that flanks the overhang in the target DNA. Only when the target sequence has an end with the sequence 5'-AATTC . . . is the ligation junction with the backbone digestible with EcoRI. Junctions with other sequences are not digestible with EcoRI. Variation in junctions is improved by selecting enzymes that create small or no overhangs and by selecting enzymes that require more specific bases in the recognition site. The first restriction enzyme site preferably comprises 6 and more preferably 8 and preferably more bases. The enzyme that cuts the first restriction enzyme site is therefore preferably at least a 6 cutter, more preferably at least a 7 cutter, more preferably an 8 cutter. The number indicates the number of bases in the recognition site of the enzyme. For example, EcoRI is a 6-cutter; AluI recognizing AGCT is a 4-cutter. There are also 5-cutters (e.g., AvaII), 7-cutters (e.g., BbvCI), 8-cutters (e.g., NotI), and even other restriction enzymes. Together with the preference of a small or no overhang, this ensures a high potential for sequence variation in the ligation junction and which lowers the chance that the junction of a target sequence with a backbone sequence is a first restriction enzyme site. First restriction enzymes with more nucleotides in the recognition site are preferred also because such enzymes can allow for bigger target nucleic acid inserts. The methods are suitable for a large variety of target nucleic acid sources. Methods of the disclosure can be performed with two or more backbones that have different first restriction enzyme sites. In this way more target molecules can be captured into DNA circles. In case a target DNA has two first restriction enzyme sites that are close together, the intervening sequence can efficiently be sequenced, for instance, by capturing it with the backbone with the other first restriction enzyme site. The reference to first, in the context of the restriction site, refers to the position of the (halves of the) site on the backbone. Restriction enzyme recognition sites at other positions in the backbone will be referred to as second, third etc. restriction enzyme recognition sites.

Preferred first restriction enzyme recognition sites are sites for the restriction enzymes SrfI (GGGC|GCCC); PmeI (GTTT|AAAC) and SweI (ATTT|AAAT). A particularly preferred first restriction enzyme site is the site for the restriction enzyme SrfI.

A 5' end of a backbone comprises a part of the first restriction enzyme recognition site at the extreme end. It can but does not need to contain additional nucleotides on the inside. The number of nucleotides of the end may vary. A 5' end typically has between 2-15 nucleotides, preferably 2-10, preferably 2-8, more preferably 2, 3, 4, 5, 6, 7 or 8 nucleotides. In some embodiments the 5' end is 3 or 4 nucleotides.

A 3' end of a backbone comprises a part of the first restriction enzyme recognition site at the extreme end. It can but does not need to contain additional nucleotides on the inside. The number of nucleotides of the end may vary. A 3' end typically has between 2-15 nucleotides, preferably 2-10, preferably 2-8, more preferably 2, 3, 4, 5, 6, 7 or 8 nucleotides. In some embodiments the 3' end is 3 or 4 nucleotides.

5' and 3' ends of target DNA are preferably blunt ends. They can also be sticky ends that can be ligated together if self-ligation is not otherwise prevented. The 5' end and 3' ends of target DNA are preferably provided in dephosphorylated form to prevent self-ligation. The 5' and 3' ends of target DNA can also be sticky ends that cannot be ligated together, such as adenine overhangs added by terminal transferase enzymes.

Ligation is preferably performed in the presence of a ligase and a restriction enzyme (first restriction enzyme) that cuts the first restriction enzyme site. Ligation of the ends of a backbone to the ends of a target DNA creates double stranded DNA circle. Self-ligation of backbones is often not prevented in methods of the disclosure. In the presence of a ligase, ligation of the two ends of the backbone to each other or to ends of other backbones can hamper the capture of target nucleic acid by the backbones. Ligation of backbones ends is counteracted by the present of the first restriction enzyme. As such ligations typically (re)create the first restriction enzyme site, the backbone is linearized and/or deconcatemerized. The ligation reaction is performed using buffer conditions that support both efficient ligation and efficient cutting by first restriction enzyme.

Methods of the disclosure are particularly suited to produce DNA circles with one backbone and one target nucleic acid.

In embodiments of the disclosure, linear DNA, if any, is preferably removed prior to the rolling circle amplification. Performing a rolling circle amplification after removal of linear DNA typically produces more high molecular weight concatemers of backbone and target DNA.

Methods include subjecting DNA circles that are produced in the ligation reaction to rolling circle amplification (RCA). Rolling circle amplification produces an ordered array of copies of at least two of the DNA circles. Rolling circle amplification produces DNA molecules of high molecular weight, which is suited for sequencing, particularly for long read sequencing.

Rolling circle amplification has recently been reviewed by Mohsen and Kool (2016) Acc Chem Res. Vol 49(11): pp 2540-2550; Published online 2016 Oct. 24. doi: 10.1021/acs.accounts.6b00417. The terms rolling circle amplification and rolling circle replication are sometimes used interchangeably in the art. In other instances, rolling circle replication is used to refer to replication of naturally occurring plasmid and virus genomes. The terms refer to a similar underlying principle, i.e., the repeated copying of the same circular DNA producing a longer nucleic acid molecule with an ordered array of backbone-target nucleic acid copies. Present techniques for rolling circle amplification enable the production of large arrays containing many copies of the produced DNA circles. Concatemers can have 2 or more copies, preferably 4 or more copies of the produced circles.

Rolling circle amplification is performed by a polymerase and requires the usual priming sequence to generate the start. Particular polymerases with high processivity are available to produce concatemers of considerable length. Polymerases with high processivity are polymerases that can polymerize a thousand nucleotides or more without dissociating from the DNA template. They can preferably polymerize a two, three, four thousand nucleotides or more without dissociating from the DNA template. Polymerases with high processivity are among others discussed in Kelman et al; 1998: Structure Vol 6; pp 121-125. Rolling circle amplification can yield very high molecular weight concatemers using polymerases with high processivity and strand-displacement capacity such as phi29 polymerase. This polymerase can polymerize 10 kb or more. High processivity polymerases are therefore preferably polymerases that polymerize 10 kb or more without dissociating form the DNA template (Blanco et al; 1999. J. Biol. Chem. 264 (15): 8935-40). The polymerization can be started on a nick in the double strand DNA or the DNA can be melted and annealed in the presence of one or more suitable primers. Examples of suitable primers are random hexamer primers, one or more backbone specific primers, one or more target nucleic acid specific primers or a combination thereof. Random primers are typically preferred when target nucleic acid sequences are not known or when a variety of target nucleic acid sequences are to be sequenced. One or more specific primers can be used to sequence specific target nucleic acids of which the basis sequence is known. A variant is one or more primers that are specific for the backbone. Such primers can be used in different situations, such as but not limited to high throughput systems with optimized backbones.

An advantage of having double-stranded circular DNA is that one of the strands can be used as a template for the rolling circle amplification. For example, by using a strand specific primer to initiate the RCA reaction. Data analysis of Oxford nanopore sequencing results allowed to determine the base-calling and variant calling accuracy for each of the strands separately. In particular, it was noticed that C and A bases are often difficult to distinguish due to the similar intensity of their raw current signal. However the current signal coming from a T is substantially different from all the other bases and easy to be correctly classified. For example, if an A is expected to be mutated in the forward strand, sequencing of the reverse strand would lead to much cleaner results since the A in the forward strand could be miss called as a G. Thus, specific enrichment of the reverse strand would be advantageous in such a scenario. Thus, in a preferred embodiment, the rolling circle initiation primer is a strand selective primer.

Further optimizations in obtaining strand-specific sequences may involve the (additional) use of real-time selective sequencing methods, such as those described in prior work (PMID: 27454285) (Loose et al. 2016. Nature methods. Real-time selective sequencing using nanopore technology).

Backbones are preferably 20-1000 nucleotides long, preferably 20-800, preferably 50-800; more preferably 100-600 nucleotides, preferably 200-600 nucleotides. Target nucleic acid is preferably 40-15000 nucleotides long depending on the application.

DNA that circulates free or that is associated to cellular particles in the blood or other bodily fluid samples is typically smaller than 400 nucleotides. Target nucleic acid molecules of such lengths are particularly suited in methods of the disclosure. Other samples with relatively small nucleic acid molecules are some types of forensic samples, fossil samples, samples of nucleic acid isolated from environments that are inherently hostile to nucleic acid molecule integrity such as stool samples, surface water samples, and other samples rich in microbial organisms. For small target DNAs (smaller than 100 nucleotides) it is preferred to use the larger backbones as disclosed herein. Target nucleic acid can also be double-stranded circulating tumor DNA (ctDNA) or cell free DNA (cfDNA) present in liquid biopsies including but not limited to blood, saliva, pleural fluid or ascites fluid. Target nucleic acid can also be double-stranded or single-stranded cDNA derived from messengerRNA microRNA, CRISPR RNA, non-coding RNA, viral RNA, or other sources of RNA. Target nucleic acid can also be double-stranded DNA derived from genomic DNA, PCR products, plasmid DNA, viral DNA, or other sources of double-stranded DNA. The means and methods of the disclosure are particularly suited to capture small DNA. Preferably, 400 base pairs or smaller target DNA is captured in a backbone of the disclosure. This captured DNA is also called an "insert" or "target" DNA. Target DNA is preferably 400 base pairs or less, more preferably 300 base pairs or less, more preferably 200 base pairs or less, more preferably 150 or less. The lower limit of the target DNA is preferably 20 base pairs, more preferably 30 base pairs, more preferably 40 base pairs and more preferably 50 base pairs. Any lower limit can be combined with any upper limit.

The size of DNA fragments is given in nucleotides here. This refers of course to the number in one strand. The size could also be given in base pairs for double stranded DNA. So a DNA that is 400 nucleotides is 400 base pairs long.

Produced concatemers can be sequenced with a variety of different methods. Of these the long read sequencing methods are preferred. Various long read sequencing methods are available to the skilled person. They all share the feature that molecules of more than 200 nucleotides are produced in the sequencing reactions. Typically more than 500 nucleotides and even several thousands of nucleotides long. Two presently available platforms for long read, real-time, single-molecule sequencing are the Pacific Biosciences systems (the RSII and the Sequel) and the Oxford Nanopore systems (MK1 MinION, GridION and PromethION). These allow reads in excess of 55 kb and longer (Goodwin et al 2016; doi: 10.1038/nrg.2016.49). Long-read systems are preferably single-molecule real-time sequencing systems. Single molecule systems do not rely on a clonal population of amplified DNA fragments to generate detectable signals. These systems fix the sequence determining protein at a specific location and allow the strand of nucleic acid to progress through the protein. The present Pacific Biosciences systems use a polymerase whereas the Oxford Nanopore systems presently use a membrane channel protein. In a preferred embodiment, the sequencing method is a single-molecule real-time (SMRT) sequencing method. Produced concatemers have an ordered array of copies of at least one of the DNA circles, preferably at least two, three, four or preferably at least 5 of the DNA circles.

Figure 1:
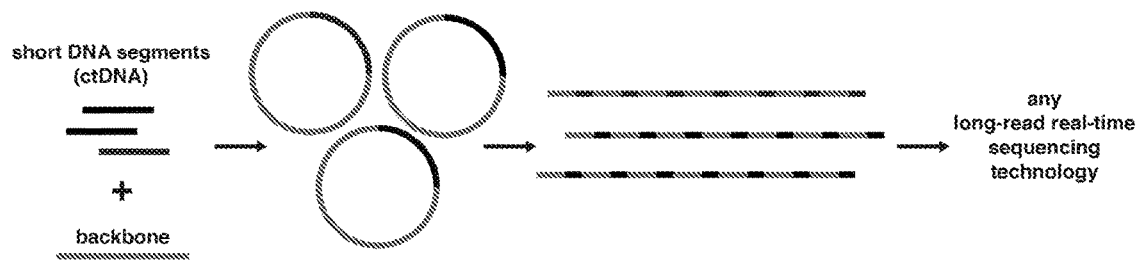
FIG. 1. A) Schematic representation of a method of capturing small nucleic acid molecules and producing concatemers by using a backbone and rolling circle amplification. B) Schematic representation of a sequencing reaction using short reads and without a backbone and long read sequencing using backbones.
Figure 1:
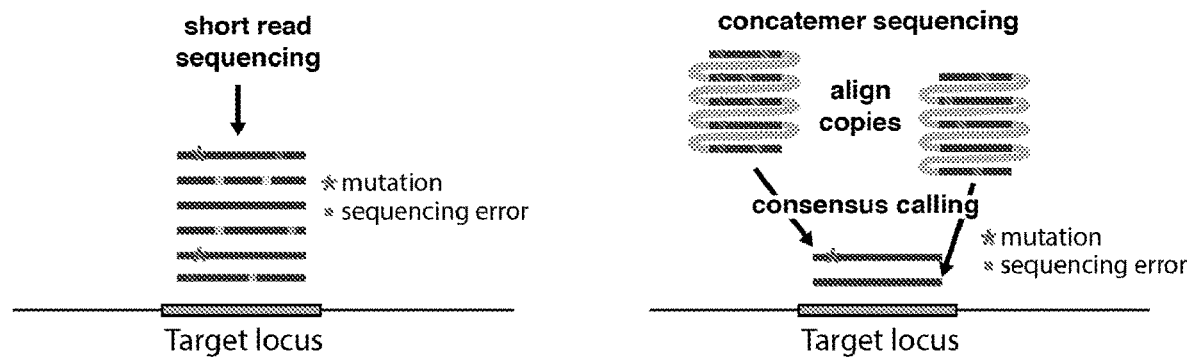

In some embodiments of the disclosure, backbones have identifiers. Such identifiers are also referred to as barcodes. The identifiers or barcodes are stretches of nucleic acid of which the sequence can vary between backbones. Barcoding can be used to group sequencing results of particular DNA circles. A barcode can identify a DNA circle. The barcode can be used to group sequencing results of fragments of the ordered array of concatemers produced by RCA of a DNA circle. The barcode as such can be used to identify particular DNA circles. Methods using backbones with barcodes typically have one or more collections of backbones wherein backbones in a collection have unique barcodes in otherwise similar or identical backbones. Two or more collections of backbones can be used, for instance, to accommodate the different first restriction enzyme sites mentioned herein above, or to identify sequencing results of different samples. Barcodes between collections can be identical because sequence differences in other parts of the backbones identify the collections. Backbone collections may comprise more than one copy of a particular barcode containing backbone. The combination of a barcode with a particular overall target sequence can also positively identify a nucleic acid as being derived from a particular DNA circle, for instance, when the target nucleic acid is complex and/or the number of identical barcodes is low in a collection of backbones. Sequencing results of a group of sequences of a DNA circle can be used to filter out errors, such as amplification or polymerase errors. This is exemplified schematically in FIGS. 1A and 1B. Backbones used in a method as disclosed herein preferably comprise at least two backbones with unique identifiers.

The DNA circles are produced in the ligation step. Longer molecules are typically more efficiently circularized. Flexible molecules are more easily circularized than rigid molecules. Small target nucleic acid (20-200 nucleotides) can be captured more efficiently by larger backbones. For small target nucleic acids backbone preferably have 200 or more nucleotides, preferably 300 or more, more preferably 400 or more nucleotides, preferably between 450-650 nucleotides. The smaller backbones typically allow for more concatemers per DNA circle. The average length of the target nucleic acid and the length of the backbone(s) in a DNA circle is preferably 90-16,000 nucleotides, preferably 200-12,000 nucleotides; preferably 300-8,000 nucleotides, preferably 400-4,000 nucleotides, preferably 500-2,000 nucleotides. The average length of target nucleic acid plus backbone nucleic acid is preferably about 1.000 nucleotides.

A backbone DNA molecule preferably comprises the sequence of:

>BB1 (199 bp)
(SEQ ID NO: 5)
GGGCATGCACAGATGTACACGTACGATCATGTACGTCACGCGAGTGCACGTCGT

CATAGCTGTCGAGTACTGTACTGACTGTCTCGAGCCTCAGCGAGTATTTAAATCTACGT

AGAGTACGACTGCGCAGATGTGATCAGTGACTACGTGACACTGTACATCAGCACGATCG

ATGACTAGATGCTGCATGACATAGCCC;

>BB2 (259 bp)
(SEQ ID NO: 6)
GGGCATGCACAGATGTACACGTACGATCATGTACGTCACGCGAGTGCACGTCGT

CATAGCTGTCGAGTACTGTACTGACTGTCTCGAGCCTCAGCGAGTATTTAAATCTACGT

CACCGGGTCTTCGAGAAGACCTGTTTAGAGTACGACTGCAAATGGCTCTAGAGGTACCC

GTTACATAACTTACGCAGATGTGATCAGTGACTACGTGACACTGTACATCAGCACGATC

GATGACTAGATGCTGCATGACATAGCCC;

>BB2_100 (341)
(SEQ ID NO: 7)
GGGCATGCACAGATGTACACGTACGATCATGTACGTCACGCGAGTGCACGTCGTCATAG

CTGTCGAGTACTGTACTGACTGTCTCGAGCCTCAGCGAGTATTTAAATCTACGTCACCA

TATATATGGATATATATATGGATATATATATATATGGATATATGGATATATATATATAT

ATATGGATATGTATGGATATATATATATGGATATGGATGTTTAGAGTACGACTGCAA

ATGGCTCTAGAGGTACCCGTTACATAACTTACGCAGATGTGATCAGTGACTACGTGACA

CTGTACATCAGCACGATCGATGACTAGATGCTGCATGACATAGCCC;
or

>BBpX2 (557 bp)
(SEQ ID NO: 8)
GGGCATGCACAGATGTACACGAACGCCAGCAACGCGGCCTTTTTACGGTTCCTGGCCTT

TTGCTGGCCTTTTGCTCACATGTGAGGGCCTATTTCCCATGATTCCTTCATATTTGCAT

ATACGATACAAGGCTGTTAGAGAGATAATTGGAATTAATTTGACTGTAAACACAAAGAT

ATTAGTACAAAATACGTGACGTAGAAAGTAATAATTTCTTGGGTAGTTTGCAGTTTTAA

AATTATGTTTTAAAATGGACTATCATATGCTTACCGTAACTTGAAAGTATTTCGATTTC

TTGGCTTTATATATCTTGTGGAAAGGACGAAACACCGGGTCTTCGAGAAGACCTGTTTT

AGAGCTAGAAATAGCAAGTTAAAATAAGGCTAGTCCGTTATCAACTTGAAAAAGTGGCA

CCGAGTCGGTGCTTTTTTGTTTTAGAGCTAGAAATAGCAAGTTAAAATAAGGCTAGTCC

GTTTTTAGCGCGTGCGCCAATTCTGCAGACAAATGGCTCTAGAGGTACCCGTTACATAA

CTTATAGATGCTGCATGACATAGCCC.

>BB100_1 (143 bp)
(SEQ ID NO: 9)
GGGCATGCACAGATGTACACGATTCCCAACACACCGTGCGGGCCATCGACCTATGCATA

CCGTACATATCATATATAAATCACATAATTTATTATACGTATGTCGCGCGGGTGGCTGT

GGGTAGATGCTGCATGACATAGCCC

>BB100_2 (143 bp)
(SEQ ID NO: 10)
GGGCATGCACAGATGTACACGCACTACATGCCAATGCCCAAGCAGTGCGCATATCACGT

ATCATATCTAATATATTATAATATTATGATAATGAGTATTTATTTAATTTGTTTGTGTG

AGGTAGATGCTGCATGACATAGCCC

-continued

>BB100_3 (143 bp)
(SEQ ID NO: 11)
GGGCATGCACAGATGTACACGCATTGGCCGTCTGTGCTGTCCATGGATCGTCTGATTGA

TATGATATCATATATTATAATTATACAGTAAGGTGATTGGGTATTGAGGGTTGTGTGGT

TGGTAGATGCTGCATGACATAGCCC

>BB100_4 (145 bp)
(SEQ ID NO: 12)
GGGCATGCACAGATGTACACGGTAGACATGCGAAGCGTGCGATGACAATCGATGTGGAC

ATCATGCATATATATGTTGTATAATTAAACAAATATGTGTAGTGTGTGAGGTGGGTGTA

GGAAGTAGATGCTGCATGACATAGCCC

>BB100_5 (143 bp)
(SEQ ID NO: 13)
GGGCATGCACAGATGTACACGTTGTCATGGGAATTTGTGGTTATGAAATGAGTATGCGA

CGAATATGTATACATATATATTAAATTATAGAGTGATGTATGAGTTTGTGATGTGTGGT

GTATAGATGCTGCATGACATAGCCC

>BB200_1 (243 bp)
(SEQ ID NO: 14)
GGGCATGCACAGATGTACACGGCGGCGCAAGATGATGTGCCGAACCTGACATGGCATCG

ACTGGTATGGATCAATACTGATGCGATATCGATACCGGATAAATCATATATGCATAATA

TCACATTATATTAATTATAATACATCGGCGTACATATACACGTACGCATCATTTCACTA

TCTATCGGTACTATACGTAGTGCCGGTCTGTTGGCCGGGCGACATAGATGCTGCATGAC

ATAGCCC

>BB200_2 (244 bp)
(SEQ ID NO: 15)
GGGCATGCACAGATGTACACGTGACGCAACGATGATGTTAGCTATTTGTTCAATGACAA

ATCTGGTATGATCAATACCGATGCGATATTGATATCTGATAACTCATATATGTAGAATA

TCACATTATATTTATTATAATACATCGTCGAACATATACACAATGCATCTTATCTATAC

GTATCGGGATAGCGTTGGCATAGCACTGGATGGCATGACCCTCATTAGATGCTGCATGA

CATAGCCC

>BB200_3 (244 bp)
(SEQ ID NO: 16)
GGGCATGCACAGATGTACACGAGACCGCAAGATGATGTTCATTCTTGAACATGAGATCG

GATGGGTATGGATCAATACCGATGCGATATGATAACTGATAAATCATATATCTATAATA

TCACATTATATTAATTATAATACAGGATCGTTACATGCATACACAATGTATACTATACG

TATTCGGTAGTTAGTGTACGGTCGGAATGGAGGTGGTGGCGGTGATAGATGCTGCATGA

CATAGCCC

>BB200_4 (243 bp)
(SEQ ID NO: 17)
GGGCATGCACAGATGTACACGAATCCCGAAGATGTTGTCCATTCATTGAATATGAGATC

TCATGGTATGATCAATATCGGATGCGATATTGATACTGATAAATCATATATGCATAATC

TCACATTATATTTATTATAATAAATCATCGTAGATATACACAATGTGAATTGTATACAA

TGGATAGTATAACTATCCAATTTCTTTGAGCATTGGCCTTGGTGTAGATGCTGCATGAC

ATAGCCC

>BB200_5 (243 bp)
(SEQ ID NO: 18)
GGGCATGCACAGATGTACACGAATCCGTGAGATGACTATCTTATTTGTGACATTCATCG

ATCTGGATATGATCAATACCATGCGATATTGATTACTGATAAATCATATATGTAGAATA

TCACATTATATTAATTATAATAAATCGTCGTACATATACATCCACAATTAGCTATGTAT

```
ACTATCTATAGAGATGGTGCATCATCGTACTCCACCATTCCCACTAGATGCTGCATGAC

ATAGCCC

>BB300_1 (348 bp)
                                                    (SEQ ID NO: 19)
GGGCATGCACAGATGTACACGCATAAGACCACAGGGTGCAAATCTGGATTGCGGCATGG

ATGATTCATCATCGTGGCATATTCGCTATGGATATATCCATCATAATACATTGATACGT

CATGCGTATAATCGCATTATATGTCGATATTGGTCATAGGGATACATCCGTGTATACTA

TCGTATATGCGTGCAATGTAGCCATGTTAATCATGCTATAACCATAACATAAATATAAT

ATATACAGATGGTGTATCTCTACTTATGTATGCTTGTATAGTAATGTCGATACTGATGG

GTCTCCGGCCCACTACACCACCTGGCCGCTCTAGATGCTGCATGACATAGCCC

>BB300_2 (343 bp)
                                                    (SEQ ID NO: 20)
GGGCATGCACAGATGTACACGGGCAATCCGCCAGGGTTCAAATATGGATATGTGATGAT

CGATTCAACATGCACATATGCACGATATCATATATTACTCCAGATGTCATCATCGTCGT

GCGTATATGAGATATGTATTTATGCATATAATCCACCATACATGGTAGCGATATTATAG

TGCGATTATGTGTATATGACTATCATGGCTATTGTTAATATATAAATCATAACCATACC

ACTTCCACGCCTGGTATGGCGTATAGTATAGAGATATTGTGTGATGCCCTATGTCGACC

ATGATGTGCCGTTGTACTGCCAATCCTAGATGCTGCATGACATAGCCC

>BB300_3 (344 bp)
                                                    (SEQ ID NO: 21)
GGGCATGCACAGATGTACACGTATCCATGCAGCTTATTGTAACTAGCGCATGCACGTGG

TGATTCATCACATCTATATATACGATATGATATATTACACATATTTGCATAGTATCATC

CGGTGTGATATCATCCGATATGCTCATACTTATTCATTGGTAGCATTGCATTGATGGAT

CAATAGTTATTATGACATCATGGCATGTACAATTATAAATAATACAACATACATAAATA

TACTATACACATCGTGTATGTGTTATACAGATCTGTGTGATGTATGATAATGTAATGGC

GTCGAACACCACAAGGCAGTCCTATAATAGATGCTGCATGACATAGCCC

>BB300_4 (344 bp)
                                                    (SEQ ID NO: 22)
GGGCATGCACAGATGTACACGGTCCATTACAATCGAATCTATATCCCAATGTGTATCGA

TTATCACCACAATGACATAATACGATATCATATATTACTCCATATGCCTTACGTCAGAT

CGTTATATGAGATATGTATTCATGCATATGATATCCCACAGTACACGTCGTCTAATGCC

ATCATGAATGTATGACATATCTAGTCGATTATACATAATATAACATACCAATATAACAA

TATCTATACACATTTGATGGCGTATAGTATAAAGATATTGTGGCAATGCCCATACACCA

CTGACTGTCGCCGATCATTCCTACCACTAGATGCTGCATGACATAGCCC

>BB300_5 (344 bp)
                                                    (SEQ ID NO: 23)
GGGCATGCACAGATGTACACGACCGACCGTGAAAGTGATTCAGAATGATGTGCATGAAT

GTTATCATGACATGATTTATGATGCACTGATATATGCATATTATAATATTGTACAATGT

CGTATATACGACATATCTATACTATGAATTATGGCATCATGGACAATAGATGGTAAGGT

ATAGTACGATCTATATAGCATGTTGAAATGGGATATAAATTATCATAAACATACATACT

TAACTAATATCAAGATGATATGTGTATGACATCAGAATGATAGTAGTAATGAGTATTGT

CAGATGTATGTACGAATATCACACGATTAGATGCTGCATGACATAGCCC
```

A backbone DNA molecule most preferably comprises the sequence of:

```
>BB200_4 (243 bp)
                                          (SEQ ID NO: 17)
GGGCATGCACAGATGTACACGAATCCCGAAGATGTTGTCCATTCATTGA

ATATGAGATCTCATGGTATGATCAATATCGGATGCGATATTGATACTGA

TAAATCATATATGCATAATCTCACATTATATTTATTATAATAAATCATC

GTAGATATACACAATGTGAATTGTATACAATGGATAGTATAACTATCCA

ATTTCTTTGAGCATTGGCCTTGGTGTAGATGCTGCATGACATAGCCC
```

Flexibility of backbones of a fixed length can be modulated by tailoring the sequence of the backbone. Different DNA molecules have different flexibilities depending on the particular sequence of the molecules. Different sequences can be provided by choosing different first restriction enzyme sites, different barcode sequences and different sequences for other elements in the backbone. The flexibility is preferably adjusted by tailoring the sequence of a dedicated part of the backbone sequence. Such a dedicated part is further referred to as "the linker". The linker preferably comprises 20-900 nucleotides, preferably 25-900 nucleotides, preferably 30-900, preferably 30-800, preferably 50-700; preferably 100-600, preferably 150-500 nucleotides. A linker can be one consecutive sequence or divided into two, three, four or more consecutive sequences in the backbone. A linker is preferably one consecutive sequence or divided into two, three, four consecutive sequences, preferably one, two or three, preferably one or two, and more preferably one consecutive sequence in the backbone.

The free energy values of each base-pair (Breslauer et al. 1986) and the deviation of the twist angle (degrees) (Sarai et al. 1989) can be used to compute the flexibility of any given DNA sequence. An example of such a calculation is:

Flexibility Calculation

A python implementation of the TwistFlex algorithm (margalit.huji.ac.il/TwistFlex/) (Menconi et al. 2015) can be used to compute DNA flexibility at the twist angle of the input sequence. The flexibility of each individual dinucleotide is calculated based on the following table of angular degrees:

|   | A    | T    | C    | G    |
|---|------|------|------|------|
| A | 7.6  | 10.9 | 8.8  | 12.5 |
| T | 14.6 | 7.2  | 11.1 | 8.8  |
| C | 8.2  | 8.9  | 7.2  | 10.9 |
| G | 25   | 8.2  | 14.6 | 7.6  |

Subsequently, the mean flexibility of the entire sequence is considered for the selection in the evolutionary algorithm for backbone optimization. The mean flexibility of a DNA sequence is calculated as the sum of all dinucleotide angular degrees divided by the total number of dinucleotides. The flexibility score for suitable backbones is 10 or more, preferably 11 or more, preferably 12 or more, preferably 12.5 or more (dinucleotide angular degrees/dinucleotides) in the backbone. Flexibilities of more than 14 are usually not required.

Entropy Calculation for Determining Sequence Complexity

The Shannon entropy of a string is defined as the minimum average number of bits per symbol required for encoding the string. The formula to compute the Shannon entropy is:

$$H = -\sum_i p_i \log_b p_i$$

where $p_i$ is the probability of character number i appearing in the sequence.

The calculation can also be performed through: shannon-entropy.netmark.pl/

The above formula was implemented with the following python code:

```
def quick_entropy(sequence):
    alphabet = set(sequence) # list of symbols in the sequence
    # Frequency of each symbol in the sequence
    frequencies = [ ]
    for symbol in alphabet:
        frequencies.append(sequence.count(symbol) /
            len(sequence))
    # Shannon entropy as in
en.wiktionary.org/wiki/Shannon_entropy
    ent = 0.0
    for freq in frequencies:
        ent -= freq * math.log(freq, 2)
    return ent
```

Preferred backbones have a Shannon entropy value of 1.5 Sh or higher. Preferably 1.5 or higher, preferably 2.5 or higher, more preferably 3.5 or higher.

Self-Complementarity

Backbone core sequences preferably do not have 8 or more consecutive bases self-complementary in the same strand. The exception is the intentional insertion of one or more restriction enzyme sites or one or more other functional sequences. Such sequences can occasionally introduce self-complementary bases in the same strand. If possible more than 8 of such bases are avoided, but they can be tolerated in functional backbones. Nevertheless, in designing new backbones such sequences are preferably avoided if possible. The same is true for the kmers discussed herein below.

Absence of Repeated Motifs (Kmers)

Backbone core sequences preferably do not have motifs of 6 bases repeated more than twice in the sequence.

The flexibility of the backbone and the Shannon index of a backbone can be modulated by including a linker in the backbone. The influence of a particular sequence of the linker on the flexibility and complexity scores of the backbone can be easily be calculated.

A linker preferably has one or more of the following features: (i) the overall complexity of the linker sequence is preferably high. The above mentioned Shannon entropy formula is a method to determine a value for the complexity of a given sequence; (ii) duplications of DNA motifs longer than 5 bases are preferably not present more than twice in the linker sequence, preferably no more than once. In a preferred embodiment, the linker does not comprise a duplication of a DNA motif longer than 5 bases (i.e., the linker sequence does not contain a repeated motif where the motif is more than 6 consecutive bases); (iii) a linker preferably does not comprise more than two, preferably not more than one and preferably no self-complementary sequence of more than 6 nucleotides (an inverted repeat) separated by less than 10 nucleotides. The mentioned criteria aid in avoiding, in general, the presence of a complex secondary structure in a single stranded version of the linker. The likelihood and the strength of the secondary structure can also be calculated by other means.

A backbone preferably comprises a GC content of 30-60%; preferably 40-60%; preferably 40-50%, preferably 45-55%.

A backbone preferably has one or more of the following features. The first restriction enzyme site is preferably for a restriction enzyme that produces blunt ends. It has been observed that this improves the capture of target nucleic acid. The backbone preferably comprises a recognition site for a DNA nicking enzyme that is used to generate the priming site for rolling circle amplification. Additional restriction enzyme recognition sites can be used to perform sequential ligation of multiple short DNA molecules into one circular DNA. The backbone preferably comprises a molecular identifier that enables the discrimination of original captured nucleic acids and their subsequent sequencing reads.

A method of the disclosure can be used for the ordered capture of two or more target nucleic acids per backbone. A single capture step can, on occasion capture two target nucleic acid molecules at the same time. The chance of this happening is intentionally low because of the measures that are taken to prevent self-ligation. The ordered capture of two or more target nucleic acids can be a desired feature. Additional restriction enzyme sites can be incorporated into the backbone. Once a first target nucleic acid is captured, the method can be repeated by adding a restriction enzyme that cuts the additional restriction enzyme site. The DNA circle is cut and linearized by the second restriction enzyme and ready to be ligated to the target nucleic acid. If the second restriction enzyme produces the same type of ends as the first restriction enzyme (for example, blunt ends), the reaction can be continued to capture target nucleic acid not captured in the first iteration of the method. Alternatively, the DNA circles can be purified (for instance, by removing linear DNA) and new target nucleic acid with ends that are ligation compatible to the ends of the backbone produced by the second restriction enzyme can be added. This step can, of course, be repeated for the ordered capture a third, a fourth and so forth target nucleic acid by adding further restriction enzyme sites to the backbone. When more than one target nucleic acid is to be captured it is preferred that the second and first restriction enzymes sites are sites for enzymes that cut infrequently. Such enzymes are preferably 8-cutters or more. The enzymes are preferably blunt end producing enzymes. This ordered capture allows the simultaneous sequencing of more than one target nucleic acid. The different target nucleic acids can be identified on the basis of their location in the backbone, i.e., on the basis of the flanking backbone sequences into which they are inserted.

Additionally, the backbones serve as a control sequence during data analysis. Based on the backbone sequence reads, the error-rate of each sequencing read can be inferred, enabling accurate estimation of the likelihood of genetic variations within captured nucleic acid sequences.

Side products can be produced in a method of the disclosure. The amount of single backbone, single target DNA containing DNA circles is influenced, for instance, by the backbone/sample molar ratio: ratio, which should promote the formation of molecules with backbone and insert, rather than unwanted side products (FIG. 2), such as (i) linear DNA formed by random concatemerization of backbone and sample DNA, (ii) circular DNAs containing only backbone or only sample DNA, (iii) circular DNA containing excess of backbones or sample DNAs.

In embodiments of the disclosure, the molar ratio of backbone molecules to target nucleic acid molecules preferably range from 1:10 to 10:1. Preferably a ratio range of 1:5 to 5:1 is maintained, preferably a ratio of 1:2 to 2:1 is maintained. An average a ratio of 1:1 is preferred.

The methods as described herein including the rolling circle amplification are preferably performed without switching containers. Produced concatemers can be sequenced in the same container or a different container.

A method of the disclosure preferably produces concatemers as long (>10 Kb) linear dsDNA formed by multiple units consisting of target nucleic-acid-backbone copies. The concatemerization/multimerization of such a unit is advantageous to discriminate the detection of a real genetic variation from a sequencing error. In fact, in the case of rare genetic variations, that occur in less than 1% frequency within a pool of DNA molecules, direct sequencing, e.g., short-read sequencing cannot be applied anymore, because the sequencing error rate is higher than the mutation frequency. Using a method as described herein, the same rare sequence (genetic variation) is represented multiple times in long concatemers, which provides high confidence about mutation presence, even if the mutation frequency is low in the original pool of nucleic acid molecules.

A backbone comprises a 3' sequence coding for one part of a first restriction enzyme recognition site (restriction enzyme site) and a 5' sequence coding for the other the other part of the first restriction site. A backbone may contain further elements. Such as one or more of (i) one or more sites that allow nicking of the double-stranded backbone sequence; (ii) one or more Type1 or Type2 restriction sites; (iii) A secondary cloning site; (iv) a flexible DNA stretch (linker) that enables efficient circularization (bending) of the backbone molecule; and (v) a unique molecular barcode sequence to tag each individual backbone molecule.

A backbone preferably has 5'-phosphorylation at both ends of the backbone molecule.

The disclosure also provides a collection of linear DNA molecules (backbones) of a length of 20-1000 nucleotides that comprise 5' ends that comprise a part of a first restriction enzyme recognition site at the extreme end and 3' ends that comprise the other part of a first restriction enzyme recognition site at the extreme end, and which 5' and 3' ends are ligation compatible with each other and form a restriction enzyme recognition (first restriction enzyme) site when self-ligated and wherein each of the backbones comprises:
 a linker;
 an identifier sequence that differs from the sequence of identifiers of other backbones in the collection (barcode); and
 optionally a restriction site for a nicking enzyme.

The backbones are backbones that are preferred in a method as described herein. The first and the second part of the first restriction site together form a complete recognition site for the first restriction site and are in positions on the molecule that allows operable linkage of the two parts to form the first restriction site. Operable linkage in this context refers to availability for cutting by the first restriction enzyme. The backbones preferably further comprise a second restriction site, which is a type I or type II restriction enzyme site. The backbones preferably further comprise a restriction enzyme site for a type II restriction enzyme that can create non-palindromic overhangs (Golden-Gate cloning site). The linker is preferably a linker as described herein above. The backbones preferably comprise a nucleic acid molecule (captured nucleic acid molecule) in the first restriction site. The backbones preferably comprise a library of captured nucleic acid molecules.

Further provided is a kit comprising a backbone as described herein. The kit preferably comprises a collection of backbone molecules as described herein. The preferably further comprises a polymerase with high processivity and optionally one or more polymerization primers. The kit preferably further comprises a ligase and the first restriction enzyme; and/or the target site specific recombination enzyme. The kit preferably further comprises a DNA exonuclease. The latter enzyme is suitable for removing linear DNA prior to producing concatemers of the DNA circles.

In one aspect, the disclosure provides a method for determining the sequence of a collection of nucleic acid molecules the method comprising
providing double stranded target DNA molecules that have 5' and 3' ends with a protruding adenine residue at the 3"-end of both strands of the DNA molecules;
providing a collection of double stranded backbone DNA molecules that
comprise 5' and 3' ends that are ligation compatible with the 5' and 3' ends of the target DNA;
the method further comprising
ligating the target DNA to the backbones in the presence of a ligase, thereby producing DNA circles comprising a backbone and a target DNA molecule;
optionally removing linear DNA;
producing concatemers comprising an ordered array of copies of at least two of the DNA circles through rolling circle amplification; and
sequencing the concatemers.

Ends that are ligation compatible with a protruding 3' adenine are ends that have a 5' protruding thymidine base or analogue thereof. The method is different from the methods described herein above in that inter- or intra-target molecule ligation is inherently inhibited as all ends have a '-protruding adenine base. Self-ligation of target nucleic acid or ligation of one end to another target nucleic molecule is thus inherently not possible. A protruding base or bases are nucleotides that are at the end of a nucleic acid molecule and that are not base paired with a base on an opposing strand. There is no opposing base for the protruding base. Such protrusions are also referred to as sticky ends, or cohesive ends. The same is true for the backbones. They are inherently prevented from self-ligation. In this embodiment, the backbones do not have to have parts of a first restriction enzyme site at the extreme end. The ends thus not ligate to create a first restriction enzyme site. Thus, the ligation does not have to be performed in the presence of the first restriction enzyme. The remainder of the steps and the definitions can be the same as described elsewhere herein.

Further provided is a method for determining the sequence of a collection of nucleic acid molecules comprising
providing double stranded target DNA molecules that have a recombinase recognition site specific for a target site specific recombinase at the 5' and the 3' ends;
providing a backbone comprising the recognition sites separated by DNA comprising a linker;
incubating the target DNA molecules with the backbones in the presence of the target site specific recombinase, preferably a Cre recombinase, a FLP recombinase or a bacteriophage lambda integrase, thereby producing DNA circles comprising a backbone and a target DNA molecule;
optionally removing linear DNA; and;
producing concatemers comprising an ordered array of copies of at least two of the DNA circles through rolling circle amplification; and
sequencing the concatemers. In a preferred embodiment, the backbone is a circle comprising two recombinase recognition sites separated on one side by DNA comprising a linker and separated on the other side by DNA coding for a further restriction enzyme recognition site, and wherein the further restriction site is the only recognition site for the restriction enzyme in the backbone. In this embodiment, the method preferably further comprises digesting the DNA after the recombination with the restriction enzyme and subsequently removing linear DNA, prior to producing the concatemers. The further restriction site is preferably a 6 or more cutter, preferably a 7 or more cutter, preferably an 8 cutter. The ends produced by the digestion do not have to be blunt ends. In a preferred embodiment, the further restriction enzyme is not a blunt end cutter.

Target Site Specific Recombinases

A target site specific recombinase is a genetic recombination enzyme. Target site specific DNA recombinases are widely used in multicellular organisms to manipulate the structure of genomes, and to control gene expression. These enzymes, derived from bacteria and fungi, catalyze directionally sensitive DNA exchange reactions between short (30-40 nucleotides) target site sequences that are specific to each recombinase. These reactions enable four basic functional modules, excision/insertion, inversion, translocation and cassette exchange. Non-limiting examples of recombinases are Cre recombinase; Hin recombinase; Tre recombinase and FLP recombinase. Cre-recombinase was one of the first widely used recombinases. It is a tyrosine recombinase enzyme derived from the P1 Bacteriophage. The enzyme uses a topoisomerase I like mechanism to carry out site specific recombination events. The enzyme (38 kDa) is a member of the integrase family of site specific recombinase and it is known to catalyze the site specific recombination event between two DNA recognition sites (LoxP sites). This 34 base pair (bp) loxP recognition site consists of two 13 bp palindromic sequences, which flank an 8 bp spacer region. The products of Cre-mediated recombination at loxP sites are dependent upon the location and relative orientation of the loxP sites. Two separate DNA species both containing loxP sites can undergo fusion as the result of Cre mediated recombination. DNA sequences found between two loxP sites are the to be "foxed".

Red/ET Recombination

Recombineering exploits the phage derived protein pairs, either RecE/RecT from the Rac phage or Redα/Redβ from the λ phage, to assist in the cloning or subcloning of fragments of DNA into vectors without the need of restriction enzyme sites or ligases. The RecE/RecT, Redα/Redβ and other similar protein pairs are herein further referred to as Red/ET protein pairs A limitation of the original homologous recombination technique was due to the fact that bacterial RecBCD nuclease degrades linear DNA and initially the event had to be studied in RecBCD-deficient strains (7). This was overcome by the discovery that Redα and Redβ were assisted by Redγ, which inhibits RecBCD nuclease activity making it possible to use the technique in E. coli and other commonly used bacterial strains. In addition, the recombination efficiency was increased 10-100 times. The combination of these three enzymes (α, β and γ, or E, T and γ) in one vector was named Red/ET recombination and the basic principles of the method are that it requires two homology regions of >15, preferably >20, preferably >30 and preferably >42 bp in a linear fragment, double strand breaks (DSBs) in both ends, and another linear or circular plasmid in order for recombination to take place. Directional insertion is possible using two different homology regions to flank the target DNA and the insertion site.

DSBs are essential so that RecE or Redα can bind and degrade one chain of the DNA (5' to 3') and at the same time load RecT or Redβ to the single strand chain that is exposed. The single DNA strand loaded with the RecT or Recβ recombinase finds a perfect match sequence and joins the two sequences by either chain invasion or annealing.

Insertion of homology regions (HRs) is typically achieved by including them in the oligonucleotides that are used for amplification of the products used as linear substrates for the recombination event. If longer fragments of DNA are needed for the procedures then the HRs may be inserted with conventional restriction/ligation techniques using plasmids or adaptors.

Restriction Enzyme Recognition Site

A restriction enzyme recognition sites are often also simply referred to as restriction enzyme site; restriction site or restriction recognition site. They are locations on a DNA molecule containing specific sequences of nucleotides, which are recognized by restriction enzymes. These are generally palindromic sequences. A particular restriction enzyme may cut the sequence between two nucleotides within its recognition site, or somewhere nearby. The enzymes typically cut both strands of the DNA molecule, which is typically followed by separation of the ends. So called nicking enzymes also recognize restriction sites but cut only one of the two strands. The resulting DNA molecule remains associated but one of the two strands has a nick.

Restriction Enzyme Types

Naturally occurring restriction endonucleases (restriction enzymes) are categorized into four groups (Types I, II III, and IV) based on their composition and enzyme cofactor requirements, the nature of their target sequence, and the position of their DNA cleavage site relative to the target sequence. DNA sequence analysis of restriction enzymes however show great variations, indicating that there are more than four types. All types of enzymes recognize specific short DNA sequences and carry out the endonucleolytic cleavage of DNA to give specific fragments with terminal 5'-phosphates.

Type I enzymes (EC 3.1.21.3) cleave at sites remote from a recognition site and require both ATP and S-adenosyl-L-methionine to function. They are multifunctional in that they have both restriction and methylase (EC 2.1.1.72) activities.

Type II enzymes (EC 3.1.21.4) cleave within or at short specific distances from a recognition site. Most type II enzymes require magnesium. They typically have a single function (restriction).

DNA Phosphorylation

Single- or double-stranded DNA with a 5'-hydroxyl terminus has to have a 5' phosphate group for efficient ligation. 5' ends without such phosphate groups can be phosphorylated prior to ligation. A number of polynucleotide kinases, including T4 PNK (NEB #M0201) and T4 PNK (3' phosphatase minus) (NEB #M0236), can be used to transfer the γ-phosphate of ATP to a 5' terminus of DNA.

DNA Dephosphorylation

Digested DNA typically possesses a 5' phosphate group that is required for ligation. In order to prevent self-ligation, the 5' phosphate can be removed prior to ligation. Dephosphorylation of the 5' end prohibits self-ligation, enabling the artisan to manipulate the DNA as desired before re-ligating. Dephosphorylation can be accomplished using any of a number of phosphatases, including the Quick Dephosphorylation Kit (NEB #M0508), Shrimp Alkaline Phosphatase (rSAP) (NEB #M0371), Calf Intestinal Alkaline Phosphatase (CIP) (NEB #M0290) and Antarctic Phosphatase (NEB #M0289).

DNA Ligation

Ligation of DNA is a central step in many modern molecular biology workflows. DNA ligases catalyze the formation of a phosphodiester bond between the 3' hydroxyl and 5' phosphate of adjacent DNA residues. In the lab, this reaction is used to join dsDNA fragments with blunt or cohesive ends to form recombinant DNA plasmids, to add bar-coded adapters to fragmented DNA during next-generation sequencing and many other applications. The DNA ligase from bacteriophage T4 is the ligase most-commonly used. It can ligate cohesive or "sticky" ends of DNA, oligonucleotides, as well as RNA and RNA-DNA hybrids. It can also ligate blunt-ended DNA with great efficiency. Single stranded DNA can be ligated efficiently with CircLigase™ II ssDNA Ligase* (epicenter). This is a thermostable enzyme that catalyzes intramolecular ligation (i.e., circularization) of ssDNA templates having a 5'-phosphate and a 3'-hydroxyl group. CircLigase II ssDNA Ligase ligates ends of ssDNA in the absence of a complementary sequence. The enzyme is therefore useful for making circular ssDNA molecules from linear ssDNA. Circular ssDNA molecules can be used as substrates for rolling-circle replication or rolling-circle transcription.

For the purpose of clarity and a concise description it is here mentioned that where a step is performed on or with one or more substrate(s) and which step is catalyzed by one or more enzymes, this step is performed by contacting the substrate(s) with the enzyme(s). This is typically done by adding the enzyme(s) to the substrate(s) in an appropriate buffer.

For the purpose of clarity and a concise description features are described herein as part of the same or separate embodiments, however, it will be appreciated that the scope of the disclosure may include embodiments having combinations of all or some of the features described.

EXAMPLES

Example 1

Materials and Methods

Methods are described herein that allow detection of genetic variations by sequencing of a nucleic acid sequences in a pool of nucleic acid molecules (DNA) like ctDNA (circulating tumor DNA), cfDNA (cell-free DNA), genomic DNA, RNA, products of the polymerase chain reaction (PCR) or other products.

In this process, a "product" obtained is a long (>10 Kb) linear dsDNA formed by multiple units consisting of nucleic-acid-backbone copies. The concatemerization/multimerization of such a unit is necessary to discriminate the detection of a real genetic variation from a sequencing error. In fact, in the case of rare genetic variations, that occur in less than 1% frequency within a pool of DNA molecules, direct sequencing, e.g., short-read sequencing cannot be applied anymore, because the sequencing error rate is higher than the mutation frequency. Using the method described above, the same rare sequence (genetic variation) is represented multiple times in long concatemers, which provides very high confidence about mutation presence, even if the mutation frequency is low in the original pool of nucleic acid molecules.

The design of backbones to capture nucleic acids brings several advantages for obtaining nucleic acids with high efficiency and specificity and is crucial for computational analysis of sequencing data.

Preferred features of the backbone molecules are:
1) blunt restriction sites coded at the extremities of the backbone serve for improved ligation efficiency of the short DNA.
2) recognition sites for DNA nicking enzymes that are used to generate the "single-stranded template" for rolling circle amplification.
3) restriction enzyme target sites that can be used to perform sequential ligation of multiple short DNA molecules into one circular DNA.
4) molecular identifiers that enable to discrimination of original captured nucleic acids and their subsequent sequencing reads Additionally, the backbones serve as a control sequence during data analysis. Based on the backbone sequence reads, the error-rate of each sequencing read can be inferred, enabling accurate estimation of the likelihood of genetic variations within captured nucleic acid sequences.

2. Materials and Methods for Cyclomics Technology 2.1 Backbones Design

An iterative approach of alternating backbone design was used, followed by experimental testing to find the best backbones that would allow most efficient circularization, i.e., capturing of double-stranded nucleic acid molecules.

The basal design of our backbones can include one or more of the following parts:
1) A 3' sequence coding for half restriction site.
2) One or more sites that allow nicking of the double-stranded backbone sequence
3) One or more Type1 or Type2 restriction site
4) A secondary cloning site
5) A flexible DNA stretch that enables efficient circularization (bending) of the backbone molecule
6) Unique molecular barcode sequences to tag each individual backbone molecule
7) A 5' sequence coding for the other half of the same blunt restriction site used in 1
8) Phosphorylation at the 3' and 5' end of the backbone molecule The flexible DNA stretches have been designed with the help of a custom-made evolutionary algorithm imposing various selection criteria among which:
1) a high overall complexity of the sequence
2) absence of repeated DNA motifs longer than 5 bases
3) absence of self-complementary sequences of more than 5 nucleotides
4) at each design iteration cycle the most flexible sequences are selected Following the above design, each sequence was manually checked using the mFold server (unafold.rna.albany.edu/) and modified to reduce as much as possible the formation hairpins and, in general, complex secondary structure.

2.2 Preparation of DNA Templates for Rolling Circle Amplification

The following protocols are meant for the preparation of a template suitable for an RCA reaction. Any circular DNA is a suitable template and different protocols are available and known in the art that can handle either dsDNA or ssDNA.

Examples of dsDNA that can circularize are: cfDNA, ctDNA, sheared genomic DNA, PCR amplicons.

Examples of ssDNA includes: cDNA, viral DNA.

2.3. dsDNA Circularization Reaction

A dephosphorylated dsDNA molecule here called "insert" is ligated to a phosphorylated backbone at both ends forming a circular dsDNA product.

The reaction is carried out with the simultaneous use of a DNA ligase and a restriction enzyme in the appropriate buffer conditions.

The buffer conditions have been optimized to allow Ligation, Digestion and PlasmiSafe treatment in a one-pot reaction, without intermediate DNA purification steps.

Considering the backbone in the Example, having SrfI half-site at the extremities the components of the reaction are the following:
Buffer 1×
50 mM Potassium Acetate
20 mM Tris-acetate
10 mM Magnesium Acetate
100 µg/ml BSA
1 mM ATP
10 mM DTT
DNA and enzymes
Backbone+Insert in a 3:1 molar ratio
1 unit T4 DNA Ligase
1 unit Srf1
1 unit HMGB1

$H_2O$ was added to a final volume of 20 to 50 µl (depending on the DNA load), followed by 1 h incubation at 22° C. and subsequent heat inactivation for 15 min at 65° C.

The presence of the restriction enzyme increases the overall yield of the reaction avoiding the accumulation of backbone concatemers while the concatemerization of the inserts is avoided by preventive dephosphorylation. HMGB1 (high-mobility group protein 1) is used to facilitate bending of short DNA thus increasing circularization efficiency.

The most abundant product of the above reaction is a circular dsDNA containing one backbone and one insert.

Removal of Linear DNA

To remove residual linear dsDNA, the templates are treated with 1 µl of Plasmid-Safe DNase for 15 min at 37° C., followed by heat inactivation for 30 min at 70° C.

3. Materials and Methods for Detection of Fusion Genes

A protocol was developed to employ circularization and rolling circle amplification for the detection of of fusion-genes, based on RNA extracted from human cells. In this case, ssDNA (as opposed to dsDNA) is used as input for the circularization and amplification reaction. The protocol can be generalized to sequence any RNA of interest.

The first parts of the protocol involve standard procedures for "RNA extraction" and "cDNA amplification", e.g., Trizol-based RNA isolation followed by polyT primer cDNA synthesis using reverse transcriptase.

After digestion of RNA from RNA-DNA hybrids, a linear ssDNA is left.

At this point, a ssDNA Ligase is used to self-circularize the input DNA.

Different ssDNA Ligases are available in the market. CircLigase II (Epicentre) has been used to perform proof-of-principle experiments. Circular ssDNA obtained following the vendor protocol have been successfully used as a template for RCA reaction using specific primers to direct the amplification of the fusion-gene of interest.

The following protocol describe in details all the passages right after RNA isolation.

3.1 Removal of Residual DNA

Buffer, enzyme and inactivation reagent were purchased from Thermo Fisher (TURBO DNase kit)

In a 0.5 ml tube mix:

| | |
|---|---|
| 10x Reaction Buffer | 1 µl |
| Extracted RNA | 1 µg |
| TURBO DNase | 0.5 µl |
| $H_2O$ to 10 µl final volume | |

Next the solution was mixed and incubate for 30 min at 37° C. Inactivated by adding 2 μl of inactivation reagent. Mixed for 5 min.

3.2 cDNA Synthesis

SuperScript II kit from Invitrogen was used, any other kit for cDNA transcription may be used instead.

To the previous reaction was added:
Primers 2 mM (Random hexamers or specific) 1 μl
  Primers is phosphorylated

| | |
|---|---|
| dNTPs (10 mM each) | 1 μl |

Incubated at 65° C. for 5 min then put on ice for 5 min. The primers were annealed to the template during this step. Next, was added:

| | |
|---|---|
| 5x First Strand buffer | 4 μl |
| 100 mM DTT | 1 μl |

Incubated at 42° C. for 2 min then added 1 μl of SSII enzyme and incubated 42° C. for 45 min. Finally, the reaction at 70° C. for 15 min was inactivated.

3.3 Removal of RNA

RNaseH was purchased from ThermoFisher.

To the previous reaction 1 μl of RNaseH enzyme was added and incubated at 37° C. for 20 min, then heat-inactivated at 70° C. for 10 min.

3.4 Chelation of Divalent Metal Ions

This step was added to lower the concentration of free $Mg^{2+}$ that would otherwise inhibit the ssCircLigase II used in the next reaction.

To complex all free Mg2+, to the previous reaction was added:
50 mM EDTA stock (0.9 EDTA+50 ml H20) 2 μl 3.5 ssDNA Circularization For this reaction, the ssDNA CircLigase II kit from Epicentre was used.

| | |
|---|---|
| 10x Reaction Buffer | 2 μl |
| MnCl$_2$ (Manganese (Mn) is not to be confused with magnesium (Mg)) | 1 μl |
| Betaine | 4 μl |
| CircLigaseII | 1 μl |
| ss-cDNA | 10 pmoles |
| H$_2$O to 20 μl final volume | |

Incubated at 60° C. for 1-2 hours, then heat-inactivated the reaction at 70° C. for 10 min.

At this point the reaction was treated with PlasmidSafe (optional) and used as a template for the RCA reaction (following steps).

3.6 Primer Annealing

Depending on the cases, random primers or backbone specific primer or target-specific primers were used.

In this step, the template DNA could also be single-stranded circular DNA, as in the case of self-circularized cDNA.

The primers have two 3'-terminal phosphorothioate (PTO) modified nucleotides that are resistant to the 3'→5' exonuclease activity of proofreading DNA polymerases, such as phi29 DNA Polymerase. They also have 5'- and 3'-hydroxyl ends.

If the circular DNA is in water, for example, in the case of a previous purification, then add 11% of the volume of 10× Annealing Buffer.

10× Annealing Buffer
  100 mM Tris, pH 7.5-8.0
  500 mM NaCl
  10 mM EDTA

Concentrated primers (50-100 μM) were added to the reaction to a final concentration of 5 μM.

The reaction was brought to 98° C. and subsequently let to cool down slowly to room temperature.

Rolling Circle Amplification

The following volumes were calculated for a 50 μl reaction.

When the template was in Annealing buffer, 20 μl of the template was taken and to it was added:
  5 μl Phi29 Buffer (10×)
  1 μl BSA
  1 μl dNTPs (10 μM)
  2 μl Pyrophosphatase
  1 μl Phi29 DNA Polymerase
  H$_2$O to 50 μl When the template is in Circularization buffer, 46 μl of the template was taken and to it was added:
  1 μl dNTPs (10 μM)
  2 μl Pyrophosphatase
  1 μl Phi29 DNA Polymerase Optional, to the reaction was added:
  0.5 μl Uracil-DNA glycosylase (to remove any deaminated cytosines from DNA)
  0.5 μl Formamidopyrimidine-DNA glycosylase (to remove 8-oxo-guanine products)

Reaction Condition

Depending on the amount of input DNA (template) the reaction was run:
  >>3 h @ 30° C. if the template is 10-50 ng
  >>6 h @ 30° C. if the template is 5-10 ng
  >>12 h @ 30° C. if the template is 0.5-5 ng 4. Materials and Methods for targeted Cyclomics To enable ultra-accurate targeted sequencing of any double stranded DNA molecule, a workflow was designed based on existing molecular-inversion-probe (MIP) technology. Unique aspects are the design of the MIP capture backbone (minimization of backbone size, addition of unique molecular barcodes, probe specificity and distance) and the combination of the assay with rolling circle amplification.

4.1 Generation of Probes

Amplify off-array oligonucleotides (MIP precursors) using PCR: (2.5 hrs)

1. Array-derived MIP precursor oligonucleotides (mixture of 100-mers obtained from Agilent) were dissolved to a final concentration of 100 nM in Tris-EDTA buffer with a pH of 8 and 0.1% Tween®.

2. The following 400 μl PCR mix was prepared in a 1.5 ml centrifuge tube.

| Reagent | Volume (μl) | Final Concentration |
|---|---|---|
| 2x iProof HF PCR master mix (Biorad) | 200 | 1x |
| Oligo_Fwd_Amp Primer (100 μM) | 2 | 500 nM |
| Oligo_Rev_Amp Primer (100 μM) | 2 | 500 nM |
| SYBRGreen I 100 x (Invitrogen)** | 1 | 0.2X |
| Template (100 nM in 0.1% Tween®) | 1 | 250 pM |
| Water | 194 | |

It was split into 8×50 μl reactions in 0.2 ml PCR tubes. One PCR preparation yielded around 1.5 μg of amplified DNA.

3. The following PCR cycling program, was used on a real-time thermocycling instrument such as the Biorad MJ Mini.
   1) 98° C. for 30 seconds
   2) 98° C. for 10 seconds
   3) 60° C. for 30 seconds
   4) 72° C. for 30 seconds (read plate)
   5) repeat steps 2 to 4×25 cycles
   6) 4° C. indefinitely 4. PCR reactions were combined and cleaned up on one column using the QIAquick PCR purification kit following the manufacturer's instructions. Eluted with 90 μl elution buffer.

5. Used a Qubit High Sensitivity dsDNA Assay Kit to quantify 1 μl of the amplified DNA. Capturing Exons with Molecular Inversion Probes 6. Analyzed 1 μl amplified DNA on a 6% TBE PAGE gel (Invitrogen) to verify amplification. Product appeared as a single band at 110 bp, as the primers added an additional 10 bp.

Digest PCR product with nicking restriction endonucleases to generate 70-mer MIPs (7.5 hrs):

1. Added was 10 μl of NEB—2 (10×) and 5 μl of Nt.AlwI (10 U/μl; NEB) to 85 μl of PCR product (total volume of 100 μl)
2. Mixed and split to two tubes of 50 μl each. Incubate at 37° C. for 3 hours, followed by 80° C. for 20 minutes in a thermocycler
3. The temperature was dropped to 65° C. for at least 1 minute. Added 2.5 μl of Nb.BsrDI (2 U/μl NEB) to each of the 50 μl reactions
4. Left at 65° C. for 3 hours, followed by 80° C. for 20 minutes
5. Purified two 50 μl digestion reactions on one column using reagents from the QIAquick Nucleotide Removal Kit. Eluted each column in 30 μl elution buffer. Yields of 80-90% were observed for this step.

Quantify Usable Probe Using a Denaturing Gel (2 Hrs):

1. Accurate quantification of usable MIP inside the digested probe mix is important as it determines how much probe mix to add to the capture reaction.
2. Prepared two-fold dilutions of a NEB 100 bp DNA ladder (dilutions from 500 ng to 62 ng were used).
3. Mixed 2×TBE-Urea sample buffer (Invitrogen) with 1 μl digested probe and the dilutions made above.
4. DNA was denatured by heating to 95° C. for 5 minutes and immediately transferring to ice.
5. Samples were run on a precast 6% TBE-urea denaturing PAGE gel (Invitrogen) for 1 hr at 160 V.
6. The amount of usable MIP was quantified in the digested mixture by comparing the intensity of ladder dilutions with the intensity of the 70 bp band. This MIP concentration was used when determining the volume of probe mix to add to a capture reaction.

4.2 Capturing Exons with Molecular Inversion Probes
Hybridize probes to genomic DNA (37 hrs):

1. For each sample to capture, the following reagents were added in a 0.2 ml PCR tube. The final capture reaction volume was 25 μl. Because there is no size selection of the 70 bp MIP, the volume of probe mix to add was based on the concentration of usable MIP.

| Reagent | Volume (μl) per sample | Final Concentration in reaction |
|---|---|---|
| 750 ng genomic DNA* | 3 | 30 ng/μl* |
| 10 × Ampligase buffer (Epicentre) | 2.5 | 1x |
| 40 ng (2 pmol) of MIP** | 3 | 1.6 ng/μl** |
| Blocking Oligonucleotide (100 μM) | 0.1 | 0.4 μM |
| Water | 16.4 | |

2. Denatured at 95° C. for 10 minutes.
3. Incubate at 60° C. for at least 36 hours to hybridize MIPs to gDNA.

Circularize captured exons: (1 day)

1. Prepared a mix of ligase and polymerase enzymes to add to each capture reaction:

| Reagent | Volume (μl) per sample | Final Concentration in capture reaction |
|---|---|---|
| 10 × Ampligase buffer (Epicentre) | 0.45 | 1x |
| 10 U/μl Stoffel** (Applied Biosystems) | 2 | 0.8 U/μl |
| 100 U/μl Ampligase** (Epicentre) | 1 | 4 U/μl |

Prepared this mix on ice, and kept it cold before adding 4.7 μl into the capture reaction.

1. Incubated at 60° C. for an additional 24 hours to allow for gap-fill and ligation to circularize captured regions.

Exonuclease select for circularized product: (1 hr)

1. Prepared a mix of exonucleases to add to each capture reaction in order to remove uncaptured gDNA, excess probe and blocking oligonucleotide:

| Reagent | Volume (μl) per sample | Final Concentration in reaction |
|---|---|---|
| Exo I 20 U/μl | 2 | 1.7 U/μl |
| Exo III 100 U/μl | 2 | 8.3 U/μl |

2. Reduced the temperature of the capture reaction to 37° C. and allowed it to incubate for at least one minute before adding 4 μl of exonuclease mix.
3. Incubated for 15 minutes at 37° C.
4. Inactivated exonuclease enzymes by heating reaction at 95° C. for 2 minutes.
5. Used 100 ng of the reaction product as the template for rolling circle amplification.

4.3 Rolling Circle Amplification

1. Vacuum dried 20 ul 2× annealing buffer to 1 ul
2. Added 40 ul circular DNA (around 10 ng)
3. Added 4 ul 50 uM random primers
4. Incubated the reaction for 5 min at 90 C and slowly cool down to room temperature
5. Added the following reagents: 10 ul 10× Phi29 buffer, 2 ul 100×BSA, 2 ul 10 mM dNTPs, 2 ul Phi29 polymerase, 4 ul Pyrophosphatase 0.1 U/ul, 40 ul water
6. Incubated for 19 hours at 30 C, followed by 10 min at 65 C
7. Cleaned the reaction products using Ampure XP beads (0.4V)

The cleaned reaction product was used for any long read sequencing protocol.

5. List of Backbones Designed and Tested

>BB1 (199 bp)
(SEQ ID NO: 5)
GGGCATGCACAGATGTACACGTACGATCATGTACGTCACGCGAGTGCAC
GTCGTCATAGCTGTCGAGTACTGTACTGACTGTCTCGAGCCTCAGCGAG
TATTTAAATCTACGTAGAGTACGACTGCGCAGATGTGATCAGTGACTAC
GTGACACTGTACATCAGCACGATCGATGACTAGATGCTGCATGACATAG
CCC

>BB2 (259 bp)
(SEQ ID NO: 6)
GGGCATGCACAGATGTACACGTACGATCATGTACGTCACGCGAGTGCAC
GTCGTCATAGCTGTCGAGTACTGTACTGACTGTCTCGAGCCTCAGCGAG
TATTTAAATCTACGTCACCGGGTCTTCGAGAAGACCTGTTTAGAGTACG
ACTGCAAATGGCTCTAGAGGTACCCGTTACATAACTTACGCAGATGTGA
TCAGTGACTACGTGACACTGTACATCAGCACGATCGATGACTAGATGCT
GCATGACATAGCCC

>BB2_100 (341)
(SEQ ID NO: 7)
GGGCATGCACAGATGTACACGTACGATCATGTACGTCACGCGAGTGCAC
GTCGTCATAGCTGTCGAGTACTGTACTGACTGTCTCGAGCCTCAGCGAG
TATTTAAATCTACGTCACCATATATATGGATATATATATGGATATATAT
ATATATGGATATATGGATATATATATATATATGGATATGTATGGATA
TATATATATGGATATGGATGTTTAGAGTACGACTGCAAATGGCTCTA
GAGGTACCCGTTACATAACTTACGCAGATGTGATCAGTGACTACGTGAC
ACTGTACATCAGCACGATCGATGACTAGATGCTGCATGACATAGCCC

>BB3 (514 bp)
(SEQ ID NO: 25)
AACGCCAGCAACGCGGCCTTTTTACGGTTCCTGGCCTTTTGCTGGCCTT
TTGCTCACATGTGAGGGCCTATTTCCCATGATTCCTTCATATTTGCATA
TACGATACAAGGCTGTTAGAGAGATAATTGGAATTAATTTGACTGTAAA
CACAAAGATATTAGTACAAAATACGTGACGTAGAAAGTAATAATTTCTT
GGGTAGTTTGCAGTTTTAAAATTATGTTTAAAATGGACTATCATATGC
TTACCGTAACTTGAAAGTATTTCGATTTCTTGGCTTTATATATCTTGTG
GAAAGGACGAAACACCGGGTCTTCGAGAAGACCTGTTTTAGAGCTAGAA
ATAGCAAGTTAAAATAAGGCTAGTCCGTTATCAACTTGAAAAAGTGGCA
CCGAGTCGGTGCTTTTTGTTTAGAGCTAGAAATAGCAAGTTAAAATA
AGGCTAGTCCGTTTTTAGCGCGTGCGCCAATTCTGCAGACAAATGGCTC
TAGAGGTACCCGTTACATAACTTA

>BBpX2 (557 bp)
(SEQ ID NO: 8)
GGGCATGCACAGATGTACACGAACGCCAGCAACGCGGCCTTTTTACGGT
TCCTGGCCTTTTGCTGGCCTTTTGCTCACATGTGAGGGCCTATTTCCCA
TGATTCCTTCATATTTGCATATACGATACAAGGCTGTTAGAGAGATAAT
TGGAATTAATTTGACTGTAAACACAAAGATATTAGTACAAAATACGTGA
CGTAGAAAGTAATAATTTCTTGGGTAGTTTGCAGTTTTAAAATTATGTT
TAAAATGGACTATCATATGCTTACCGTAACTTGAAAGTATTTCGATTT
CTTGGCTTTATATATCTTGTGGAAAGGACGAAACACCGGGTCTTCGAGA
AGACCTGTTTTAGAGCTAGAAATAGCAAGTTAAAATAAGGCTAGTCCGT
TATCAACTTGAAAAAGTGGCACCGAGTCGGTGCTTTTTGTTTAGAGC
TAGAAATAGCAAGTTAAAATAAGGCTAGTCCGTTTTTAGCGCGTGCGCC
AATTCTGCAGACAAATGGCTCTAGAGGTACCCGTTACATAACTTATAGA
TGCTGCATGACATAGCCC

6. Additional Details on the Generation of BB2_100 and BBpX2

BB2 was optimized by inserting flexible sequences using the BbsI Cloning Site present in BB2. The insert consisted in a 100 bp long DNA stretch obtained by in-silico design (see section 7) and BbsI restriction site (bold in the sequences below) was added at the extremities for cloning purpose. The full insert was obtained by the annealing of two shorter oligonucleotides, (sense and antisense). The oligonucleotides were ordered as single-strand oligonucleotides from IDT DNA Technologies. The forward and reverse strand were annealed and the annealing product, now a dsDNA with sticky ends, was resolved on an agarose gel. Following, insert was cloned into BB2 with a Golden-Gate cloning reaction similar to the one described by (Ran et al. 2013).

The full insert sequence and the oligos used to produce it are the following:

>insert BB2_100
(SEQ ID NO: 26)
CACCATATATATGGATATATATATGGATATATATATATATGGATATATG
GATATATATATATATATGGATATGTATGGATATATATATATATGGAT
ATGGATGTTT

>sense oligo
(SEQ ID NO: 27)
CACCATATATATGGATATATATGGATATATATATATATGGATATATG
GATATATATATATATATGGATATGTATGGATATATATATATATGGAT
ATGGAT >antisense oligo
(SEQ ID NO: 28)
AAACATCCATATCCATATATATATATATCCATACATATCCATATATATA
TATATATCCATATATCCATATATATATATATCCATATATATATCCAT
ATATAT BBpX2 was obtained by addition of the SrfI-half-sites (GGGC) and the rest of the Universal Primer sequences (underlined in the sequences below) at the extremities of a PCR amplicon. BB3 was used as a template for the PCR reaction.

>BBpX to BBpX2-F
(SEQ ID NO: 29)
<u>GGGCATGCACAGATGTACACG</u>aacgccagcaacgcggc >BBpX to BBpX2-R
(SEQ ID NO: 30)
<u>GGGCTATGTCATGCAGCATCTA</u>taagttatgtaacgggtacctct The sequences above have the template-annealing part in lowercase and a flanking region in uppercase. The SrfI-halfsites are highlighted in orange the rest of the uppercase sequence is part of a constant sequence present at the extremities of all our backbone. The constant sequence is not essential for the backbone but is useful to standardize their amplification during the production steps. The following primers are indeed able to amplify any backbone made so far:

```
>Universal SrfI-BB-F
                                        (SEQ ID NO: 31)
GGGCATGCACAGATGTACACG >Universal SrfI-BB-R
                                        (SEQ ID NO: 32)
GGGCTATGTCATGCAGCATCTA
```

7. List of Insert Sequences

```
>Insert 17.1 (TP53, chr17:7576971-7577132)
                                        (SEQ ID NO: 33)
TAACTGCACCCTTGGTCTCCTCCACCGCTTCTTGTCCTGCTTGCTTACC

TCGCTTAGTGCTCCCTGGGGGCAGCTCGTGGTGAGGCTCCCCTTTCTTG

CGGAGATTCTCTTCCTCTGTGCGCCGGTCTCTCCCAGGACAGGCACAAA

CACGCACCTCAAAG

>Insert 17.2 (TP53, chr17:7578161-7578394)
                                        (SEQ ID NO: 34)
CAGTTGCAAACCAGACCTCAGGCGGCTCATAGGGCACCACCACACTATG

TCGAAAAGTGTTTCTGTCATCCAAATACTCCACACGCAAATTTCCTTCC

ACTCGGATAAGATGCTGAGGAGGGGCCAGACCTAAGAGCAATCAGTGAG

GAATCAGAGGCCTGGGGACCCTGGGCAACCAGCCCTGTCGTCTCTCCAG

CCCCAGCTGCTCACCATCGCTATCTGAGCAGCGCTCAT
```

8. In-Silico Design of Flexible DNA Sequences

Flexible DNA sequences were used to improve the flexibility of BB2 by addition of a sequence of 100 bp that was specifically designed using a simple genetic algorithm. The same approach was used to design whole backbone core sequences from scratch. To these backbone core sequences restriction sites, barcodes or primer sites can be added as described elsewhere herein The optimization of backbone core sequences was done based on an evolutionary selection algorithm that optimizes the sequence for the following components:
1) High molecular flexibility
2) High sequence entropy
3) GC content between 30 and 60 percent, ideally closer to 50%
4) Absence of long, self-complementary stretches
5) Absence of long oligo polymers
6) Absence of repeated motifs (kmers)

Flexibility Calculation

A python implementation of the TwistFlex algorithm (margalit.huji.ac.il/TwistFlex/) (Menconi et al. 2015) was used to compute DNA flexibility at the twist angle of the input sequence. The flexibility of each individual dinucleotide is calculated based on the following table of angular degrees:

|   | A    | T    | C    | G    |
|---|------|------|------|------|
| A | 7.6  | 10.9 | 8.8  | 12.5 |
| T | 14.4 | 7.2  | 11.1 | 8.8  |
| C | 8.2  | 8.9  | 7.2  | 10.9 |
| G | 25   | 8.2  | 14.6 | 7.6  |

Subsequently, the mean flexibility of the entire sequence was considered for the selection in the evolutionary algorithm for backbone optimization. The mean flexibility of a DNA sequence is calculated as the sum of all dinucleotide angular degrees divided by the total number of dinucleotides. The flexibility threshold for our backbones was a mean of 12.5 angular degrees. Any sequence with a mean flexibility lower than 12.5 angular degrees was discarded.

Entropy calculation for determining sequence complexity

The Shannon entropy of a string is defined as the minimum average number of bits per symbol required for encoding the string.

The formula to compute the Shannon entropy is $$H = -\sum_i p_i \log_b p_i$$

where $p_i$ is the probability of character number i appearing in the sequence. The calculation can also be performed through: shannonentropy.netmark.pl/.

The above formula was implemented with the following python code:

```
def quick_entropy(sequence):
    alphabet = set(sequence) # list of symbols in the sequence
    # Frequency of each symbol in the sequence
    frequencies = [ ]
    for symbol in alphabet:
        frequencies.append(sequence.count(symbol) / len(sequence))
    # Shannon entropy as in
wiktionary.org/wiki/Shannon_entropy
    ent = 0.0
    for freq in frequencies:
        ent -= freq * math.log(freq, 2)
    return ent
```

The minimum entropy value required by our backbone core sequences is 1.5 Sh. Each sequence with a lower entropy value was discarded.

Self-Complementarity

The selected backbone core sequences were filtered for the presence of self-complementary stretches of 8 bases. A backbone having 8 or more consecutive bases self-complementary in the same strand is discarded.

Absence of Repeated Motifs (Kmers)

Backbone core sequences containing motifs of 6 bases repeated more than twice in the sequence, were filtered out.

Evolutionary Algorithm for Design of Newer Backbones (Beyond BB2)

Newer backbones were composed by flexible DNA plus a pair of fixed sequences at the extremities (Universal SrfI-BB F/R described in paragraph 6) that serve as primer-annealing sites for PCR amplification of the backbones and to add the half-restriction sites.

As any genetic algorithm (GA), the Cyclomics' GA is composed by a main loop where a pool of sequences is scored and selected. The selected ones are then used as input (parents) for the generation of new sequences (children).

Both parents and children are grouped in a new pool ready for the next iteration. The pseudocode of such a loop is the following:

for each iteration:

| | |
|---|---|
| filter(pool) | #discard unwanted sequences |
| score(pool) | #assign a score to each sequence |
| parents = select(pool) | #select the best sequences |
| children = mate(parents) | #generate new sequences |
| pool = parents + children | #combine parents and children in a new pool |

The algorithm is fully implemented in Python, the mating and the mutation operators, as well the main loop, were implemented from scratch following the general guidelines found in the literature (Hwang and Jang 2008; Bäck 1996; Coello Coello and Lamont 2004; Lobo, Lima, and Michalewicz 2007). The mate operator act on strings, the sequences, and it performs a single crossing-over at random position. The mutation operator adds random mutations in the parents or child sequences, such mutations may include small deletions and duplications. The filtering step is used to prune the pool from sequences having unbalanced CG content, low sequence entropy, and unwanted repeated kmers before the selection step. The selection itself, simply collect the best sequences scored by flexibility. Selected sequences are used as parents to produce children using the mating operator. To calculate sequence flexibility, existing code (Menconi et al. 2015) was adapted to fit the purposes.

9. Results

PCR was performed using primers 17.2-F (CAGTTGCAAACCAGACCTCA) (SEQ ID NO: 36) and 17.2-R (ATGAGCGCTGCTCAGATAG) (SEQ ID NO: 35) to obtain a PCR product with length of 234 bp covering a coding exon of TP53 (chr17:7578161-7578394, GRCh37). De PCR product—referred to as 17.2—was ligated into pJET (Thermo Fisher) according to standard procedures. The ligation products were transformed to E. coli Top10 cells and one colony was picked for collection of a (clonally propagated) pJET-17.2 plasmid. The sequence of 17.2 was verified by Sanger sequencing and found to be the same as the reference genome (GRCh37). Phosphothionate (PTO)-modified primer 17.2-R (ATGAGCGCTGCTCAGATA*G*, where * is the PTO modification) (see, SEQ ID NO: 35) (5 µM) were annealed to 50 ng of pJET-17.2 in the presence of 5 mM EDTA in a final volume of 20 µL. This reaction mixture was heated to 95° C. for 5 min followed by cooling to 4° C.

The 20 µL annealing reaction was supplemented with 0.2 u inorganic pyrophosphatase (Thermo Fisher), 10 u Phi29 (NEB), 1 µL of 10 mM dNTPs, 1 µL 100×BSA solution (NEB, 20 mg/mL) and 5 µL Phi29 10× reaction buffer (NEB). The resulting reaction mixture was incubated at 30° C. for 3 h following by 10 min at 65° C. The amplified high-molecular weight DNA was purified using Ampure beads (Agencourt), followed by 1D nanopore library preparation (Oxford Nanopore Technologies, SQK-LSK108). The resulting library was run on a MinION flowcell (FLO-MIN106, R9.4 chemistry) for 48 h.

10. DNA Quantification by Gel Densitometry

Agarose-gel densitometry is a method used to quantify DNA by image-analysis of gel bands by comparison of pixel brightness 1) between the ladder and the band of interest or 2) between the input band and the product band.

10.1 Using the Ladder as a Reference

Given the picture of an agarose gel containing a known amount of DNA ladder, the software ImageJ was used to estimate the brightness intensity of the bands. The correct circular products were quantified and compared to the input to calculate the efficiency of the circularization. The Measure function of ImageJ was used to determine the area and mean intensity of the bands on each gel. The mean intensity of the background of the image, as close as possible to the band in question was determined and subtracted from the band intensity. The resulting intensity was multiplied by the area of the band (referred to as level). To create a reference level, the ratio was also calculated for the band corresponding to 400 base pairs in the GeneRuler 50 bp DNA ladder (Thermo Fisher Scientific) in each image, showing the intensity for fifteen nanograms of DNA. To calculate the DNA content of each band in nanograms, the calculated level was divided by the reference level and multiplied by fifteen. The DNA content in moles was determined using the Promega DNA conversions tool dsDNA: µg to pmol. The efficiency of the circularization was calculated by dividing the correct product in moles by the input of insert in moles and multiplying by 100 percent. To validate this approach, the DNA content of the other bands in the DNA ladder was calculated and compared to the predicted DNA content. The DNA content per band was plotted for the predicted as well as the calculated value (FIG. 6).

10.2 Direct Comparison of Input and Product Bands

An alternative procedure to estimate the efficiency of circularization via gel-image analysis requires to have at least two lines on the gel, one with the input DNA and one with the product. Using ImageJ the ratio between the insert before the reaction (input) and the one left after the reaction (unreacted) can be estimated.

The brightness of the bands inside the yellow rectangle (input DNA on the left band and unreacted DNA on the right one) is measured and compared. In this case, the ratio between input and unreacted is 66:33. It is concluded that 50% of the initial DNA have reacted (FIG. 7A).

Next, the products band are compared (FIG. 7B).

It is known that the top band is the one representing the desired product while the band underneath is the non-circularized product. From the ratio between these two bands, it can be established that the circularization efficiency, defined as the amount of input DNA that was correctly circularized into the final product. If A is the ratio of reacted input and B is the ratio of correct product, then the efficiency is given by A*B. In this case, 50%*50%=25%.

REFERENCES

Bäck, Thomas. 1996. Evolutionary Algorithms in Theory and Practice: Evolution Strategies, Evolutionary Programming, Genetic Algorithms. Oxford University Press on Demand.

Coello Coello, Carlos A., and Gary B. Lamont. 2004. Applications of Multi-Objective Evolutionary Algorithms. World Scientific.

Hwang, Gi-Hyun, and Won-Tae Jang. 2008. "An Adaptive Evolutionary Algorithm Combining Evolution Strategy and Genetic Algorithm (Application of Fuzzy Power System Stabilizer)." In Advances in Evolutionary Algorithms.

Lobo, F. J., Claudio F. Lima, and Zbigniew Michalewicz. 2007. Parameter Setting in Evolutionary Algorithms. Springer Science & Business Media.

Menconi, Giulia, Andrea Bedini, Roberto Barale, and Isabella Sbrana. 2015. "Global Mapping of DNA Conformational Flexibility on Saccharomyces Cerevisiae." PLoS Computational Biology 11 (4): e1004136.

Ran, F. Ann, Patrick D. Hsu, Jason Wright, Vineeta Agarwala, David A. Scott, and Feng Zhang. 2013. "Genome Engineering Using the CRISPR-Cas9 System." Nature Protocols 8 (11): 2281-2308.

Example 2

Sequencing of Concatenated DNA Molecules

A PCR product was cloned covering position 17:7578265 of the TP53 gene into pJET (Materials and Methods, section 9). Following bacterial transformation, a single colony was picked and plasmid DNA was isolated to confirm the presence of the TP53 insert (data not shown). Next, a rolling-circle amplification (RCA) was performed on the isolated plasmid using phi29 polymerase and random hexamer primers (Materials and Methods, section 9). A high-molecular weight RCA product was obtained with a size>20 kb as estimated by gel-electrophoresis (FIG. 8A). The product was used as input for a 1D library preparation for sequencing on the Oxford Nanopore Technologies (ONT) MinION instrument and the resulting library was sequenced for 48 h according to manufacturer's specifications. A total of 16,248 sequencing reads was generated for this sample, with an average read length of 5.7 kb (FIG. 8B) and 2,083 reads longer than 10 kb. Nanopore/MinION sequence reads were mapped to the human reference genome (GRCh37, augmented with the pJET sequence) using LAST (Kielbasa et al. 2011). The subset of 2,083 reads>10 kb were examined for an alternating backbone (pJET) and insert (TP53 fragment) configuration (referred to as BI), which would be expected from the circular template that was used as input. It was observed that all of the 2,083 reads have multiple BI copies. For all the reads longer than 10 kb, a "pattern score" was computed, a number between 1 and 100 representing the regularity of the BI repetitions, calculated as BI/([B+I]/2)*100, where BI is the number of pJET-17.2 segments, B is the number of pJET segments and I is the number of 17.2 segments in a nanopore read. The majority of the long reads have a pattern score of 100 indicating the correctness of the RCA product, i.e., repeats of BI units (FIG. 8C). These reads were used to extract the insert sequences (17.2—TP53 fragment) and subsequently aligned the inserts from each read using Muscle (Edgar 2004a, [b] 2004) (FIG. 8D). For each read, a majority voting scheme was applied to the aligned 17.2 segments to derive a consensus sequence. The consensus was compared to the reference sequence to determine the accuracy as function of the number of BI copies in the read (FIG. 8E). This experiment demonstrates proof of concept for obtaining accurate consensus reads based on nanopore sequencing of multiple copies of a DNA molecule (Li et al. 2016). In a next step backbone design improved, which reduce the amount of sequencing throughput for sequencing of the backbone (pJET—3 kb—in the above experiment).

Optimization of a Linear dsDNA Backbone
Backbone Design Principles

As a first step toward optimizing capture and circularization of short DNA molecules, different designs of a backbone sequence were tested mediating this process. Three parameters were compared: the length of the backbones (longer DNA molecules (backbones) are thought to be easier to circularize but this leads to a waste of sequencing information as the majority of each read will then consist of backbone sequences). Second, DNA molecules that are shorter than ~200 bp, are thought to be difficult to circularize because of their relative stiffness (Shore, Langowski, and Baldwin 1981). Third, the flexibility of a given DNA molecule also depends on its base composition and sequence.

The first generation of backbones are BB1 and BB2 (Material and Methods, sequences in section 5). They were designed following the general principles highlighted in Materials and Methods, section 2). The aim of designing these backbones was to serve as basic building blocks upon which could be improved. These backbones contain a combination of several elements that can help in capturing of DNA molecules and subsequent amplification and sequencing, such as restriction sites, barcode sequences and/or nicking enzyme sites. Circularization was detected using BB1, but it was not very efficient and it was not taken along for further testing.

Shore, Langowski, and Baldwin 1981, proposed that circularization of blunt-ended short DNA molecules can be suboptimal if efficiency is desired. Next, a longer backbone was generated that would allow more efficient circularization in a short period of time (~1 h). The resulting backbone, named BB3, is a 514 bp long dsDNA fragment generated by PCR amplification of part of plasmid pX330 (Material and Methods, section 5 and 6). BB3 did not contain a restriction enzyme site at the extremities, and it was used only to test different ligation conditions (see below). Also, a modified version of BB3 was generated by adding SrfI sites, resulting in BBpX2.

The free energy values of each base-pair (Breslauer et al. 1986) were used and the deviation of the twist angle (degrees) (Sarai et al. 1989) to compute the flexibility of any given DNA sequence. A genetic algorithm was used to generate a population of sequences that are selected for high flexibility, short length and optimization of other parameters like the GC content, the presence of repeated motifs and sequence self-complementarity. A more detailed description of the genetic optimization algorithm as well as details of backbone structures is given in the Materials and Methods, section 8. To improve the circularization efficiency of the backbone while keeping its sequence short, several stretches of flexible DNA in-silico were designed. Such stretches have been used to improve the flexibility of the backbones. Backbone 2 (BB2) was modified by including a 100 bp long flexible sequence in the middle of its sequence. The resulting backbone (BB2_100) is 341 bp long and it contains SrfI half-restriction-sites at its extremities.

Measuring reaction products of BB2 and BB3 backbones in circularization reactions BB2 and BB3 were tested in a circularization reaction together with a PCR-product as insert, 17.2 (Materials & Methods, sections 2, 5 and 7). A first experiment was performed to establish the best reaction conditions to achieve optimal circularization products. The reactions were performed with and without the addition of plasmid safe DNAse, to obtain a clear view on linear and circular reaction products (FIG. 9A). BB2 showed consistent results in circularization efficiency but circular reaction product was not very abundant. A circularization reaction with BB3 resulted in a visible circular product (FIG. 9A) while a clear reaction product was not visible in case of BB2. However, by running the entire reaction mixture on a gel were able to observe a weak band following plasmid-safe digestion, indicating a correct circularized product consisting of BB2 and insert 17.2 (FIG. 9B).

The effect of different backbone-insert ratios on circularization efficiency

Next, the effect of different backbone-insert ratios were evaluated on the specificity and efficiency of formation of a circular backbone-insert product that was aimed for. Therefore, BB3 was used for a circularization experiment together with a 234 bp PCR product (17.2, Materials and Methods section 7) (FIG. 10).

The best circularization efficiency was obtained with a 3:1 molar ratio between backbone and insert. This setup was kept to perform further characterization. Note that the strategy used here is profoundly different from the one used for standard plasmid-based cloning. In standard cloning, the plasmid is usually dephosphorylated to avoid self-circularization and an excess of phosphorylated insert is added to the reaction. For Cyclomics technology, the backbone is phosphorylated and in excess while the insert is dephosphorylated. It was observed that this avoided ligation-dependent concatemerization of target and improved backbone target ligation efficiency.

The effect of flexible stretches on backbone circularization

In a subsequent experiment, the effect of the addition of a flexible DNA stretch on backbone circularization was tested. Therefore, the circularization efficiencies of BB2 with that of BB2_100 were compared (see above) and BB3 (FIG. 11), in a circularization reaction with insert 17.2. The flexible region in BB2_100 is rich in TA repeats but still complex enough to be unambiguously mapped to a reference sequence. During this test, the effect of HMGB1 and SrfI on the circularization reaction of BB2_100 was evaluated. HMGB1 is a known DNA bending protein, which could potentially improve circularization (Belgrano et al. 2013). Improved circularization efficiencies for BB2_100 compared to BB2 were observed, particularly when considering backbone:insert ratios of 3:1. Thus, it is concluded that backbone design can be optimized by the addition of flexible DNA stretches, to promote circularization efficiency. A greater circularization efficiency, estimated to be around 26% was achieved with an overnight circularization of BB2_100 and 17.2 (FIG. 12) demonstrating that a better reaction performance can be obtained modulating both backbone design and reaction conditions.

The Effect of SrfI on Formation of Backbone Circularization Products

One essential part of our backbones is the presence of a split restriction site at the extremities. If the backbone self-circularizes without insert, the full restriction site is reconstituted making the backbone susceptible to specific nucleases. In the following example, SrfI (GCCC|GGGC) half-restriction-sites were added at the extremities of the BB3, generating a new backbone that is called BBpX2, and SrfI nuclease was added in the reaction mixture together with T4 Ligase. SrfI has the advantage of recognizing an 8-bases-long site while most of the commercially available alternatives recognize 6-bases-long sites. Other sequences that are being evaluated are PmeI (GTTT|AAAC) and SweI (ATTT|AAAT). If the ligation reaction is performed in the presence of SrfI, any self-circularized backbone will be susceptible to restriction enzyme cleavage and thus it will return to the original linear form.

The effect of the restriction enzyme is clearly visible by comparing the first two lanes (FIG. 13). When SrfI is present, the linear backbone (thick bold band) is maintained and the overall reaction leads to very few byproducts. In the absence of SrfI (first lane) the majority of the backbone is wasted in the formation of several byproducts. The effect of SrfI can be further appreciated by the effect of Plasmid Safe DNAse treatment (last two lanes) which leads to degradation of linear DNA. If SrfI is added to the reaction (last lane), then only the expected product is formed, in contrast, without the addition of SrfI (third lane), a number undesired circular byproducts are produced.

Dephosphorylation of Inserts

To avoid self-polymerizations of the inserts, enzymatic dephosphorylation is performed using Antarctic Phosphatase that ensures high reactivity at low temperatures and can be fully inactivated at 65° C. in just five minutes.

Barcoding Strategies

Molecular barcoding is a strategy to tag individual DNA molecules, in order to classify the sequencing reads resulting from the DNA molecules. Barcodes can be used to classify sequencing reads (bioinformatically) by sample, thus allowing the pooling of multiple samples on a single sequencing run (Wong, Jin, and Moqtaderi 2013). In that case only a limited number of unique barcodes are used, one for each sample.

Additionally, barcodes can be used to label each DNA molecule separately and such barcodes are often referred to as unique molecular identifiers (UMIs). In this case, a large number of unique barcodes/UMIs (random sequences) is used to make the chance as low as possible that any two unrelated sequences get the same barcode. UMIs can be used to obtain absolute quantification of individual sequences (Kivioja et al. 2011).

Another application of UMIs is the detection and quantification of low-frequency mutations (Kou et al. 2016), for example, in cancer samples. This involves labeling of individual DNA molecules, followed by PCR amplification and deep sequencing. Subsequently, sequence reads can be grouped by UMI sequence and possible mutations can be detected and discriminated from sequencing errors. An elegant application of UMIs for mutation detection in ctDNA is outlined by Newman et al (Newman et al. 2016).

The design of backbone sequences with both sample-specific barcodes and UMIs are envisioned (FIG. 14). Such a strategy enable pooled sequencing of multiple independent samples as well as enhanced mutation detection power. Sample-specific barcodes will be 5-20 nucleotides in length and can be placed anywhere in the backbone sequence, provided that they do not influence backbone flexibility (and thus ligation efficiency). Random strings of 5-20 nucleotides, representing UMIs, will also be added to backbones for labeling of individual DNA molecules. The UMIs can be used to improve mutation detection by requiring at least two or more distinct molecules with a mutation, i.e., both molecules should have a unique UMI.

Rolling Circle Amplification from Circularized DNA Molecules

A circular DNA product obtained by the circularization reaction of backbone and insert can serve as a template for the generation of concatemers via rolling circle amplification (RCA). RCA has been tested using DNA (inserts) from very different sources including cfDNA, PCR amplicons, plasmids and cDNA (FIG. 15), using random hexamer primers.

Site-Directed RCA

In addition to the canonical RCA reaction, that involves random hexamers to initiate the amplification, the use of specific primers was devised to direct the amplification toward the region of interest, this method is called site-directed RCA. Such an approach could be of use in case only specific genes should be sequenced rather than the whole genome. The current way to accomplish this is via PCR enrichment of the gene of interest (Dowthwaite and Pickford 2015). However, PCR amplification is known to add errors in the amplicons (Shuldiner, Nirula, and Roth 1989); (Diaz-Cano 2001) and even a single amplification error occurring early during the PCR reaction can bias the final results (Diaz-Cano 2001; Quach, Goodman, and Shibata 2004); (Arbeithuber, Makova, and Tiemann-Boege 2016).

To test whether site-specific enrichment of a target region without the use of PCR can be obtained, he Cyclomics assay has been coupled with site-directed RCA.

Briefly, two distinct region of the TP53 gene, 17.1 ad 17.2 (Material and Methods section 7), were cloned into the pJET vector. The modified pJET vectors were used in a 1 to 1 molar ratio as a template for an RCA reaction in which a specific primer (17.2-R, Materials and methods section 9) targeting 17.2, but not 17.1, was used instead of the random hexamers. The reaction product was sequenced using a nanopore MinION instrument and the number of reads containing 17.1 and 17.2 were compared (FIG. 16). It is observed that sequencing reads containing insert 17.2 occurring at 14× access compared to reads containing 17.1, demonstrating that target selected RCA can be achieved using specific primers.

One-Pot Reaction Design

To enhance the usage of Cyclomics technology, the focus was on development of a streamlined experimental procedure. Thus, there is limited time-consuming and laborious steps like DNA purification, concentration and gel electrophoresis as much as possible. To this end, a protocol has been designed that is made by three simple consecutive steps that can be performed in one single tube limiting the need of performing purification or buffer exchanges.

The steps are: 1) circularization, 2) removal of linear DNA and 3) Rolling Circle Amplification (FIG. 17).

The first reaction of the Cyclomics protocol involves the insert DNA (I) and the backbone (BB), that are mixed together in the presence of T4 DNA Ligase and the restriction enzyme SrfI. The mixture is left at room temperature for 1 to 4 hours, followed by heat inactivation of the enzymes at 70° C. for 30 minutes. The second step of the Cyclomics protocol is performed by adding the PlasmidSafe enzyme to the reaction mixture, together with its buffer and 1 mM ATP. The mixture is incubated at 37° C. for 30 minutes and inactivated again. Before proceeding with the rolling circle amplification (reaction 3), RCA-primers are added to the mixture and a quick annealing step is performed by warming up the reaction up to 98° C. for 5 minutes. After the mixture is cooled at room temperature, Phi29, Pyrophosphatase, and the other components of the RCA reaction are added. The reaction is then incubated at 30° C. for at least 3 hours.

Consensus Calling

In order to detect mutations from long reads with concatemers a consensus of the target sequence is produced (FIG. 18). To this end, the long reads are split into backbone sequences and target sequences based on a LAST split-read mapping to the reference genome (Kielbasa et al. 2011). Target sequences are passed to the GATK UnifiedGenotyper for variant calling (DePristo et al. 2011). Post-hoc filtering is applied based on variant confidence scores to optimize sensitivity and specificity.

Examples of Application of Cyclomics Technology

Targeted Sequencing of a TP53 Mutation in Genomic DNA from Ovarian Cancer

The Cyclomics method has been tested on three tumor biopsies with a known mutation in TP53 (chr17:7578265, A→T, hg19) at variable frequency (1%, 9%, 14%), as previously assessed using short read targeted Ion Torrent sequencing (Hoogstraat et al. 2014). In short, PCR was performed on the targeted locus and ligated the resulting products to a specifically designed and optimized backbone that promotes efficient capture of the short DNA products. Subsequent ligation products were amplified and concatenated to form long DNA molecules with repeated copies of target/insert and backbone. Long DNA molecules were sequenced for a few hours using a nanopore MinION instrument (1D ligation based library prep). A total of 206,048 sequence reads were obtained for all three samples, which were processed by mapping with LAST (Kielbasa et al. 2011) and a custom algorithm for consensus calling (FIG. 18). Next, the mutation frequency from the consensus reads was estimated and a frequency for the TP53 mutation of 0.5%, 7.6% and 14% was observed, providing proof-of-concept for detection of low-frequency somatic mutations in cancer DNA using Cyclomics technology (FIG. 19).

REFERENCES

Arbeithuber, Barbara, Kateryna D. Makova, and Irene Tiemann-Boege. 2016. "Artifactual Mutations Resulting from DNA Lesions Limit Detection Levels in Ultrasensitive Sequencing Applications." DNA Research: An International Journal for Rapid Publication of Reports on Genes and Genomes 23 (6): 547-59.

Belgrano, Fabricio S., Isabel C. de Abreu da Silva, Francisco M. Bastos de Oliveira, Marcelo R. Fantappié, and Ronaldo Mohana-Borges. 2013. "Role of the Acidic Tail of High Mobility Group Protein B1 (HMGB1) in Protein Stability and DNA Bending." PloS One 8 (11): e79572.

Breslauer, K. J., R. Frank, H. Blocker, and L. A. Marky. 1986. "Predicting DNA Duplex Stability from the Base Sequence." Proceedings of the National Academy of Sciences 83 (11): 3746-50.

DePristo, Mark A., Eric Banks, Ryan Poplin, Kiran V. Garimella, Jared R. Maguire, Christopher Hartl, Anthony A. Philippakis, et al. 2011. "A Framework for Variation Discovery and Genotyping Using next-Generation DNA Sequencing Data." Nature Genetics 43 (5): 491-98.

Diaz-Cano, Salvador J. 2001. "Are PCR Artifacts in Microdissected Samples Preventable?" Human Pathology 32 (12): 1415.

Dowthwaite, Gary, and Jo Pickford. 2015. "PCR-Based DNA Enrichment Enhances Detection of Mutations in Oncology." MLO: Medical Laboratory Observer 47 (11): 18, 20.

Edgar, Robert C. 2004a. "MUSCLE: Multiple Sequence Alignment with High Accuracy and High Throughput." Nucleic Acids Research 32 (5): 1792-97.

———. 2004b. "MUSCLE: A Multiple Sequence Alignment Method with Reduced Time and Space Complexity." BMC Bioinformatics 5 (August): 113.

Hoogstraat, Marlous, Mirjam S. de Pagter, Geert A. Cirkel, Markus J. van Roosmalen, Timothy T. Harkins, Karen Duran, Jennifer Kreeftmeijer, et al. 2014. "Genomic and Transcriptomic Plasticity in Treatment-Naive Ovarian Cancer." Genome Research 24 (2): 200-211.

Kielbasa, Szymon M., Raymond Wan, Kengo Sato, Paul Horton, and Martin C. Frith. 2011. "Adaptive Seeds Tame Genomic Sequence Comparison." Genome Research 21 (3): 487-93.

Kivioja, Teemu, Anna Vaharautio, Kasper Karlsson, Martin Bonke, Martin Enge, Sten Linnarsson, and Jussi Taipale. 2011. "Counting Absolute Numbers of Molecules Using Unique Molecular Identifiers." Nature Methods 9 (1): 72-74.

Kou, Ruqin, Ham Lam, Hairong Duan, Li Ye, Narisra Jongkam, Weizhi Chen, Shifang Zhang, and Shihong Li. 2016. "Benefits and Challenges with Applying Unique Molecular Identifiers in Next Generation Sequencing to Detect Low Frequency Mutations." PloS One 11 (1): e0146638.

Li, Chenhao, Kern Rei Chng, Esther Jia Hui Boey, Amanda Hui Qi Ng, Andreas Wilm, and Niranjan Nagarajan. 2016. "INC-Seq: Accurate Single Molecule Reads Using Nanopore Sequencing." GigaScience 5 (1): 34.

Newman, Aaron M., Alexander F. Lovejoy, Daniel M. Klass, David M. Kurtz, Jacob J. Chabon, Florian Scherer, Henning Stehr, et al. 2016. "Integrated Digital Error Suppression for Improved Detection of Circulating Tumor DNA." Nature Biotechnology 34 (5): 547-55.

Quach, Nancy, Myron F. Goodman, and Darryl Shibata. 2004. "In Vitro Mutation Artifacts after Formalin Fixation and Error Prone Translesion Synthesis during PCR." BMC Clinical Pathology 4 (1). doi:10.1186/1472-6890-4-1.

Sarai, A., J. Mazur, R. Nussinov, and R. L. Jernigan. 1989. "Sequence Dependence of DNA Conformational Flexibility." Biochemistry 28 (19): 7842-49.

Shore, D., J. Langowski, and R. L. Baldwin. 1981. "DNA Flexibility Studied by Covalent Closure of Short Fragments into Circles." Proceedings of the National Academy of Sciences of the United States of America 78 (8): 4833-37.

Shuldiner, Alan R., Ajay Nirula, and Jesse Roth. 1989. "Hybrid DNA Artifact from PCR of Closely Related Target Sequences." Nucleic Acids Research 17 (11): 4409-4409.

Wong, Koon Ho, Yi Jin, and Zarmik Moqtaderi. 2013. "Multiplex Illumina Sequencing Using DNA Barcoding." Current Protocols in Molecular Biology/Edited by Frederick M. Ausubel . . . [et Al.] Chapter 7: Unit 7.11.

Example 3

Materials and Methods

Circularization and RCA amplification of short PCR oligos.

| Materials | | |
|---|---|---|
| Backbone (BB) | BB2.4 with barcode 10-50 ng/µl | 243-244 bp |
| Insert (I) | blunt PCR amplicon 10-50 ng/µl | 100-250 bp |
| CutSmart Buffer | 10 X | (supplied with NEB#R0629) |
| ATP | 10 mM | (NEB#P0756) |
| dNTPs | 10 mM | (ThermoFisher#R0192) |
| T4 Ligase | 400 U/µl | (NEB#M0202S) |
| SrfI (Restr. Enz.) | 20 U/µl | (NEB#R0629) |
| Plasmid-Safe Buff. | 10 X | (Lucigen#E3101K) |
| Plasmid-Safe Enz. | 10 U/ul | (Lucigen#E3101K) |
| Annealing Buffer | 5 X | (50 mM Tris @ pH 7.5-8.0, 250 mM NaCl, 5 mM EDTA) |
| Phi29 Buffer | 10 X | (supplied with ThermoFisher#EP0091) |
| BSA | 10 mg/ml | (NEB&B9001) |
| Pyrophosphatase | 0.1 U/µl | (ThermoFisher#EF0221) |
| Phi29 DNA Polym. | 10 U/µl | (ThermoFisher#EP0091) |
| Exo-Res. RND Primers | 500 µM | (ThermoFisher#SO181) |
| Wizard SV Gel and PCR Clean-Up System | | (Promega#A9282) |

The backbone must be phosphorylated, either producing it via PCR using phosphorylated primers or using phosphorylation with PNK of a non-phosphorylated PCR product or synthetic DNA duplex (T4 Polynucleotide Kinase).

The insert must be dephosphorylated, either via PCR amplification using non-phosphorylated primers or using Antarctic Phosphatase.

Both, insert and backbone must be blunt. The preferred way is by using Phusion Polymerase (leaves blunt-ended amplicons).

Both insert and backbone must be buffer-free by column or bead purification.

In case the PCR reaction used to produce BB or I yielded more than one product, then gel-purification of the expected product is necessary.

If the template used for the amplification of I or BB is circular (a plasmid, for example), then gel-purification of the PCR product is necessary.

Methods

Circularization:

| Reaction Mix (1X): (BB:I molar ratio should be 3:1) | |
|---|---|
| BB | X µl |
| I | X µl |
| CutSmart Buffer (10X) | 5 µl |
| ATP (10 mM) | 10 µl (2 mM final concentration) |
| H2O | to 46 µl |
| T4 Ligase | 2 µl |
| SrfI (Restr. Enz.) | 2 µl |
| TOTAL | 50 µl |

Prepare the above Reaction Mix on ice and in PCR tubes. Vortex and Spin

Put in a Thermocycler and run the following program: (16° C.×10'>>37° C.×10')×8>>70° C.×20'

Add 1 µl of SrfI and run the following program: (this step is to digest any residual BB-BB) 37° C.×15'>>70° C.×20'

The suggested max amount of DNA that should be used in this reaction (considering both I and BB) is 400 ng in a 50 µl reaction. The BB:I ratio should not change.

Example ratio calculation: (len(X)=length of X, in base pairs), wherein: len(I)=130 bp; len(BB)=245 bp; len(BB)/len(I)=245/130=1.88; starting with 50 ng of I, then 50*1.88*3=282 ng of BB are needed to reach the 3:1 ratio.

Linear DNA Removal

Take 4 µl of the circularization reaction out as a negative control for the gel that will be run later.

To the rest of the circularization reaction (46 µl) add:

| ATP 10 mM | 6 µl |
|---|---|
| Plasmid-Safe Buffer 10X | 6 µl |
| Plasmid-Safe Enzyme | 2 µl |

Incubate at 37° C. for 30'

Inactivate at 70° C. for 30'

Run the whole reaction (S), together with the negative control (C−) in a 1.7% agarose gel.

Gel-purify the band corresponding to the Circular BB-I (FIG. 25).

Elute twice with 30 µl of H2O

Rolling Circle Amplification

To the purified Circular BB-I (around 50 µl at this point) add:

| Annealing Buffer (5X) | 12 µl |
|---|---|
| Exo-Res. RND Primers (500 µM) | 1 µl |

Heat the solution at 98° C. for 5', then let cool down slowly at R.T.

Add:

| | |
|---|---|
| Phi29 Buffer (10X) | 10 µl |
| BSA | 2 µl |
| dNTPs | 10 µl |
| Pyrophosphatase | 4 µl |
| Phi29 Polymerase | 2 µl |
| H2O | to 100 µl |

Incubate the reaction at 30° C. for at least 3 h.
Inactivate at 70° C. for 10'
Run 5 µl in a 0.5% agarose gel.

Running the RCA reaction overnight will yield more product. However, it is not yet clear if the quality of the concatemers will be affected.

Quality Check

The following procedure allows for a rough estimation of the amount of BB-I vs BB-only monomers present in the RCA product. Leveraging the presence of a restriction site (BglII in the following example) in the backbone, the RCA product can be digested and the resulting band pattern can be used to extrapolate the exact content of the RCA product.

As shown in FIG. 27, BB200_4 (243 bp) and S1_WT (158 bp) where circularized and amplified by RCA. When digesting concatemers made by BB-I, a band around 400 bp is expected, while if the concatemer consists of only BB, the resulting band should be around 250 bp. Concatemers formed by only I would not be digested leaving the RCA band visible.

Library Prep
DNA Purification:
Add an equal volume of Dynabeads, gently mix and incubate for 5 min at room temperature.
Insert the tube in the magnetic rack, wait 5 min to allow the beads to cluster on the wall
Remove the buffer
Gently wash with 700 µl of 70% ethanol
Remove the ethanol and repeat the washing step once more
Let residual ethanol evaporate
Remove the tube from the magnetic rack
Elute the DNA from the beads with 100 µl of ultrapure water
Resolve Branched DNA:
Add 4 µl of T7 Endonuclease (NEB #M0302S)
Incubate at 37° C.×1 h
Library Prep:
Proceed with Nanopore library prep, either 1D ligation prep or rapid prep.
List of Backbone and Insert Sequences Used
Backbone Properties:
len=backbone length in basepairs
mean_flex=mean value of the DNA flexibility computed over all consecutive segments of 50 basepairs contained in the sequence.
max_flex=is the max DNA flexibility computed for a segment of 50 basepairs in the sequence
entropy=Shannon entropy of the DNA sequence
GC %=percentage of GC bases in the backbone

```
>BB100_1
(len: 143 mean_flex: 12.89 max_flex: 14.71 entropy: 2.0 GC%: 48.25)
                                                       (SEQ ID NO: 9)
GGGCATGCACAGATGTACACGATTCCCAACACACCGTGCGGGCCATCGACCTATGCATA

CCGTACATATCATATATAAATCACATAATTTATTATACGTATGTCGCGCGGGTGGCTGT

GGGTAGATGCTGCATGACATAGCCC

>BB100_2
(len: 143 mean_flex: 13.29 max_flex: 14.95 entropy: 1.96 GC%: 37.76)
                                                      (SEQ ID NO: 10)
GGGCATGCACAGATGTACACGCACTACATGCCAATGCCCAAGCAGTGCGCATATCACGT

ATCATATCTAATATATTATAATATTATGATAATGAGTATTTATTTAATTTGTTTGTGTG

AGGTAGATGCTGCATGACATAGCCC

>BB100_3
(len: 143 mean_flex: 12.78 max_flex: 14.1 entropy: 1.95 GC%: 44.06)
                                                      (SEQ ID NO: 11)
GGGCATGCACAGATGTACACGCATTGGCCGTCTGTGCTGTCCATGGATCGTCTGATTGA

TATGATATCATATATTATAATTATACAGTAAGGTGATTGGGTATTGAGGGTTGTGTGGT

TGGTAGATGCTGCATGACATAGCCC

>BB100_4
(len: 145 mean_flex: 12.89 max_flex: 14.06 entropy: 1.95 GC%: 44.14)
                                                      (SEQ ID NO: 12)
GGGCATGCACAGATGTACACGGTAGACATGCGAAGCGTGCGATGACAATCGATGTGGAC

ATCATGCATATATATGTTGTATAATTAAACAAATATGTGTAGTGTGTGAGGTGGGTGTA

GGAAGTAGATGCTGCATGACATAGCCC
```

```
>BB100_5
(len: 143 mean_flex: 13.27 max_flex: 14.34 entropy: 1.9 GC%: 37.76)
                                                    (SEQ ID NO: 13)
GGGCATGCACAGATGTACACGTTGTCATGGGAATTTGTGGTTATGAAATGAGTATGCGA

CGAATATGTATACATATATATTAAATTATAGAGTGATGTATGAGTTTGTGATGTGTGGT

GTATAGATGCTGCATGACATAGCCC

>BB200_1
(len: 243 mean_flex: 13.0 max_flex: 14.9 entropy: 1.99 GC%: 44.86)
                                                    (SEQ ID NO: 14)
GGGCATGCACAGATGTACACGGCGGCGCAAGATGATGTGCCGAACCTGACATGGCATCG

ACTGGTATGGATCAATACTGATGCGATATCGATACCGGATAAATCATATATGCATAATA

TCACATTATATTAATTATAATACATCGGCGTACATATACACGTACGCATCATTTCACTA

TCTATCGGTACTATACGTAGTGCCGGTCTGTTGGCCGGGCGACATAGATGCTGCATGAC

ATAGCCC

>BB200_2
(len: 244 mean_flex: 13.15 max_flex: 14.69 entropy: 1.96 GC%: 38.52)
                                                    (SEQ ID NO: 15)
GGGCATGCACAGATGTACACGTGACGCAACGATGATGTTAGCTATTTGTTCAATGACAA

ATCTGGTATGATCAATACCGATGCGATATTGATATCTGATAACTCATATATGTAGAATA

TCACATTATATTTATTATAATACATCGTCGAACATATACACAATGCATCTTATCTATAC

GTATCGGGATAGCGTTGGCATAGCACTGGATGGCATGACCCTCATTAGATGCTGCATGA

CATAGCCC

>BB200_3
(len: 244 mean_flex: 13.06 max_flex: 14.9 entropy: 1.96 GC%: 39.75)
                                                    (SEQ ID NO: 16)
GGGCATGCACAGATGTACACGAGACCGCAAGATGATGTTCATTCTTGAACATGAGATCG

GATGGGTATGGATCAATACCGATGCGATATGATAACTGATAAATCATATATCTATAATA

TCACATTATATTAATTATAATACAGGATCGTTACATGCATACACAATGTATACTATACG

TATTCGGTAGTTAGTGTACGGTCGGAATGGAGGTGGTGGCGGTGATAGATGCTGCATGA

CATAGCCC

>BB200_4
(len: 243 mean_flex: 13.29 max_flex: 14.44 entropy: 1.93 GC%: 34.57)
                                                    (SEQ ID NO: 17)
GGGCATGCACAGATGTACACGAATCCCGAAGATGTTGTCCATTCATTGAATATGAGATC

TCATGGTATGATCAATATCGGATGCGATATTGATACTGATAAATCATATATGCATAATC

TCACATTATATTTATTATAATAAATCATCGTAGATATACACAATGTGAATTGTATACAA

TGGATAGTATAACTATCCAATTTCTTTGAGCATTGGCCTTGGTGTAGATGCTGCATGAC

ATAGCCC

>BB200_5
(len: 243 mean_flex: 13.37 max_flex: 14.52 entropy: 1.94 GC%: 35.8)
                                                    (SEQ ID NO: 18)
GGGCATGCACAGATGTACACGAATCCGTGAGATGACTATCTTATTTGTGACATTCATCG

ATCTGGATATGATCAATACCATGCGATATTGATTACTGATAAATCATATATGTAGAATA

TCACATTATATTAATTATAATAAATCGTCGTACATATACATCCACAATTAGCTATGTAT

ACTATCTATAGAGATGGTGCATCATCGTACTCCACCATTCCCACTAGATGCTGCATGAC

ATAGCCC

>BB300_1
(len: 348 mean_flex: 13.12 max_flex: 14.77 entropy: 1.98 GC%: 41.67)
                                                    (SEQ ID NO: 19)
GGGCATGCACAGATGTACACGCATAAGACCACAGGGTGCAAATCTGGATTGCGGCATGG

ATGATTCATCATCGTGGCATATTCGCTATGGATATATCCATCATAATACATTGATACGT
```

-continued

CATGCGTATAATCGCATTATATGTCGATATTGGTCATAGGGATACATCCGTGTATACTA

TCGTATATGCGTGCAATGTAGCCATGTTAATCATGCTATAACCATAACATAAATATAAT

ATATACAGATGGTGTATCTCTACTTATGTATGCTTGTATAGTAATGTCGATACTGATGG

GTCTCCGGCCCACTACACCACCTGGCCGCTCTAGATGCTGCATGACATAGCCC

```
>BB300_2
(len: 343 mean_flex: 13.26 max_flex: 14.34 entropy: 1.98 GC%: 40.82)
                                                    (SEQ ID NO: 20)
```

GGGCATGCACAGATGTACACGGGCAATCCGCCAGGGTTCAAATATGGATATGTGATGAT

CGATTCAACATGCACATATGCACGATATCATATATTACTCCAGATGTCATCATCGTCGT

GCGTATATGAGATATGTATTTATGCATATAATCCACCATACATGGTAGCGATATTATAG

TGCGATTATGTGTATATGACTATCATGGCTATTGTTAATATATAAATCATAACCATACC

ACTTCCACGCCTGGTATGGCGTATAGTATAGAGATATTGTGTGATGCCCTATGTCGACC

ATGATGTGCCGTTGTACTGCCAATCCTAGATGCTGCATGACATAGCCC

```
>BB300_3
(len: 344 mean_flex: 13.47 max_flex: 14.8 entropy: 1.95 GC%: 36.34)
                                                    (SEQ ID NO: 21)
```

GGGCATGCACAGATGTACACGTATCCATGCAGCTTATTGTAACTAGCGCATGCACGTGG

TGATTCATCACATCTATATATACGATATGATATATTACACATATTTGCATAGTATCATC

CGGTGTGATATCATCCGATATGCTCATACTTATTCATTGGTAGCATTGCATTGATGGAT

CAATAGTTATTATGACATCATGGCATGTACAATTATAAATAATCAACATACATAAATA

TACTATACACATCGTGTATGTGTTATACAGATCTGTGTGATGTATGATAATGTAATGGC

GTCGAACACCACAAGGCAGTCCTATAATAGATGCTGCATGACATAGCCC

```
>BB300_4
(len: 344 mean_flex: 13.37 max_flex: 14.57 entropy: 1.94 GC%: 37.5)
                                                    (SEQ ID NO: 22)
```

GGGCATGCACAGATGTACACGGTCCATTACAATCGAATCTATATCCCAATGTGTATCGA

TTATCACCACAATGACATAATACGATATCATATATTACTCCATATGCCTTACGTCAGAT

CGTTATATGAGATATGTATTCATGCATATGATATCCCACAGTACACGTCGTCTAATGCC

ATCATGAATGTATGACATATCTAGTCGATTATACATAATATAACATACCAATATAACAA

TATCTATACACATTTGATGGCGTATAGTATAAAGATATTGTGGCAATGCCCATACACCA

CTGACTGTCGCCGATCATTCCTACCACTAGATGCTGCATGACATAGCCC

```
>BB300_5
(len: 344 mean_flex: 13.51 max_flex: 14.89 entropy: 1.91 GC%: 33.43)
                                                    (SEQ ID NO: 23)
```

GGGCATGCACAGATGTACACGACCGACCGTGAAAGTGATTCAGAATGATGTGCATGAAT

GTTATCATGACATGATTTATGATGCACTGATATATGCATATTATAATATTGTACAATGT

CGTATATACGACATATCTATACTATGAATTATGGCATCATGGACAATAGATGGTAAGGT

ATAGTACGATCTATATAGCATGTTGAAATGGGATATAAATTATCATAAACATACATACT

TAACTAATATCAAGATGATATGTGTATGACATCAGAATGATAGTAGTAATGAGTATTGT

CAGATGTATGTACGAATATCACACGATTAGATGCTGCATGACATAGCCC

```
>Insert S1 WT (TP53, chr17:7577450-7577649)
                                                    (SEQ ID NO: 37)
```

AGGCTGGGGCACAGCAGGCCAGTGTGCAGGGTGGCAAGTGGCTCCTGACCTGGAGTCTT

CCAGTGTGATGATGGTGAGGATGGGCCTCCGGTTCATGCCGCCCATGCAGGAACTGTTA

CACATGTAGTTGTAGTGGATGGTGGTACAGTCAGAGCCAACCTAGGAGATAACACAGGC

CCAAGATGAGGCCAGTGCGCCTT

-continued

>Insert 17.2 (TP53, chr17:7578161-7578394)

(SEQ ID NO: 38)

CAGTTGCAAACCAGACCTCAGGCGGCTCATAGGGCACCACCACACTATGTCGAAAAGTG

TTTCTGTCATCCAAATACTCCACACGCAAATTTCCTTCCACTCGGATAAGATGCTGAGG

AGGGGCCAGACCTAAGAGCAATCAGTGAGGAATCAGAGGCCTGGGGACCCTGGGCAACC

AGCCCTGTCGTCTCTCCAGCCCCAGCTGCTCACCATCGCTATCTGAGCAGCGCTCAT

Bioinformatics Related to FIG. 24.

An expected reference signal for every possible insert (one for every possible basepair base pair at the target position) was generated using Tombo's DNA model (Fasta-→raw), both forward and reverse (github.com/nanoporetech/tombo). A forward and reverse expected signal were created for the backbone as well.

Using Dynamic Time Warping (DTW) the expected backbone signals were mapped to a read. If the expected backbone signals are overlapping in the alignment with the read, the best result is picked, and less optimal results were removed. The read is then cut into segments based on the direction of the fitted backbone.

Subsequently, all possible expected insert signals are mapped to the read using DTW. Again, overlapping results are removed and only the best results are kept.

Per read the most optimal fit (lowest DTW error) results are kept. The amount of times a particular insert (representing a specific base at the target position) determines the most likely base for this read at the target position.

Results

Circularization Efficiencies of Different Backbones

To be able to experimentally assess the efficiency of different backbones to circularize short DNA amplicons, a PCR amplicon of 234 bp (Insert 17.2) was ligated with backbones derived from 3 different backbone series: BB100_1/2/3/4/5, BB200_2/4/5 and BB300.

The backbone sequences and physical properties are reported below. The detailed protocol is disclosed in Materials and Methods.

The product of the circularization reaction is shown in FIG. 21 (left-side). Following circularization, the reaction was supplemented with an enzyme blend (Plasmid Safe Lucigen #E3101K) in order to digest the linear DNA. The residual product (circular DNA) is visible in FIG. 21 (right-side).

The BB200 series showed the best efficiency so far. To further characterize the efficiency of BB200_2/4/5, the 3 backbones were ligated with the same amplicon in absence of the restriction enzyme SrfI. The rationale behind this experiment is that, the ligation efficiency of a backbone can be estimated by the amount of multimers that can be formed in the reaction. As can be observed in FIG. 22, BB200_4 shows a remarkably higher ligation efficiency compared to BB200_2 and BB200_5.

The greater efficiency in ligation of BB200_4 is reflected in a greater efficiency in circularization and RCA product formation. In FIG. 23, sequencing read counts are plotted, coming from 2 independent experiments (blue and red) in which an equimolar mixture of BB200_2, BB200_4 and BB200_5 was used to produce concatemers. The sequencing results agree with the previous experiment showing that the great majority of the reads sequenced contains BB200_4.

New (optimized) barcode sequences that are better in terms of ligation efficiency BB200_4 is the most efficient backbone tested so far in a circularization reaction.

Strand-Specific Mutation Calling Coupled to the Possibility for Strand-Specific Rolling Circle Amplification The Cyclomics method produces a double-stranded DNA circle. One advantage of having a double-stranded circle is that one of the strands can be used preferentially as a template for the RCA, for example, by using a strand-specific primer to initiate the reaction, following known procedures (sciencedirect.com/science/article/pii/S0042682212002814). In this way, the Cyclomics method enables selective amplification of the sense or the antisense sequence of a given DNA sequencing. Such a strand-specific amplification it is not possible using the smartbell method, but has major benefits for obtaining accurate variant calls in an efficient way from nanopore sequencing data.

In FIG. 24, an example case is shown in which the rate of detection of the correct base is different when analyzing the data coming from two different strands of a DNA molecule. The data are derived from an experiment where a 200 bp (Insert 51 WT) long amplicon was circularized with BB200_4 and amplified as specified in the reported protocol.

Data analysis of the sequencing results allowed to determine the base-calling accuracy for each of the strands. In particular, it was noticed that C and A bases are often difficult to distinguish due to the similar intensity of their raw signal. However the signal coming from a T is quite different from all the other bases and easy to be correctly classified. For example, if an A is expected to be mutated in the forward strand, sequencing of the reverse strand would lead to much cleaner results since the A in the forward strand could be miss called as a G. Thus, specific enrichment of the reverse strand would be advantageous in such a scenario.

The data highlighted in FIG. 24 show one example of differences in discriminating bases on either the forward or the reverse strand. Note how the correct base can be inferred on the reverse strand data by using a simple cut-off over the Y-axis (Y<0.3). The same approach would not work with the forward strand. Thus, in this case, the amplification and sequencing of both strands would lead to a waste of data and, more problematically, to a misleading mutation detection on that particular position with a high false positive rate. In contrast, a strand-specific enrichment would lead to higher sensitivity (the majority of the reads would come from the best strand) and no false positive calls.

The invention claimed is:

1. A method for preparing double-stranded target DNA molecules for sequencing, the method comprising:
   providing double-stranded backbone DNA comprising 5' and 3' ends that are:
   ligation compatible with 5' and 3' ends of said target DNA;
   form a first restriction enzyme recognition site when self-ligated;
   in a form that enables self-ligation; and
   providing, if not already present, said target DNA with 5' and 3' ends that are in a form that prevents self-ligation and that are ligation compatible with said backbone DNA 5' and 3' ends;
   said method further comprising
   ligating said target DNA to said backbone DNA in the presence of a ligase and a first restriction enzyme that cuts said first restriction enzyme recognition site, thereby producing at least one DNA circle comprising a backbone DNA molecule and a target DNA molecule;
   optionally removing linear DNA;
   producing at least one concatemer DNA molecule comprising an ordered array of copies of said at least one DNA circle through rolling circle amplification; and
   sequencing said at least one concatemer,
   wherein
   target DNA is 20-300 base pairs;
   said form that allows self-ligation is a 5'-phosphate group of one DNA terminus and 3'-hydroxyl of another and said form that prevents self-ligation is a 5'-hydroxyl of one DNA terminus and 3'-hydroxyl of another;
   the ligation of an end of a target DNA to an end of a backbone creates a target-backbone junction with a sequence that cannot be recognized or cut by the restriction enzyme that cuts the restriction enzyme site that is formed by self-ligation of a backbone;
   said backbone comprises a linker, comprising a sequence of 20-900 nucleotides;
   said backbone has a length of 20-1000 nucleotides, and has a flexibility score of 10 or more.

2. The method of claim 1, wherein said at least one concatemer is sequenced by long read sequencing.

3. The method according to claim 2, wherein the ligation compatible 5' and 3' ends are blunt ends.

4. The method of claim 1, wherein two or more different backbones are provided.

5. The method of claim 4, wherein at least two backbones comprise a unique identifier sequence (barcode).

6. The method according to claim 5, wherein the ligation compatible 5' and 3' ends are blunt ends.

7. The method according to claim 4, wherein the ligation compatible 5' and 3' ends are blunt ends.

8. The method of claim 1, wherein the sequence of said linker does not have a repeated DNA motif of more than 5 nucleotides; or does not have a self-complementary motif of more than 6 nucleotides separated by less than 10 nucleotides or a combination thereof.

9. The method of claim 1, wherein said ligation compatible 5' and 3' ends are blunt ends.

10. The method of claim 1 further comprising:
    comparing target DNA capture efficiency between different backbones to assess the target DNA capture efficiency of a backbone.

* * * * *

SEQUENCE LISTING

<160> NUMBER OF SEQ ID NOS: 52

<210> SEQ ID NO 1
<211> LENGTH: 50
<212> TYPE: DNA
<213> ORGANISM: Artificial Sequence

```
<220> FEATURE:
<223> OTHER INFORMATION: example backbone sequence
<220> FEATURE:
<221> NAME/KEY: misc_feature
<222> LOCATION: (46)..(46)
<223> OTHER INFORMATION: n is a, c, g, or t

<400> SEQUENCE: 1
gggccctcag catttaaatg tcttcgagaa gaccatacta tcatgngccc              50

<210> SEQ ID NO 2
<211> LENGTH: 8
<212> TYPE: DNA
<213> ORGANISM: Artificial Sequence
<220> FEATURE:
<223> OTHER INFORMATION: SrfI restyriction site

<400> SEQUENCE: 2 gcccgggc                                                            8

<210> SEQ ID NO 3
<211> LENGTH: 8
<212> TYPE: DNA
<213> ORGANISM: Artificial Sequence
<220> FEATURE:
<223> OTHER INFORMATION: PmeI restriction site

<400> SEQUENCE: 3 gtttaaac                                                            8

<210> SEQ ID NO 4
<211> LENGTH: 8
<212> TYPE: DNA
<213> ORGANISM: Artificial Sequence
<220> FEATURE:
<223> OTHER INFORMATION: SweI restriction site

<400> SEQUENCE: 4 atttaaat                                                            8

<210> SEQ ID NO 5
<211> LENGTH: 199
<212> TYPE: DNA
<213> ORGANISM: Artificial Sequence
<220> FEATURE:
<223> OTHER INFORMATION: BB1

<400> SEQUENCE: 5
gggcatgcac agatgtacac gtacgatcat gtacgtcacg cgagtgcacg tcgtcatagc    60
tgtcgagtac tgtactgact gtctcgagcc tcagcgagta tttaaatcta cgtagagtac   120
gactgcgcag atgtgatcag tgactacgtg acactgtaca tcagcacgat cgatgactag   180
atgctgcatg acatagccc                                               199

<210> SEQ ID NO 6
<211> LENGTH: 259
<212> TYPE: DNA
<213> ORGANISM: Artificial Sequence
<220> FEATURE:
<223> OTHER INFORMATION: BB2

<400> SEQUENCE: 6
gggcatgcac agatgtacac gtacgatcat gtacgtcacg cgagtgcacg tcgtcatagc    60
tgtcgagtac tgtactgact gtctcgagcc tcagcgagta tttaaatcta cgtcaccggg   120
```

```
tcttcgagaa gacctgttta gagtacgact gcaaatggct ctagaggtac ccgttacata    180
acttacgcag atgtgatcag tgactacgtg acactgtaca tcagcacgat cgatgactag    240
atgctgcatg acatagccc                                                 259
```

<210> SEQ ID NO 7
<211> LENGTH: 341
<212> TYPE: DNA
<213> ORGANISM: Artificial Sequence
<220> FEATURE:
<223> OTHER INFORMATION: BB2_100

<400> SEQUENCE: 7

```
gggcatgcac agatgtacac gtacgatcat gtacgtcacg cgagtgcacg tcgtcatagc     60
tgtcgagtac tgtactgact gtctcgagcc tcagcgagta tttaaatcta cgtcaccata    120
tatatggata tatatatgga tatatatata tatggatata tggatatata tatatatata    180
tggatatgta tggatatata tatatatgga tatggatgtt tagagtacga ctgcaaatgg    240
ctctagaggt acccgttaca taacttacgc agatgtgatc agtgactacg tgacactgta    300
catcagcacg atcgatgact agatgctgca tgacatagcc c                        341
```

<210> SEQ ID NO 8
<211> LENGTH: 557
<212> TYPE: DNA
<213> ORGANISM: Artificial Sequence
<220> FEATURE:
<223> OTHER INFORMATION: BBpX2

<400> SEQUENCE: 8

```
gggcatgcac agatgtacac gaacgccagc aacgcggcct ttttacggtt cctggccttt     60
tgctggcctt ttgctcacat gtgagggcct atttcccatg attccttcat atttgcatat    120
acgatacaag gctgttagag ataattggaa ttaatttg actgtaaaca caaagatatt      180
agtacaaaat acgtgacgta gaaagtaata atttcttggg tagtttgcag ttttaaaatt    240 atgtttttaaa atggactatc atatgcttac cgtaacttga agtatttcg atttcttggc    300 tttatatatc ttgtggaaag gacgaaacac cgggtcttcg agaagacctg ttttagagct    360
agaaatagca agttaaaata aggctagtcc gttatcaact tgaaaaagtg gcaccgagtc    420
ggtgcttttt tgttttagag ctagaaatag caagttaaaa taaggctagt ccgttttttag   480 cgcgtgcgcc aattctgcag acaaatggct ctagaggtac ccgttacata acttatagat    540
gctgcatgac atagccc                                                   557
```

<210> SEQ ID NO 9
<211> LENGTH: 143
<212> TYPE: DNA
<213> ORGANISM: Artificial Sequence
<220> FEATURE:
<223> OTHER INFORMATION: BB100_1

<400> SEQUENCE: 9

```
gggcatgcac agatgtacac gattcccaac acaccgtgcg ggccatcgac ctatgcatac     60
cgtacatatc atatataaat cacataattt attatacgta tgtcgcgcgg gtggctgtgg    120
gtagatgctg catgacatag ccc                                            143
```

<210> SEQ ID NO 10
<211> LENGTH: 143
<212> TYPE: DNA
<213> ORGANISM: Artificial Sequence

```
<220> FEATURE:
<223> OTHER INFORMATION: BB100_2

<400> SEQUENCE: 10
gggcatgcac agatgtacac gcactacatg ccaatgccca agcagtgcgc atatcacgta      60
tcatatctaa tatattataa tattatgata atgagtattt atttaatttg tttgtgtgag     120
gtagatgctg catgacatag ccc                                             143

<210> SEQ ID NO 11
<211> LENGTH: 143
<212> TYPE: DNA
<213> ORGANISM: Artificial Sequence
<220> FEATURE:
<223> OTHER INFORMATION: BB100_3

<400> SEQUENCE: 11
gggcatgcac agatgtacac gcattggccg tctgtgctgt ccatggatcg tctgattgat      60
atgatatcat atattataat tatacagtaa ggtgattggg tattgagggt tgtgtggttg     120
gtagatgctg catgacatag ccc                                             143

<210> SEQ ID NO 12
<211> LENGTH: 145
<212> TYPE: DNA
<213> ORGANISM: Artificial Sequence
<220> FEATURE:
<223> OTHER INFORMATION: BB100_4

<400> SEQUENCE: 12
gggcatgcac agatgtacac ggtagacatg cgaagcgtgc gatgacaatc gatgtggaca      60
tcatgcatat atatgttgta taattaaaca aatatgtgta gtgtgtgagg tgggtgtagg     120
aagtagatgc tgcatgacat agccc                                           145

<210> SEQ ID NO 13
<211> LENGTH: 143
<212> TYPE: DNA
<213> ORGANISM: Artificial Sequence
<220> FEATURE:
<223> OTHER INFORMATION: BB100_5

<400> SEQUENCE: 13
gggcatgcac agatgtacac gttgtcatgg gaatttgtgg ttatgaaatg agtatgcgac      60
gaatatgtat acatatatat taaattatag agtgatgtat gagtttgtga tgtgtggtgt     120
atagatgctg catgacatag ccc                                             143

<210> SEQ ID NO 14
<211> LENGTH: 243
<212> TYPE: DNA
<213> ORGANISM: Artificial Sequence
<220> FEATURE:
<223> OTHER INFORMATION: BB200_1

<400> SEQUENCE: 14
gggcatgcac agatgtacac ggcggcgcaa gatgatgtgc cgaacctgac atggcatcga      60
ctggtatgga tcaatactga tgcgatatcg ataccggata aatcatatat gcataatatc     120
acattatatt aattataata catcggcgta catatacacg tacgcatcat ttcactatct     180
atcggtacta tacgtagtgc cggtctgttg gccgggcgac atagatgctg catgacatag     240
ccc                                                                   243
```

```
<210> SEQ ID NO 15
<211> LENGTH: 244
<212> TYPE: DNA
<213> ORGANISM: Artificial Sequence
<220> FEATURE:
<223> OTHER INFORMATION: BB200_2

<400> SEQUENCE: 15
gggcatgcac agatgtacac gtgacgcaac gatgatgtta gctatttgtt caatgacaaa      60
tctggtatga tcaataccga tgcgatattg atatctgata actcatatat gtagaatatc     120
acattatatt tattataata catcgtcgaa catatacaca atgcatctta tctatacgta     180
tcgggatagc gttggcatag cactggatgg catgaccctc attagatgct gcatgacata     240
gccc                                                                  244

<210> SEQ ID NO 16
<211> LENGTH: 244
<212> TYPE: DNA
<213> ORGANISM: Artificial Sequence
<220> FEATURE:
<223> OTHER INFORMATION: BB200_3

<400> SEQUENCE: 16
gggcatgcac agatgtacac gagaccgcaa gatgatgttc attcttgaac atgagatcgg      60
atgggtatgg atcaataccg atgcgatatg ataactgata aatcatatat ctataatatc     120
acattatatt aattataata caggatcgtt acatgcatac acaatgtata ctatacgtat     180
tcggtagtta gtgtacggtc ggaatggagg tggtggcggt gatagatgct gcatgacata     240
gccc                                                                  244

<210> SEQ ID NO 17
<211> LENGTH: 243
<212> TYPE: DNA
<213> ORGANISM: Artificial Sequence
<220> FEATURE:
<223> OTHER INFORMATION: BB200_4

<400> SEQUENCE: 17
gggcatgcac agatgtacac gaatcccgaa gatgttgtcc attcattgaa tatgagatct      60
catggtatga tcaatatcgg atgcgatatt gatactgata aatcatatat gcataatctc     120
acattatatt tattataata aatcatcgta gatatacaca atgtgaattg tatacaatgg     180
atagtataac tatccaattt ctttgagcat tggccttggt gtagatgctg catgacatag     240
ccc                                                                   243

<210> SEQ ID NO 18
<211> LENGTH: 243
<212> TYPE: DNA
<213> ORGANISM: Artificial Sequence
<220> FEATURE:
<223> OTHER INFORMATION: BB200_5

<400> SEQUENCE: 18
gggcatgcac agatgtacac gaatccgtga gatgactatc ttatttgtga cattcatcga      60
tctggatatg atcaatacca tgcgatattg attactgata aatcatatat gtagaatatc     120
acattatatt aattataata aatcgtcgta catatacatc cacaattagc tatgtatact     180
atctatagag atggtgcatc atcgtactcc accattccca ctagatgctg catgacatag     240
ccc                                                                   243
```

```
<210> SEQ ID NO 19
<211> LENGTH: 348
<212> TYPE: DNA
<213> ORGANISM: Artificial Sequence
<220> FEATURE:
<223> OTHER INFORMATION: BB300_1

<400> SEQUENCE: 19
gggcatgcac agatgtacac gcataagacc acagggtgca atctggatt gcggcatgga        60 tgattcatca tcgtggcata ttcgctatgg atatatccat cataatacat tgatacgtca       120
tgcgtataat cgcattatat gtcgatattg gtcataggga tacatccgtg tatactatcg       180
tatatgcgtg caatgtagcc atgttaatca tgctataacc ataacataaa tataatatat       240
acagatggtg tatctctact tatgtatgct tgtatagtaa tgtcgatact gatgggtctc       300
cggcccacta caccacctgg ccgctctaga tgctgcatga catagccc                    348

<210> SEQ ID NO 20
<211> LENGTH: 343
<212> TYPE: DNA
<213> ORGANISM: Artificial Sequence
<220> FEATURE:
<223> OTHER INFORMATION: BB300_2

<400> SEQUENCE: 20
gggcatgcac agatgtacac gggcaatccg ccagggttca aatatggata tgtgatgatc        60
gattcaacat gcacatatgc acgatatcat atattactcc agatgtcatc atcgtcgtgc       120
gtatatgaga tatgtattta tgcatataat ccaccataca tggtagcgat attatagtgc       180
gattatgtgt atatgactat catggctatt gttaatatat aaatcataac cataccactt       240
ccacgcctgg tatggcgtat agtatagaga tattgtgtga tgccctatgt cgaccatgat       300
gtgccgttgt actgccaatc ctagatgctg catgacatag ccc                         343

<210> SEQ ID NO 21
<211> LENGTH: 344
<212> TYPE: DNA
<213> ORGANISM: Artificial Sequence
<220> FEATURE:
<223> OTHER INFORMATION: BB300_3

<400> SEQUENCE: 21
gggcatgcac agatgtacac gtatccatgc agcttattgt aactagcgca tgcacgtggt        60
gattcatcac atctatatat acgatatgat atattacaca tatttgcata gtatcatccg       120
gtgtgatatc atccgatatg ctcatactta ttcattggta gcattgcatt gatggatcaa       180
tagttattat gacatcatgg catgtacaat tataaataat acaacataca taaatatact       240
atacacatcg tgtatgtgtt atacagatct gtgtgatgta tgataatgta atggcgtcga       300
acaccacaag gcagtcctat aatagatgct gcatgacata gccc                        344

<210> SEQ ID NO 22
<211> LENGTH: 344
<212> TYPE: DNA
<213> ORGANISM: Artificial Sequence
<220> FEATURE:
<223> OTHER INFORMATION: BB300_4

<400> SEQUENCE: 22
gggcatgcac agatgtacac ggtccattac aatcgaatct atatcccaat gtgtatcgat        60
tatcaccaca atgacataat acgatatcat atattactcc atatgcctta cgtcagatcg       120
```

```
ttatatgaga tatgtattca tgcatatgat atcccacagt acacgtcgtc taatgccatc    180
atgaatgtat gacatatcta gtcgattata cataatataa cataccaata taacaatatc    240
tatacacatt tgatggcgta gtataaag atattgtggc aatgcccata caccactgac      300
tgtcgccgat cattcctacc actagatgct gcatgacata gccc                     344

<210> SEQ ID NO 23
<211> LENGTH: 344
<212> TYPE: DNA
<213> ORGANISM: Artificial Sequence
<220> FEATURE:
<223> OTHER INFORMATION: BB300_5

<400> SEQUENCE: 23
gggcatgcac agatgtacac gaccgaccgt gaaagtgatt cagaatgatg tgcatgaatg    60
ttatcatgac atgatttatg atgcactgat atatgcatat tataatattg tacaatgtcg    120
tatatacgac atatctatac tatgaattat ggcatcatgg acaatagatg gtaaggtata    180
gtacgatcta tatagcatgt tgaaatggga tataaattat cataaacata catacttaac    240
taatatcaag atgatatgtg tatgacatca gaatgatagt agtaatgagt attgtcagat    300
gtatgtacga atatcacacg attagatgct gcatgacata gccc                     344

<210> SEQ ID NO 24
<211> LENGTH: 341
<212> TYPE: DNA
<213> ORGANISM: Artificial Sequence
<220> FEATURE:
<223> OTHER INFORMATION: BB2_100

<400> SEQUENCE: 24
gggcatgcac agatgtacac gtacgatcat gtacgtcacg cgagtgcacg tcgtcatagc    60
tgtcgagtac tgtactgact gtctcgagcc tcagcgagta tttaaatcta cgtcaccata    120
tatatggata tatatatgga tatatatata tatggatata tggatatata tatatatata    180
tggatatgta tggatatata tatatatgga tatggatgtt tagagtacga ctgcaaatgg    240
ctctagaggt acccgttaca taacttacgc agatgtgatc agtgactacg tgacactgta    300
catcagcacg atcgatgact agatgctgca tgacatagcc c                        341

<210> SEQ ID NO 25
<211> LENGTH: 514
<212> TYPE: DNA
<213> ORGANISM: Artificial Sequence
<220> FEATURE:
<223> OTHER INFORMATION: BB3

<400> SEQUENCE: 25
aacgccagca acgcggcctt tttacggttc ctggcctttt gctggccttt tgctcacatg    60
tgagggccta tttcccatga ttccttcata tttgcatata cgatacaagg ctgttagaga    120
gataattgga attaatttga ctgtaaacac aaagatatta gtacaaaata cgtgacgtag    180
aaagtaataa tttcttgggt agtttgcagt tttaaaatta tgttttaaaa tggactatca    240
tatgcttacc gtaacttgaa agtatttcga tttcttggct ttatatatct tgtggaaagg    300
acgaaacacc gggtcttcga aagacctgt tttagagcta gaaatagcaa gttaaaataa    360
ggctagtccg ttatcaactt gaaaaagtgg caccgagtcg gtgcttttt gttttagagc    420 tagaaatagc aagttaaaat aaggctagtc cgttttttagc gcgtgcgcca attctgcaga    480
caaatggctc tagaggtacc cgttacataa ctta                                514
```

```
<210> SEQ ID NO 26
<211> LENGTH: 108
<212> TYPE: DNA
<213> ORGANISM: Artificial Sequence
<220> FEATURE:
<223> OTHER INFORMATION: insert BB2_100

<400> SEQUENCE: 26
caccatatat atggatatat atatggatat atatatatat ggatatatgg atatatatat    60
atatatatgg atatgtatgg atatatatat atatggatat ggatgttt                108

<210> SEQ ID NO 27
<211> LENGTH: 104
<212> TYPE: DNA
<213> ORGANISM: Artificial Sequence
<220> FEATURE:
<223> OTHER INFORMATION: sense oligo

<400> SEQUENCE: 27
caccatatat atggatatat atatggatat atatatatat ggatatatgg atatatatat    60
atatatatgg atatgtatgg atatatatat atatggatat ggat                    104

<210> SEQ ID NO 28
<211> LENGTH: 104
<212> TYPE: DNA
<213> ORGANISM: Artificial Sequence
<220> FEATURE:
<223> OTHER INFORMATION: antisense oligo

<400> SEQUENCE: 28
aaacatccat atccatatat atatatatcc atacatatcc atatatatat atatatatcc    60
atatatccat atatatatat atccatatat atatccatat atat                    104

<210> SEQ ID NO 29
<211> LENGTH: 38
<212> TYPE: DNA
<213> ORGANISM: Artificial Sequence
<220> FEATURE:
<223> OTHER INFORMATION: BBpX to BBpX2 - F

<400> SEQUENCE: 29
gggcatgcac agatgtacac gaacgccagc aacgcggc                            38

<210> SEQ ID NO 30
<211> LENGTH: 45
<212> TYPE: DNA
<213> ORGANISM: Artificial Sequence
<220> FEATURE:
<223> OTHER INFORMATION: BBpX to BBpX2 - R

<400> SEQUENCE: 30
gggctatgtc atgcagcatc tataagttat gtaacgggta cctct                    45

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
gggcatgcac agatgtacac g                                              21
```

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
gggctatgtc atgcagcatc ta                                                22

<210> SEQ ID NO 33
<211> LENGTH: 161
<212> TYPE: DNA
<213> ORGANISM: Artificial Sequence
<220> FEATURE:
<223> OTHER INFORMATION: insert 17.1

<400> SEQUENCE: 33
taactgcacc cttggtctcc tccaccgctt cttgtcctgc ttgcttacct cgcttagtgc       60
tccctggggg cagctcgtgg tgaggctccc ctttcttgcg gagattctct tcctctgtgc      120
gccggtctct cccaggacag gcacaaacac gcacctcaaa g                          161

<210> SEQ ID NO 34
<211> LENGTH: 234
<212> TYPE: DNA
<213> ORGANISM: Artificial Sequence
<220> FEATURE:
<223> OTHER INFORMATION: insert 17.2

<400> SEQUENCE: 34
cagttgcaaa ccagacctca ggcggctcat agggcaccac cacactatgt cgaaaagtgt       60
ttctgtcatc caaatactcc acacgcaaat ttccttccac tcggataaga tgctgaggag      120
gggccagacc taagagcaat cagtgaggaa tcagaggcct ggggaccctg ggcaaccagc      180
cctgtcgtct ctccagcccc agctgctcac catcgctatc tgagcagcgc tcat            234

<210> SEQ ID NO 35
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (18)..(19)
<223> OTHER INFORMATION: phosphothionated

<400> SEQUENCE: 35
atgagcgctg ctcagatag                                                    19

<210> SEQ ID NO 36
<211> LENGTH: 20
<212> TYPE: DNA
<213> ORGANISM: Artificial Sequence
<220> FEATURE:
<223> OTHER INFORMATION: primer 17.2F

<400> SEQUENCE: 36
cagttgcaaa ccagacctca                                                   20

<210> SEQ ID NO 37
<211> LENGTH: 200
<212> TYPE: DNA
<213> ORGANISM: Artificial Sequence

```
<220> FEATURE:
<223> OTHER INFORMATION: Insert S1 WT

<400> SEQUENCE: 37
aggctggggc acagcaggcc agtgtgcagg gtggcaagtg gctcctgacc tggagtcttc     60
cagtgtgatg atggtgagga tgggcctccg gttcatgccg cccatgcagg aactgttaca    120
catgtagttg tagtggatgg tggtacagtc agagccaacc taggagataa cacaggccca    180
agatgaggcc agtgcgcctt                                                200

<210> SEQ ID NO 38
<211> LENGTH: 234
<212> TYPE: DNA
<213> ORGANISM: Artificial Sequence
<220> FEATURE:
<223> OTHER INFORMATION: Insert 17.2

<400> SEQUENCE: 38
cagttgcaaa ccagacctca ggcggctcat agggcaccac cacactatgt cgaaaagtgt     60
ttctgtcatc caaatactcc acacgcaaat ttccttccac tcggataaga tgctgaggag    120
gggccagacc taagagcaat cagtgaggaa tcagaggcct ggggaccctg ggcaaccagc    180
cctgtcgtct ctccagcccc agctgctcac catcgctatc tgagcagcgc tcat          234

<210> SEQ ID NO 39
<211> LENGTH: 38
<212> TYPE: DNA
<213> ORGANISM: Artificial Sequence
<220> FEATURE:
<223> OTHER INFORMATION: nanopore sequence read consensus

<400> SEQUENCE: 39
ggtgttcagg cagtgttaaa gcagttgatt ttattcac                             38

<210> SEQ ID NO 40
<211> LENGTH: 80
<212> TYPE: DNA
<213> ORGANISM: Artificial Sequence
<220> FEATURE:
<223> OTHER INFORMATION: nanopore sequence read

<400> SEQUENCE: 40
ttacgccgga tagatgtaat tattcgagct gaagtgttaa agcagttgat tttattcact     60
atgatgaaaa acagtaagat                                                 80

<210> SEQ ID NO 41
<211> LENGTH: 76
<212> TYPE: DNA
<213> ORGANISM: Artificial Sequence
<220> FEATURE:
<223> OTHER INFORMATION: nanopore sequence read

<400> SEQUENCE: 41
ctacgccgga tggatagatg ttcaggctag agtattaaag cagttgattt tattgctatg     60
atgaaaaaca atgaat                                                     76

<210> SEQ ID NO 42
<211> LENGTH: 82
<212> TYPE: DNA
<213> ORGANISM: Artificial Sequence
<220> FEATURE:
<223> OTHER INFORMATION: nanopore sequence read
```

<400> SEQUENCE: 42
ttacgcggat ggatgctgga gtgttcaggc acaaattaat taaagcagtt gattttattc   60
actaagtaga aaaacaatag at   82

<210> SEQ ID NO 43
<211> LENGTH: 77
<212> TYPE: DNA
<213> ORGANISM: Artificial Sequence
<220> FEATURE:
<223> OTHER INFORMATION: nanopore sequence read

<400> SEQUENCE: 43
ttacgccgga tggatatggt gttcaggcac aaattaaagc agttgatttt attcactatg   60
atgaaaaagc aatggat   77

<210> SEQ ID NO 44
<211> LENGTH: 75
<212> TYPE: DNA
<213> ORGANISM: Artificial Sequence
<220> FEATURE:
<223> OTHER INFORMATION: nanopore sequence read

<400> SEQUENCE: 44
ttacatggat ggatgagtgt caggcacaga aattaaaaac cagttgattt taggcactgg   60
tgaaaaacaa tgaat   75

<210> SEQ ID NO 45
<211> LENGTH: 76
<212> TYPE: DNA
<213> ORGANISM: Artificial Sequence
<220> FEATURE:
<223> OTHER INFORMATION: nanopore sequence read

<400> SEQUENCE: 45
ttacgccgga tggatatggt gttcaggcac aagtattaaa gcagttgatt ttattctatg   60
atgaaaaaca atggat   76

<210> SEQ ID NO 46
<211> LENGTH: 83
<212> TYPE: DNA
<213> ORGANISM: Artificial Sequence
<220> FEATURE:
<223> OTHER INFORMATION: nanopore sequence read

<400> SEQUENCE: 46
gcccacgcca gggatggata tgatgttcag gcacagagta ttattaagca gttgatttgt   60
cactatgatg aaaacaaga gat   83

<210> SEQ ID NO 47
<211> LENGTH: 81
<212> TYPE: DNA
<213> ORGANISM: Artificial Sequence
<220> FEATURE:
<223> OTHER INFORMATION: nanopore sequence read

<400> SEQUENCE: 47
tgtgcgccgg atggatatag gtgttcaggc acaagtgtta aagcagttga ttttattcac   60
tatgatgaaa aacagtaaga t   81

```
<210> SEQ ID NO 48
<211> LENGTH: 80
<212> TYPE: DNA
<213> ORGANISM: Artificial Sequence
<220> FEATURE:
<223> OTHER INFORMATION: nanopore sequence read

<400> SEQUENCE: 48
atacgccgga tggatatggt gttcaggcac aagtgttaaa gcagttgatt ttattcacta     60
tgatagaaaa acaatggaat                                                 80

<210> SEQ ID NO 49
<211> LENGTH: 77
<212> TYPE: DNA
<213> ORGANISM: Artificial Sequence
<220> FEATURE:
<223> OTHER INFORMATION: nanopore sequence read

<400> SEQUENCE: 49
ttacgccgga tggatgggtg ttcaggcaca agtcttaaag cagttgattt tattcactat     60
gatgaaaaac aatgaat                                                    77

<210> SEQ ID NO 50
<211> LENGTH: 24
<212> TYPE: DNA
<213> ORGANISM: Artificial Sequence
<220> FEATURE:
<223> OTHER INFORMATION: TP53 derived mutation sequencing read
<220> FEATURE:
<221> NAME/KEY: CDS
<222> LOCATION: (1)..(24)

<400> SEQUENCE: 50 ttc cac tcg gat aag atg ctg agg                                       24
Phe His Ser Asp Lys Met Leu Arg
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Phe His Ser Asp Lys Met Leu Arg
1               5

<210> SEQ ID NO 52
<211> LENGTH: 50
<212> TYPE: DNA
<213> ORGANISM: Artificial Sequence
<220> FEATURE:
<223> OTHER INFORMATION: example backbone sequence
<220> FEATURE:
<221> NAME/KEY: misc_feature
<222> LOCATION: (5)..(5)
<223> OTHER INFORMATION: n is a, c, g, or t

<400> SEQUENCE: 52
gggcncatga tagtatggtc ttctcgaaga catttaaatg ctgagggccc                50
```